(12) United States Patent
Yusibov et al.

(10) Patent No.: US 8,404,252 B2
(45) Date of Patent: Mar. 26, 2013

(54) YERSINIA PESTIS ANTIGENS, VACCINE COMPOSITIONS, AND RELATED METHODS

(75) Inventors: Vidadi Yusibov, Havertown, PA (US); Vadim Mett, Newark, DE (US); Konstantin Musiychuk, Newark, DE (US)

(73) Assignee: Fraunhofer USA, Inc., Plymouth, MI (US)

( * ) Notice: Subject to any disclaimer, the term of this patent is extended or adjusted under 35 U.S.C. 154(b) by 3 days.

(21) Appl. No.: 12/668,258

(22) PCT Filed: Jul. 11, 2008

(86) PCT No.: PCT/US2008/069860
§ 371 (c)(1), (2), (4) Date: Oct. 22, 2010

(87) PCT Pub. No.: WO2009/009759
PCT Pub. Date: Jan. 15, 2009

(65) Prior Publication Data
US 2011/0027304 A1    Feb. 3, 2011

Related U.S. Application Data

(60) Provisional application No. 60/949,115, filed on Jul. 11, 2007.

(51) Int. Cl.
*A61K 39/102* (2006.01)
*A61K 39/02* (2006.01)
*C07K 14/24* (2006.01)

(52) U.S. Cl. ............ 424/255.1; 424/190.1; 424/192.1; 530/350

(58) Field of Classification Search .................. None
See application file for complete search history.

(56) References Cited

U.S. PATENT DOCUMENTS

| | | |
|---|---|---|
| 4,196,265 A | 4/1980 | Koprowski et al. |
| 4,270,537 A | 6/1981 | Romaine |
| 4,596,556 A | 6/1986 | Morrow et al. |
| 4,653,728 A | 3/1987 | Mochizuki et al. |
| 4,790,824 A | 12/1988 | Morrow et al. |
| 4,816,567 A | 3/1989 | Cabilly et al. |
| 4,886,499 A | 12/1989 | Cirelli et al. |
| 4,935,496 A | 6/1990 | Kudo et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,223,409 A | 6/1993 | Ladner et al. |
| 5,312,335 A | 5/1994 | McKinnon et al. |
| 5,316,931 A | 5/1994 | Donson et al. |
| 5,328,483 A | 7/1994 | Jacoby |
| 5,334,144 A | 8/1994 | Alchas et al. |
| 5,339,163 A | 8/1994 | Homma et al. |
| 5,383,851 A | 1/1995 | McKinnon, Jr. et al. |
| 5,403,484 A | 4/1995 | Ladner et al. |
| 5,417,662 A | 5/1995 | Hjertman et al. |
| 5,427,908 A | 6/1995 | Dower et al. |
| 5,466,220 A | 11/1995 | Brenneman |
| 5,480,381 A | 1/1996 | Weston |
| 5,502,167 A | 3/1996 | Waldmann et al. |
| 5,503,627 A | 4/1996 | McKinnon et al. |
| 5,520,639 A | 5/1996 | Peterson et al. |
| 5,527,288 A | 6/1996 | Gross et al. |
| 5,530,101 A | 6/1996 | Queen et al. |
| 5,545,806 A | 8/1996 | Lonberg et al. |
| 5,545,807 A | 8/1996 | Surani et al. |
| 5,558,864 A | 9/1996 | Bendig et al. |
| 5,565,332 A | 10/1996 | Hoogenboom et al. |
| 5,569,189 A | 10/1996 | Parsons |
| 5,580,717 A | 12/1996 | Dower et al. |
| 5,585,089 A | 12/1996 | Queen et al. |
| 5,591,828 A | 1/1997 | Bosslet et al. |
| 5,599,302 A | 2/1997 | Lilley et al. |
| 5,649,912 A | 7/1997 | Peterson |
| 5,681,722 A | 10/1997 | Newman et al. |
| 5,693,493 A | 12/1997 | Robinson et al. |
| 5,693,761 A | 12/1997 | Queen et al. |
| 5,693,762 A | 12/1997 | Queen et al. |
| 5,698,417 A | 12/1997 | Robinson et al. |
| 5,698,426 A | 12/1997 | Huse et al. |
| 5,702,892 A | 12/1997 | Mulligan-Kehoe |
| 5,704,911 A | 1/1998 | Parsons |
| 5,705,154 A | 1/1998 | Dalie et al. |
| 5,733,743 A | 3/1998 | Johnson et al. |
| 5,750,078 A | 5/1998 | Shitara et al. |
| 5,759,817 A | 6/1998 | Barbas |
| 5,770,403 A | 6/1998 | Dalie et al. |
| 5,770,429 A | 6/1998 | Lonberg et al. |
| 5,855,866 A | 1/1999 | Thorpe et al. |
| 5,877,289 A | 3/1999 | Thorpe et al. |
| 5,888,789 A | 3/1999 | Rodriguez et al. |
| 5,893,397 A | 4/1999 | Peterson et al. |
| 5,965,132 A | 10/1999 | Thorpe et al. |
| 5,993,412 A | 11/1999 | Deily et al. |

(Continued)

FOREIGN PATENT DOCUMENTS

| | | |
|---|---|---|
| EP | 404097 | 6/1990 |
| WO | WO9311161 | 6/1993 |

(Continued)

OTHER PUBLICATIONS

Air, "Mechanism of antigenic variation in an individual epitope on influenza virus N9 neuraminidase," *J. Virology*, 64(12):5797-5803, 1990.

(Continued)

*Primary Examiner* — Padma Baskar
(74) *Attorney, Agent, or Firm* — Fish & Richardson P.C.

(57) ABSTRACT

The present invention provides antigens and vaccines useful in prevention of infection by *Yersinia pestis*. The present invention provides pharmaceutical compositions of such antigens and/or vaccines. The present invention provides methods for the production of *Y. pestis* protein antigens in plants, as well as methods for their use in the treatment and/or prevention of *Y. pestis* infection.

18 Claims, 29 Drawing Sheets

U.S. PATENT DOCUMENTS

| | | | |
|---|---|---|---|
| 6,042,832 | A | 3/2000 | Koprowski et al. |
| 6,044,555 | A | 4/2000 | Thorpe et al. |
| 6,093,399 | A | 7/2000 | Thorpe et al. |
| 6,103,511 | A | 8/2000 | Li et al. |
| 6,261,535 | B1 | 7/2001 | Thorpe et al. |
| 6,524,825 | B1 | 2/2003 | Mizzen et al. |
| 6,649,172 | B2 | 11/2003 | Johnson |
| 6,734,173 | B1 | 5/2004 | Wu et al. |
| 6,740,740 | B2 | 5/2004 | Garger et al. |
| 6,797,491 | B2 | 9/2004 | Neefe, Jr. et al. |
| 6,841,659 | B2 | 1/2005 | Turpen et al. |
| 7,794,731 | B2 * | 9/2010 | Mizel et al. ............ 424/234.1 |
| 7,888,135 | B2 | 2/2011 | Tarleton et al. |
| 2004/0093643 | A1 | 5/2004 | Ensley |
| 2004/0170606 | A1 | 9/2004 | Palmer et al. |
| 2004/0268442 | A1 | 12/2004 | Miller et al. |
| 2005/0026291 | A1 | 2/2005 | Fedorkin et al. |
| 2005/0042229 | A1 | 2/2005 | Yang et al. |
| 2005/0048074 | A1 | 3/2005 | Cardineau et al. |
| 2005/0054820 | A1 | 3/2005 | Wu et al. |
| 2005/0114920 | A1 | 5/2005 | Yusibov et al. |
| 2005/0186621 | A1 | 8/2005 | Galarza et al. |
| 2006/0008473 | A1 | 1/2006 | Yang et al. |
| 2006/0265787 | A1 | 11/2006 | Piruzian et al. |
| 2007/0275014 | A1 | 11/2007 | Yusibov et al. |
| 2008/0124272 | A1 | 5/2008 | Yusibov et al. |
| 2008/0279877 | A1 | 11/2008 | Yusibov et al. |
| 2009/0324634 | A1 | 12/2009 | Knapp et al. |
| 2010/0227373 | A1 | 9/2010 | Yusibov et al. |
| 2011/0059130 | A1 | 3/2011 | Yusibov |

FOREIGN PATENT DOCUMENTS

| | | |
|---|---|---|
| WO | WO9602555 | 2/1996 |
| WO | WO9612028 | 4/1996 |
| WO | WO9713537 | 4/1997 |
| WO | WO9737705 | 10/1997 |
| WO | WO9814595 | 4/1998 |
| WO | WO9845331 | 10/1998 |
| WO | WO9907860 | 2/1999 |
| WO | WO0020612 | 4/2000 |
| WO | WO0025574 | 5/2000 |
| WO | WO0046350 | 8/2000 |
| WO | WO0200892 | 1/2002 |
| WO | WO03040179 | 5/2003 |
| WO | WO03076568 | 9/2003 |
| WO | WO2004043886 | 5/2004 |
| WO | WO2004058797 | 7/2004 |
| WO | WO2005023177 | 3/2005 |
| WO | WO2005026375 | 3/2005 |
| WO | WO2005049839 | 6/2005 |
| WO | WO2005056052 | 6/2005 |
| WO | WO2005067620 | 7/2005 |
| WO | WO2005081905 | 9/2005 |
| WO | WO2005120567 | 12/2005 |
| WO | WO2006003018 | 1/2006 |
| WO | WO2006124712 | 11/2006 |
| WO | WO2007089753 | 8/2007 |
| WO | WO2007095304 | 8/2007 |
| WO | WO2007095318 | 8/2007 |
| WO | WO2007149715 | 12/2007 |
| WO | WO2008021959 | 2/2008 |
| WO | WO2008033105 | 3/2008 |
| WO | WO2008033159 | 3/2008 |
| WO | WO2008048945 | 4/2008 |
| WO | WO2008110937 | 9/2008 |
| WO | WO2008134643 | 11/2008 |
| WO | WO2009/009759 | 1/2009 |
| WO | WO2009026397 | 2/2009 |
| WO | WO2009024708 | 4/2009 |
| WO | WO2009058355 | 5/2009 |
| WO | WO2010036970 | 4/2010 |
| WO | WO2010037046 | 4/2010 |

OTHER PUBLICATIONS

Anderson et al., "Recombinant V antigen protects mice against pneumonic and bubonic plague caused by F1-capsule-positive and -negative strains of *Yersinia pestis*," *Infect. Immun.*, 64(11):4580-4585, 1996.

Andrews et al., "Fraction 1 Capsular Antigen (F1) Purification from *Yersinia pestis* CO92 and from an *Escherichia coli* recombinant strain and efficacy against lethal plague challenge," *Infect. Immun.*, 64(6):2180-2187, 1996.

Aymard et al., "Neuraminidase assays," *Developments in Biologicals*, 115:75-83, 2003 (with English summary).

Barbas et al., "Assembly of combinatorial antibody libraries on phage surfaces: The gene III site," *Proc. Natl. Acad. Sci. USA*, 88:7978, 1991.

Barbas et al., "Semisynthetic combinatorial antibody libraries: A chemical solution to the diversity problem," *Proc. Natl. Acad. Sci. USA*, 89:4457, 1992.

Berger et al., "Therapeutic applications of monoclonal antibodies," *Am J Med Sci.*, 324(1):14-30, 2002.

Brodzik et al., "Advances in alfalfa mosaic virus-mediated expression of anthrax antigen *in planta,*" *Biochem. Biophys. Res. Commun.*, 338( 2):717-722, 2005.

Burke et al., "Cloning of large segments of exogenous DNA into yeast by means of artificial chromosome vectors," *Science*, 236:806, 1987.

Chain et al., "Complete genome sequence of *Yersinia pestis* strains Antigua and Nepal516: evidence of gene reduction in an emerging pathogen," *J. Bacteriol.*, 188(12):4453-63, 2006.

Chichester et al., "Different response requirements for IFNγ production in ELISPOT assays by CD4+ T cells from mice early and late after submission," *J. Immunol. Methods*, 309:99-107, 2006.

Davies et al., "Affinity improvement of single antibody VH domains: residues in all three hypervariable regions affect antigen binding," *Immunotechnology*, 2(3):169-179, 1996.

Deng et al., "Genome sequence of *Yersinia pestis* KIM," *J. Bacteriol.*, 184(16):4601-11, 2002.

Floss et al., "Production of vaccines and therapeutic antibodies for veterinary applications in transgenic plants: an overview," *Transgenic Research*, 16(3):315-332, 2007.

Heath et al., "Protection against experimental bubonic and pneumonic plague by a recombinant capsular F1-V antigen fusion protein vaccine," *Vaccine*, 16(11/12):1131-7, 1998.

Holt et al., "Domain antibodies: proteins for therapy," *Trends Biotechnol.*, 21(11): 484-490, 2003.

Huber et al., "Distinct contributions of vaccine-induced immunoglobulin G1 (IgG1) and IgG2a antibodies to protective immunity against influenza," *Clin. Vaccine Immunol.*, 13:981-90, 2006.

Huse et al., "Generation of a large combinatorial library of the immunoglobulin repertoire in phage lambda," *Science*, 246:1275, 1989.

Jirholt et al., "Exploiting sequence space: shuffling in vivo formed complementarity determining regions into a master framework," *Gene*, 215:471, 1998.

Jones et al., "Replacing the complementarity-determining regions in a human antibody with those from a mouse," *Nature*, 321:522, 1986.

Kang et al., "Linkage of recognition and replication functions by assembling combinatorial antibody Fab libraries along phage surfaces," *Proc. Natl. Acad. Sci USA*, 88:4363, 1991.

Katayama and Mine, "*Quillaja* saponin can modulate ovalbumin-induced IgE allergic responses through regulation of Th1/Th2 balance in a murine model," *J. Agric. Food Chem.*, 54:3271-6, 2006.

Konieczny et al., "The combination of IgM subunits and proteolytic IgG fragments by controlled formation of interchain disulphides," *Haematologia* (*Budap.*), 14:95, 1981.

Krebber et al., "Reliable cloning of functional antibody variable domains from hybridomas and spleen cell repertoires employing a reengineered phage display system," *J Immunol Methods*, 201:35-55, 1997.

Kubler-Kielb et al., "Long-lasting and transmission-blocking activity of antibodies to *Plasmodium falciparum* elicited in mice by protein conjugates of Pfs25," *Proc. Natl. Acad. Sci. USA*, 104(1): 293-298, 2007.

Lee and Air, "Contacts between influenza virus N9 neuraminidase and monoclonal antibody NC10," *Virology*, 300(2):255-268, 2002.

Li et al., "Immunization with recombinant beta-tubulin from *Trypanosoma evansi* induced protection against *T. evansi, T. equiperdum* and *T. b. brucei* infection in mice," *Parasite Immunology*, 29:191-199, 2007.
Little et al., "Of mice and men: hybridoma and recombinant antibodies," *Immunology Today*, 21(8): 364-370, 2000.

Mbawuike et al., "Humoral and cell-mediated immune responses of humans to inactivated influenza vaccine with or without QS21 adjuvant," *Vaccine*, 25:3263-9, 2007.

Mett et al., "Plants as biofactories," *Biologicals: J. Int. Assoc. Biol. Stand.*, 36(6):354-358, 2008.

Morrison et al., "Chimeric human antibody molecules: Mouse antigen-binding domains with human constant region domains," *Proc. Natl. Acad. Sci USA*, 81:6851, 1984.

Morrison et al., "Production of novel immunoglobulin molecules by gene transfection," *Mt. Sinai J. Med.*, 53:175, 1986.

Parkhill et al., "Genome sequence of *Yersinia pestis*, the causative agent of plague," *Nature*, 413:523-7, 2001.

Pfitzner et al., "Isolation and characterization of cDNA clones encoding pathogenesis-related proteins from tobacco mosaic virus infected tobacco plants," *Nucleic Acids Research*, 15(11):4449-4465, 1987.

Pruett et al., "Critical interactions in binding antibody NC41 to influenza N9 neuraminidase: amino acid contacts on the antibody heavy chain," *Biochem.*, 37:10660-10670, 1998.

Riechmann et al., "Reshaping human antibodies for therapy," *Nature*, 332:323, 1988.
Rowe et al., "Detection of antibody to avian influenza A (H5N1) virus in human serum by using a combination of serologic assays," *J. Clin. Microbiol.*, 37:937-43 , 1999.
Sabbatini et al., "Pilot study of a heptavalent vaccine-keyhole limpet hemocyanin conjugate plus QS21 in patients with epithelial ovarian, fallopian tube, or peritoneal cancer," *Clin. Cancer Res.*, 13:4170-7, 2007.
Saravolac et al. "Immunoprophylactic strategies against respiratory influenza virus infection " *Vaccine*, 19:2227-2232, 2001.
Schild et al., "A single-radial-immunodiffusion technique for the assay of influenza haemagglutinin antigen—Proposals for an assay method for the haemagglutinin content of influenza vaccines," *Bull. World Health Org.*, 52:223-31, 1975.

Shimasaki et al., "Rapid diagnostics: the detection of neuraminidase activity as a technology for high-specificity targets," *Philosophical Transactions of the Royal Society of London. Series B, Biological Sciences*, 356(1416):1925-1931, 2001.
Shoji et al., "Immunogenicity of hemagglutinin from A/Bar-headed/Goose/Qinghai/1A/05 and A/Anhui/1/05 strains of H5N1 influenza viruses produced in *Nicotiana benthamiana* plants," *Vaccine*, 27(25/26): 3467-3470, 2009.
Shoji et al., "Plant-expressed HA as a seasonal influenza vaccine candidate," *Vaccine*, 26(23):2930-2934, 2008.
Soderlind et al., "Commentary—Complementarity-determining region (CDR) implantation: a theme of recombination," *Immunotechnol.*, 4:279, 1999.
Soderlind et al., "Recombining germline-derived CDR sequences for creating diverse singleframework antibody libraries," *Nature Biotechnol.*, 18:852, 2000.
Sweet et al., "Pathogenicity of Influenza Virus," *Microbiolog. Rev.*, 44(2):303-330, 1980.
Throsby et al., "Heterosubtypic neutralizing monoclonal antibodies cross-protective against H5NI and H1N1 recovered from human IgM+ memory B cells," *Plos One*, LNKD-PUBMED:19079604, 3(12):E3942, 2008.
UniProt Database [Online] EBI Accession No. Q0PDN1, "SubName: Full=Hemagglutinin," Sep. 5, 2006.
UniProt Database [Online] EBI Accession No. A9X0E7, "SubName: Full=Hemagglutinin; Flags: Precursor," Feb. 5, 2008.
UniProt Database accession No. P04107 Nov 1, 1986.
Webster et al., "Antigenic structure and variation in an influenza virus N9 neuraminidase," *J. Virology*, 61:2910-2916, 1987.
Williamson et al., "Human immune response to a plague vaccine comprising recombinant F1 and V antigens," *Infect. Immun.*, 73(6):3598-608, 2005.
Williamson et al., "A single dose sub-unit vaccine protects against pneumonic plague," *Vaccine*, 19:566-71, 2000.
Williamson et al., "A new improved sub-unit vaccine for plague: the basis of protection," *FEMS Immunol. Med. Microbiol.*, 12:223-30, 1995.
Winter and Milstein, "Man-made antibodies," *Nature*, 349:293, 1991.
Yang et al., "Production and diagnostic application of monoclonal antibodies against influenza virus H5," *Journal of Virological Methods*, 162(1-2):194-202, 2009.
Yusibov et al., "An influenza N1 neuraminidase-specific monoclonal antibody with broad inactivating activity against H5N1 viruses," *Human Antibodies*, 16(1-2):33, 2007.
Yusibov et al., "An influenza N1 neuraminidase-specific monoclonal antibody protects animal against live challenge with homologous H5N1 virus," *Human Antibodies*, 17(1-2):15, 2008.
Communication dated Apr. 21, 2010 for European Appln. No. 04776107.7 (4 pgs.).
Communication dated May 20, 2010 for European Appln. No. 04776107.7 (3 pgs.).
Communication dated May 19, 2009 for European Appln. No. 06850507.2 (3 pgs.).
Communication dated Feb. 18, 2010 for European Appln. No. 07750905.7 (2 pgs.).
Examiner's First Report dated Aug. 24, 2011 for Australian Appln. No. 2007215082 (3 pgs.).
International Preliminary Report on Patentability dated Apr. 23, 2008 for Int'l. Appln. No. PCT/US06/030545 (9 pgs.).
International Preliminary Report on Patentability dated Mar. 17, 2009 for Int'l. Appln. No. PCT/US07/004103 (5 pgs.).
International Preliminary Report on Patentability dated Nov. 3, 2009 for Int'l. Appln. No. PCT/US08/061782 (7 pgs.).
International Preliminary Report on Patentability dated Mar. 29, 2011 for Int'l. Appln. No. PCT/US09/058640 (7 pgs.).
International Preliminary Report on Patentability dated Mar. 29, 2011 for Int'l. Appln. No. PCT/US09/058669 (12 pgs.).
International Search Report and Written Opinion dated Apr. 4, 2008 for Int'l Appln. No. PCT/US06/030545 (3 pgs.).
International Search Report and Written Opinion dated Aug. 7, 2007 for Int'l. Appln. No. PCT/US07/004103 (9 pgs.).
International Search Report and Written Opinion dated Oct. 21, 2008 for Int'l. Appln. No. PCT/US08/061782 (10 pgs.).
International Search Report and Written Opinion dated May 29, 2009 for Int'l. Appln. No. PCT/US08/069860 (8 pgs.).
International Search Report and Written Opinion dated May 11, 2010 for Int'l Appln. No. PCT/US09/058488 (20 pgs.).
International Search Report and Written Opinion dated Feb. 2, 2010 for Int'l. Appln. No. PCT/US09/058640 (13 pgs.).
International Search Report and Written Opinion dated Jan. 27, 2011 for Int'l. Appln. No. PCT/US10/050693 (7 pgs.).
Notification of Defects in Patent Application dated Sep. 16, 2010 for Israeli Patent Appln. No. 193391 (3 pgs.).
Office Action (restriction requirement) dated Nov. 28, 2007 for U.S. Appl. No. 11/706,573 (8 pgs.).
Office Action (non-final) dated Apr. 16, 2008 for U.S. Appl. No. 11/706,573 (11 pgs.).
Office Action (non-final) dated Jan. 21, 2009 for U.S. Appl. No. 11/706,573 (10 pgs.).
Office Action (non-final) dated Feb. 22, 2010 for U.S. Appl. No. 11/706,573 (11 pgs.).
Office Action (non-final) dated Nov. 24, 2010 for U.S. Appl. No. 11/706,573 (11 pgs.).
Supplementary European Search Report dated Dec. 5, 2006 for European Appln. No. 04776107.7 (2 pgs.).
Supplementary European Search Report dated Oct. 8, 2009 for European Appln. No. 07750950 (5 pgs.).
Accession CAA4959, Apr. 18, 2005.
Ahlquist et al., "Gene Expression Vectors Derived from Plant RNA Viruses", Current Communications in Molecular Biology—Viral Vectors, (Ed., Gluzman et al.) 183-189, 1988.
Akol and Murray, "*Trypanosoma congolense*: Susceptibility of cattle to cyclical challenge," Exp. Parasitol., 55:386-393, 1983.
Alignment of 11706573-6 to SEQ ID No. 6 cited by the Examiner in parent matter U.S. Appl. No. 10/558,109, filed Feb. 24, 2009.

Alignment of 11706573-30 to SEQ ID No. 6 cited by the Examiner in parent matter U.S. Appl. No. 10/558,109, filed Feb. 24, 2009.
Alignment of 11706576-12 to SEQ ID No. 6 cited by the Examiner in parent matter U.S. Appl. No. 10/558,109, filed Feb. 24, 2009.
Alignment of 12110877-30 to SEQ ID No. 6 cited by the Examiner in parent matter U.S. Appl. No. 10/558,109, filed Feb. 24, 2009.
Alvarez et al., "Plant-made subunit vaccine against pneumonic and bubonic plague is orally immunogenic in mice", Vaccine Elsevier Ltd., GB, vol. 24, No. 14, Jan. 13, 2006, pp. 2477-2490.
Ay et al., "Crystal structures and properties of de novo circularly permuted 1,3-1,4-beta-glucanases," Proteins, 30(2): 155-67, Feb. 1, 1998.
Barfield et al., "Gene Transfer in Plants of *Brassica juncea* Using *Agrobacterium tumefaciens*-Mediated Transformation", Plant Cell Reports 1991, 10(6/7): 308-14.
Bates, "Genetic Transformation of Plants by Protoplast Electroporation", Molecular Biotechnol., 1994, 2(2):135-145.
Beachy et al., "A Genetic Map for The Cowpea Strain of TMV" Virology 1976, 73: 498-507.
Bedell et al., "The E6-E7 Region of Human Papillomavirus Type 18 Is Sufficient for Transformation of NIH 3T3 and Rat-1 Cells", J. Virol., 1987, 61:3635-40.
Bisaro et al., "Genetic Analysis of Tomato Golden Mosaic Virsu", Current Communications in Molecular Biology: Viral Vectors, Cold Spring Harbor Laboratory, Cold Spring Harbor, NY, pp. 172-189, 1988.
Bol et al., "A Functional Equivalence of Top Component a RNA and Coat Protein in the Initiation of Infection by Alfalfa Mosaic Virus" Virology 1971, 46: 73-85.
Bol et al., "Alfalfa Mosaic Virus and Ilarviruses: Involvement of Coat Protein in Multiple Steps of the Replication Cycle" J.. Gen. Virol. 1999, 80: 1089-1102.
Boyd, M. R. and Beeson, M. F., "Animal models for evaluation of compounds against influenza viruses", Journal of Antimicrobial Chemotherapy, (1975) 1 (Suppl.), 43-47.
Brett et al., "Immunization against influenza A virus: comparison of conventional inactivated, live-attenuated and recombinant baculovirus produced purified hemagglutinin and neuraminidase vaccines in a murine model system", Virology, vol. 339, No. 2, Sep. 1, 2005, pp. 273-280.
Broothaerts et al. (2005), Nature, 433:629-33.
Bruening et al., "In Vitro and In Vivo Translation of the Ribonucleic Acids of a Cowpea Strain of Tobacco Mosaic Virus" Virology 1976, 71: 498-517.
Buscaglia et al., "Tandem amino acid repeats from *Trypanosoma cruzi* shed antigens increase the half-life of proteins in blood", Blood, vol. 93(6), pp. 2025-2032, Mar. 15, 1999.
Calandrelli et al., "Purification and characterization of thermostable eylanase and beta-xylosidase by the termophilic bacterium *Bacillus termantarcticus*," Res. Microbiol., 155(4): 283-9, 2004.
Canizares et al., "Use of viral vectors for vaccine production in plants", Immunol Cell Biol., 2005, 83:263-270.
Chen et al., "Complete sequence of the binary vector pB1121 and its application in cloning T-DNA insertion from transgenic plants", *Mol. Breed.*, 2003, 11, 287-293.
Chen et al., "Induction and relief of nasal congestion in ferrets infected with influenza virus", Int. J. Exp. Path., (1995), 76, pp. 55-64.
Chica et al., "Semi-rational approaches to engineering enzyme activity: combining the benefits of directed evolution and rational design," Current Opinion in Biotechnology, 16:378-384, 2005.
Chichester et al., "Immunogenicity of a subunit vaccine against *Bacillus anthracis*", Vaccine, 2007, 25:3111-3114.
Corbel, M. J., "Reasons for instability of bacterial vaccines",*Developments in Biological Standardization*, vol. 87, pp. 113-124, 1996.
Costa et al., "Conformational stability and antibody response to the 18kDa heat-shock protein formulated into different vehicles", *Applied Biochemistry and Biotechnology*, vol. 73(1), pp. 19-28, Apr. 1998.
Crossway, A., et al., "Integration of foreign DNA following microinjection of tobacco mesophyll protoplasts"Mol. Gen. Genet., 1986, 202:179-185.

Curtis and Nam, "Transgenic radish (*Raphanus sativus* L. longipinnatus Bailey) by floral-dip method—plant development and surfactant are important in optimizing transformation efficiency", Transgenic Research, 2001, 10(4):363-371.
Dawson et al., "cDNA cloning of the complete genome of tobacco mosaic virus and production of infectious transcripts", Proc. Natl Acad. Sci., USA, 1986, 83:1832.
DeGraff, et al., "In Vitro Evidence That the Coat Protein of Alfalfa Mosaic Virus Plays a Direct Role in the Regulation of Plus and Minus RNA Synthesis Implications for the Life Cycle of Alfalfa Mosaic Virus" Virology 1995, 208: 583-589.
Desfeux et al., "Female Reproductive Tissues Are the Primary Target of *Agrobacterium*-Mediated Transformation by the *Arabidopsis* Floral-Dip Method", Plant Physiology, 2000, 123(3):895-904.
Dréau et al., "Human Papilloma Virus in Melanoma Biopsy Specimens and Its Relation to Melanoma Progression", Annals of Surgery, 2000, 231:664-671.
Fenton et al., "Immunity to Influenza in Ferrets. XIV: Comparative Immunity Following Infection or Immunization With Live or Inactivated Vaccine", *Br. J. exp. Path.*, (1981) 62, 297.
Fernando et al., "Expression, purification and immunological characterization of the transforming protein E7, from cervical cancer-associated human papillomavirus type 16", *Clin Exp Immunol*, 1999, 115:397-403.
Flick-Smith et al., "A Recombinant Carboxy-Terminal Domain of the Protective Antigen of *Bacillus anthracia* Protects Mice against Anthrax Infection", *Infect. Immun.*, 2002, 70:1653-1656.
Fraley et al., "Expression of Bacterial Genes in Plant Cells" Proc. Natl. Acad. Sci. USA 1983, 80: 4803-4807.
Fraley et al., "Liposome-Mediated Delivery of Tobacco Mosaic Virus RNA Into Tobacco Protoplasts: A Sensitive Assay for Monitoring Liposome-Protoplast Interactions" Proc. Natl. Acad. Sci. USA 1982, 79: 1859-1863.
Franconi et al., "Plant-derived Human Papillomavirus 16 E7 Oncoprotein Induces Immune Response and Specific Tumor Production", Cancer Res., 2002, 62:3654.
Fromm et al., "Expression of Genes Transferred Into Monocot and Dicot Plant Cells by Electroporation" Proc. Natl. Acad. Sci. USA 1985, 82: 5824, 1985.
Fütterer et al., "Use of DNA Plant Viruses and Plant Viral Expression Signals for Gene Expression in Plants and Plant Protoplasts", Current Communications in Molecular Biology—Viral Vectors, (Ed., Gluzman et al.) 1988, 178-182.
Gelvin, "*Agrobacterium*-Mediated Plant Transformation: the Biology behind the 'Gene-Jockeying' Tool", Microbiol. Mol Biol. Rev., 2003, 67(1):16-37.
Giri and Narasu, "Transgenic hairy roots: recent trends and applications", Biotechnol. Adv., 2000, 18:1-22.
Gleba et al., "Magnifection—a new platform for expressing recombinant vaccines in plants", Vaccine, 2005, 23:2042-2048.
Goldenkova et al., "A Thermostable *Clostridium thermocellum* Lichenase-based Reporter System for Studying the Gene Expression Regulation in Prokaryotic and Eukaryotic Cells", Mol. Biol., 2002, 36:698-704.
Green et al., "Transient protein expression in three *Pisum sativum* (green pea) varieties", Biotechnology Journal, vol. 4, No. 2, Feb. 2009, pp. 230-237.
Grierson et al., "Plant Viruses", Plant Molecular Biology, Blackie, London, pp. 126-146, 1984.
Gu et al., "Protection against anthrax toxin by vaccination with a DNA plasmid encoding anthrax protective antigen", Vaccine, 1999, 17:340.
Hahn et al., "Native-like in-vivo folding of a circularly permuted jellyroll protein shown by crystal structure analysis", Proc. Natl. Acad. Sci., USA, 1994, 91(22):10417-10421.
Hellens et al., "pGreen: a versatile and flexible binary Ti vector for *Agrobacterium*- mediated plant transformation" Plant Molecular Biology 2000, 42: 819-832.
Herbert and Lumsden, "*Trypanosoma brucei*: A rapid 'matching' method for estimating the host's parasitemia," Exp. Parasitol, 40:427, 1976.

Hobson et al., "The role of serum haemagglutination-inhibiting antibody in protection against challenge infection with influenza A2 and B viruses", *J. Hyg.*, 1972, 70:767.

Huang et al., "Plant-derived measles virus hemagglutinin protein induces neutralizing antibodies in mice", *Vaccine*, Feb. 28, 2001, vol. 19, No. 15-16, pp. 2163-2171.

Hull et al., "Human-derived, plant-produced monoclonal antibody for the treatment of anthrax", *Vaccine*, 2005, 23:2082-2086.

Hunter et al., "Messenger RNA for the Coat Protein of Tobacco Mosaic Virus" Nature 1976, 260: 759-760.

Ishikawa et al., "In Vitro Mutagenesis of the Putative Replicase Genes of Tobacco Mosaic Virus" Nucleic Acids Res. 1986, 14: 8291-8308.

Jaspars et al., "Plant Viruses With a Multipartite Genome" Adv. Virus Res. 1974, 19: 37-149.

Johnson et al., Respiratory syncytial virus (RSV) G glycoprotein is not necessary for vaccine-enhanced disease induced by immunization with formalin-inactivated RSV, J. Virol, 78(11):6024-32, 2004.

Kao et al., "A Method for High-frequency Intergeneric Fusion of Plant Protoplasts", Planta, 1974, 115:355.

Kapila et al., "An *Agrobacterium*-mediated transient gene expression system for intact leaves", Plant Sci., 1997, 122:101-108.

Kapusta et al., "A plant-derived edible vaccine against hepatitis B virus", FASEB J., 1999, 13:1796-1799.

Kikkert et al., "Biological Projectiles (Phage, Yeast, Bacteria) for Genetic Transformation of Plants", In Vitro Cell. Dev. Bio.—Plant, 1999. 35(1):43-50.

Klein et al., "High-velocity microprojectiles for delivering nucleic acids into living cells", Nature, 1987, 327:70-73.

Knapp et al., "Conundrum of the Lack of Defective RNAs (dRNAs) Associated with Tobamovirus Infections: dRNAs That Can Move Are Not Replicated by the Wild-Type Virus; dRNAs That Are Replicated by the Wild-Type Virus Do Not Move", J. Virol., 2001, 75:5518.

Knudsen and Muller, "Transformation of the developing barley endosperm by particle bombardment", Planta, 1991, 185:330-336.

Krens et al., "In vitro transformation of plant protoplasts with Ti-plasmid DNA", Nature, 1982, 296:72-74.

Kubler-Kielb, J. et al., "Long-lasting and transmission-blocking activity of antibodies to *Plasmodium falciparum* elicited in mice by protein conjugates of Pfs25", Proceedings of the National Academy of Sciences of USA, vol. 104, No. 1, Jan. 1, 2007, pp. 293-298.

Kumagai, et al., "Rapid, High-Level Expression of Glycosylated Rice α-Amylase in Transfected Plants by an RNA Viral Vector" Gene 2000, 245: 169-174.

Lambkin et al., "Strong local and systemic protective immunity induced in the ferret model by an intranasal virosome-formulated influenza subunit vaccine", Vaccine, 2004, 22:4390.

Lawton et al., "Expression of a Soybean (3-Conclycinin Gene Under the Control of the Cauliflower Mosaic Virus Virus 35S and 19S Promoters in Transformed *Petunia* Tissues" Plant Mol. Biol 1987, 9: 315-324.

Leite et al., "Expression of correctly processed human growth hormone in seeds of transgenic tobacco plants", Molecular Breeding, 2000, 6: 47-53.

Lensen, A. et al., "Measurement by membrane feeding of reduction in *Plasmodium falciparum* transmission induced by endemic sera", Trans R Soc Trop Med Hyg. Jan.-Feb. 1996;90(1):20-2.

Lewandowski and Dawson, "Deletion of Internal Sequences Results in Tobacco Mosaic Virus Defective RNAs That Accumulate to High Levels without Interfering with Replication of the Helper Virus", Virology, 1998, 251:427-437.

Lim et al., "An Anthrax Lethal Factor-Neutralizing Monoclonal Antibody Protects Rats before and after Challenge with Anthrax Toxin", *Infection and Immunity*, 2005, 73:6547.

Lin et al., "Treatment of Established Tumors with a Novel Vaccine That Enhances Major Histocompatibility Class II Presentation of Tumor Antigen", *Cancer Research*, 1996, 56:21.

Little et al., "Passive Protection by Polyclonal Antibodies against *Bacillus anthracis* Infection in Guinea Pigs", *Infect. Immun.*, 1997, 65:5171-5175.

Loesch-Fries, et al., "Expression of Alfalfa Mosaic Virus RNA 4 cDNA Transcripts In Vitro and In Vivo" Virology 1985, 146: 177-187.

Lorence and Verpoorte (2004), Methods Mol. Biol., 267:329-50.

Lubega et al., "Immunization with a tubulin-rich preparation from *Trypanosoma brucei* confers broad protection against African trypanosomosis," *Exp. Parasitol.*, 2002, 102:9-22.

Lubega et al., "*Trypanosoma brucei*: anti-tubulin antibodies specifically inhibit trypanosome growth in culture," *Exp. Parasitol.*, 2002, 102:134-142.

Maliga et al., "Transient Cycloheximide Resistance in a Tobacco Cell Line", *Mol. Gen. Genet.*, 1976, 149, 267-271.

Maassab et al., "Evaluation of a Cold-Recombinant Invluenza Virus Vaccine in Ferrets", *The Journal of Infectious Diseases*, vol. 146, No. 6, Dec. 1982, pp. 780-790.

Mathew, Plant Viruses Online—Cassava Indian mosaic bigeminvirus (http://imagels.uidaho.eduivide/), downloaded on Feb. 21, 2006, 5 pgs.

McCormick et al., "Rapid Production of Specific Vaccines for Lymphoma by Expression of the Tumor-Derived Single-Chain Fv Epitopes in Tobacco Plants" Proc. Natl. Acad. Sci. USA 1999, 96: 703-708.

McHugh et al., "Improved stability of a protein vaccine through elimination of a partially unfolded state", *Protein Science*, 2004, vol. 13, pp. 2736-2743.

Mellin et al., "Human Papillomavirus (HPV) DNA in Tonsillar Cancer: Clinical Correlates, Rise of Relapse, and Survival", *International Journal of Cancer*, 2000, 89:300-304.

Menczel et al. "Streptomycin Resistant and Sensitive Somatic Hybrids of *Nicotiana tabacum* + *Nicotiana knightiana*: Correlation of Resistance to *N. tabacum* Plastids", *Theor. Appl. Genet.*, 1981, 59, 191-195.

Meshi et al., "Function of the 30 kd Protein of Tobacco Mosaic Virus: Involvement in Cell-To-Cell Movement and Dispensability for Replication" EMBO J. 1987, 6: 2557-63.

Mett, V., et al., "A plant-produced plague vaccine candidate confers protection to monkeys", *Vaccine*, Apr. 20, 2007, vol. 25, No. 16, pp. 3014-3017.

Mett, V., et al., "A plant-produced influenza subunit vaccine protects ferrets against virus challenge", *Influenza and Other Respiratory Viruses*, Jan. 2008, vol. 2, No. 1, pp. 33-40.

Moayeri et al., "The roles of anthrax toxin in pathogenesis," Curr Opin Michrobiol, 7(1):19-24, 2004.

Modelska et al., "Immunization against rabies with plant-derived antigen", Proc. Nati. Acad. Sci., USA, 1998, 95:2481-2485.

Moreira et al., "A Thermostable Maltose-tolerant α-anylase from *Asperillgus tamarii*," J. Basic Microbiology, 44: 29-35, 2004.

Murashige et al., "A Revised Medium for Rapid Growth and Bio Assays with Tobacco Tissue Cultures", Physiologia Plantarum, 1962, 15:473.

Musiychuk et al., "A launch vector for the production of vaccine antigens in plants", Influenza and Other Respiratory Viruses, 2007, 1:1.

Musiychuk et al., Preparation and properties of *Clostribdium termocellum* lichenase deletion variants and their use for construction of bifunctional hybrid proteins, Biochemistry Mosc., (65(12): 1397-402, Dec. 2000.

Nagy et al., Thermal stability of chemically denatured green fluorescent protein (GFP)—A preliminary study, 2004, Thermochimica Acta, vol. 410, No. 1, abstract.

Nass, "Anthrax Vaccine—Model of a Response to the Biologic Warfare Threat", Infect. Dis. Clin. North Am., 1999, 13,187-208.

NCBI GenBank Accession No. ABP96852, "Influenza A virus" (A/Egypt/2616-NAMRU3/2007(H5N1)) hemagglutinin (HA) gene, complete CDS, Apr. 30, 2007.

NCBI GenBank Accession No. AAS93885, "Influenza A virus" (A/Cheju/274/2002(H3N2)) neuraminidase (NA) gene, complete CDS, Apr. 25, 2004.

Neeleman et al., "Role of Alfalfa Mosaic Virus Coat Protein Gene in Symptom Formation" *Virology* 1991 181: 687-693.

Neeleman et al., "Infection of Tobacco With Alfalfa Mosaic Virus cDNAs Sheds Light on the Early Function of the Coat Protein" *Virology* 1993, 196: 883-887.

Park et al., "Molecular Biology of Cervical Cancer and Its Precursors", Cancer, 1995, 76:1902-1913.

Peres et al., 2001, "Shoot regeneration capacity from roots and transgenic hairy roots of tomato cultivars and wild related species", Plant Cell, Tissue, and Organ Culture, 2001, 65:37-44.

Petosa et al., "Crystal structure of the anthrax toxin protective antigen", Nature, 1997, 385:833-838.

Pilon-Smits et al., "Overexpression of ATP Sulfurylase in Indian Mustard Leads to Increased Selenate Uptake, Reduction, and Tolerance" Plant Physiol. 1999, 119(1): 123-132.

Piruzian et al., "A reporter system for prokaryotic and eukaryotic cells based on the thermostable lichenase from *Clostridium thermocellum*," Mol Genet Genomics, 266(5): 778-86, Jan. 2002, Epub Nov. 27, 2001.

Piruzian et al., "The use of a thermostable B-glucanase gene from *Clostridium thermocellum* as a reporter gene in plants," Mol Gen Genet 257(50): 561-7, Mar. 1998.

Potter et al., "Immunity to Influenza in Ferrets II. Influence of Adjuvants on Immunization", *Br. J. Exp. Pathol.*, 1972, 53:168.

Potter et al., "Immunity to Influenza in Ferrets VI. Immunization with Adjuvanted Vaccines", *Arch. Gesamte Virusforsch.*, 1973, 42:285.

Potter et al., "Immunity to influenza in ferrets V. Immunization with inactivated virus in adjuvant 65", *J. Hyg. Lond.*, 1973, 71:97.

Qian et al., "Conjugating recombinant proteins to *Pseudomonas aeruginosa* ExoProtein A: A strategy for enhancing immunogenicity of malaria vaccine candidate", Vaccine, vol. 25, No. 20, Apr. 24, 2007, pp. 3923-3933.

Qing et al., "Transformation of Pakchoi (*Brassica rapa* L. ssp. chinensis) by *Agrobacterium* Infiltration", Molecular Breeding, 2000, 1:67-72.

Rao and Ravishankar, "Plant cell cultures: Chemical factories of secondary metabolites", Biotechnol. Adv., 2002, 20:101-153.

Rasooly-Balaban, "Trypanosome microtubule-associated protein p15 as a vaccine for the prevention of African sleeping sickness", Vaccine, vol. 22, No. 8, Feb. 25, 2004, pp. 1007-1015.

Reinstein et al., Degradation of the E7 human papillomavirus oncoprotein by the ubiquitin-proteasome system: targeting via ubiquitination of the N-terminal residue, Oncogene, 2000, 19, 5944-5950.

Riva et al., "*Agrobacterium tumefaciens*: a natural tool for plant transformation", EJB Electronic J. Biotech., 1998, 1(3), 118-133.

Saito, et al., "Long-Distance Movement and Viral Assembly of Tobacco Mosaic Virus Mutants" Virology 1990, 176: 329-336.

Santi, V., et al., "Protection conferred by recombinant *Yersinia pestis* antigens produced by a rapid and highly scalable plant expression system", Proc. Natl. Acad. Sci. USA, Jan. 24, 2006, vol. 103, No. 4, pp. 861-866.

Scheiblauer et al., "Pathogenicity of influenza A/Seal/Mass/1/80 virus mutants for mammalian species", Arch Virol, (1995), 140: 341-384.

Schell et al., "Transgenic Plants As Tools to Study the Molecular Organization of Plant Genes." Science 1987, 237: 1176-1186.

Seedorf et al., "Human Papillomavirus Type 16 DNA Sequence", Virology, 1985, 145:181.

Sen et al., Appl Biochem Biotechnol., 143(3):212-23, Dec. 2007.

Shima et al., "hyperthermaphilic and salt-dependent formytransferase from *Methanopyrus kanleri*," Biochem Soc. Trans., 32:269-72, 2004.

Shivprasad et al., "Heterologous Sequences Greatly Affect Foreign Gene Expression in Tobacco Mosaic Virus-Based Vectors", Virology, 1999, 255(2):312-23.

Singh et al., "Gln277 and Phe544 residues are involved in thermal inactivation of protective antigen of *Bacillus anthracis*", *Biochemical and Biophysical Research Communications*, 2002, vol. 296, pp. 1058-1062.

Singh et al., "Study of Immunization against Anthrax with the Purified Recombinant Protective Antigen of *Bacillus anthracis*", *Infect. Immun.*, 1998, 66, 3447-3448.

Singh et al., "Thermal inactivation of protective antigen of *Bacillus anthracis* and its prevention by polyol osmolytes", *Biochemical and Biophysical Research Communications*, 2004, vol. 322, pp. 1029-1037.

Smahel et al., "Modified HPV16 E7 Genes as DNA Vaccine against E7-Containing Oncogenic Cells", Virology, 281, 231-238 (2001).

Snow et al, 2005, Nature, 434:214-7.

Soini et al., "Presence of human papillomavirus DNA and abnormal p53 protein accumulation in lung carcinoma", Thorax, 1996, 51:887-893.

Spilliaert et al., "Cloning and sequencing of a *Rhodothermus marinus* gene, bglA, coding for a thermostable beta-glucanase and its expression in *Escherichia coli*", Eur. J. Biochem., vol. 224(3):923-930, Sep. 15, 1994.

Stewart et al., "Mutant barley $(1 \rightarrow 3, 1 \rightarrow 4)$-$\beta$-glucan endohydrolases with enhanced thermostability", Protein Engineering, vol. 14, No. 4, pp. 245-253, (2001).

Tacket et al., "Human Immune Responses to a Novel Norwalk Virus Vaccine Delivered in Transgenic Potatoes", J. Infect. Dis., 2000, 182:302-305.

Thanavala et al., "Immunogenicity in humans of an edible vaccine for hepatitis B", Proc. Natl. Acad. Sci., USA, 2005, 102:3378-3382.

The World Health Organization Global Influenza Program Surveillance Network, Evolution of H5N1 Avian Influenza Viruses in Asia, 2005, Emerging Infectious Diseases, vol. 11, No. 10, pp. 1515-1521.

Thomas et al., "HPV-18 E6 mediated inhibition of p53 DNA binding activity is independent of E6 induced degradation", Oncogene, 1995, 10:261-8.

Toms et al., "Behaviour in Ferrets of Swine Influenza Virus Isolated from Man", *The Lancet*, Jan. 8, 1977, pp. 68-71.

Tsai et al., "Crystal structure of a natural circularly permuted jellyroll protein: 1,3-1,4-beta-D-glucanase from Fibrobacter succinogens," J Mol Biol., 330(3):607-20, Jul. 11, 2003.

Turpen et al., "Transfection of whole plants from wounds inoculated with *Agrobacterium tumefaciens* containing cDNA of tobacco mosaic virus", J. Virol, Methods, 1993, 42:227.

Van der Kolk, M. et al., Parasitology, Jan. 2005; 130(Pt 1): 13-22 (with Erratum in: Parasitology Oct. 2005; 131(Pt 4):578.

Van Der Kuyl et al., "Complementation and Recombination between Alfalfa Mosaic Virus RNA3 Mutants in Tobacco Plants", *Virology*, 1991, 183:731-738.

Van Der Kuyl et al., "Role of Alfalfa Mosaic Virus Coat Protein in Regulation of the Balance between Viral Plus and Minus Strand RNA Synthesis" *Virology*, 1991, 185:496-499.

Van Der Vossen, et al., "Early and Late Functions of Alfalfa Mosaic Virus Coat Protein Can Be Mutated Separately" Virology 1994, 202: 891-903.

Verch et al., "Expression and assembly of a full-length monoclonal antibody in plants using a plant virus vector", J. Immunol Methods, 1998, 220, 69-75.

Voinnet et al. (2003) Plant J. 33:949-56.

Volten-Doting, Plant Viruses Online (http://image.fs.uidaho.edu/vide/descr009.htm) (downloaded May 18, 2002) (11 pgs.).

Wagner et al., "Plant virus expression systems for transient production of recombinant allergens in *Nicotiana benthamiana*", Methods: A Companion to Methods in Enzymology, vol. 32, No. 3, Mar. 1, 2004; pp. 228-232.

Wang et al., "Immunogenicity of *Plasmodium yoelii* merozoite surface protein 4/5 produced in transgenic plants", International Journal of Parasitology, vol. 38, No. 1, Dec. 22, 2007 pp. 103-110.

Wang et al., "Structural Basis for Thermostability of $\beta$-Glycosidase from the Thermophilic Eubacterium Thermus Nonproteolyticus HG102," J. Bacteriology, 185: 4248-55, 2003.

Webster et al., "Measles virus hemagglutinin protein expressed in transgenic lettuce induces neutralizing antibodies in mice following mucosal vaccination", *Vaccine*, Apr. 24, 2006, vol. 24, No. 17, pp. 3538-3544.

Webster et al., "Protection of ferrets against influenza challenge with a DNA vaccine to the haemagglutinin", *Vaccine*, (1994), vol. 12, No. 16, pp. 1495-1498.

Wiesmuller et al., "Peptid Vaccines and Peptide Libraries," Biol Chem., 382(4): 571-9, Apr. 2001.

Wilson et al., "Structure of the haemagglutinin membrane glycoprotein of influenza virus at 3 Å resolution", Nature, 1981, 289:366.

Woo, P. T. K., "The Haematocrit Centrifuge Technique for the Diagnosis of African Trypanosomiasis", Acta Tropica, 27:384, 1970.

Yusibov et al., "Expression in plants and immunogenicity of plant virus-based experimental rabies vaccine" Vaccine, 2002, 20:3155-3164.

Yusibov et al., "Antigens Produced in Plants by Infection With Chimeric Plant Viruses Immunize Against Rabies Virus and HIV-1" Proc. Natl. Acad. Sci. USA 1997, 94: 5784-5788.

Yusibov, et al., "Functional Significance of Three Basic N-Terminal Amino Acids of Alfalfa Mosaic Virus Coat Protein" Virology 1998, 242: 1-5.

Yusibov et al., "N-Terminal Basic Amino Acids of Alfalfa Mosaic Virus Coat Protein Involved in the Initiation of Infection" Virology 1995 208: 405-407.

Yusibov et al., "Purification, characterization, assembly and crystallization of assembled alfalfa mosaic virus coat protein expressed in *Escherichia coli*", J. Gen. Virol., 1996, 77:567-573.

Zumbach et al., "Antibodies Against Oncoproteins E6 and E7 of Human Papillomavirus Types 16 and 18 in Patients with Head-and-Neck Squamous-Cell Carcinoma", International Journal of Cancer, 2000, 85:815-818.

Advisory Action dated Jan. 15, 2010 for U.S. Appl. No. 11/706,568 (3 pgs.).

Communication corresponding to European Appln. No. 04 776 107.7 date Sep. 23, 2009.

International Preliminary Report on Patentability dated Aug. 19, 2008 for Int'l. Appln. No. PCT/US07/003948 (6 pgs.).

International Preliminary Report on Patentability dated Aug. 19, 2008 for Int'l. Appln. No. PCT/US07/003973 (6 pgs.).

International Preliminary Report on Patentability dated Aug. 19, 2008 for Int'l. Appln. No. PCT/US07/003969 (6 pgs.).

International Preliminary Report on Patentability dated Jan. 12, 2010 for International Appln. No. PCT/US2008/069860 (5 pgs.).

International Preliminary Report on Patentability dated Mar. 4, 2010 for Int'l. Appln. No. PCT/US08/073776 (6 pgs.).

International Preliminary Report on Patentability dated Mar. 29, 2011 for Int'l. Appln. No. PCT/US2009/058669 (12 pgs.).

International Search Report and Written Opinion dated Aug. 3, 2007 for Int'l. Appln. No. PCT/US07/003973 (9 pgs.).

International Search Report and Written Opinion dated Jun. 18, 2008 for Int'l. Appln. No. PCT/US07/003948 (9 pgs.).

International Search Report and Written Opinion dated Sep. 4, 2007 for Int'l. Appln. No. PCT/US07/003969 (10 pgs.).

International Search Report and Written Opinion dated Apr. 24, 2009 for Int'l. Appln. No. PCT/US08/073776 (11 pgs.).

International Search Report, PCT/US04/16452, date of mailing Dec. 23, 2005.

International Search Report and Written Opinion dated May 29, 2009 for International Appln. No. PCT/US2008/069860 (8 pgs.).

International Search Report and Written Opinion dated May 19, 2010 for International Appln. No. PCT/US2009/058669 (20 pgs.).

Office Action (non-final) dated Nov. 4, 2008 for U.S. Appl. No. 11/706,568 (7 pgs.).

Office Action (non-final) dated Jan. 6, 2009 for U.S. Appl. No. 11/706,568 (8 pgs.).

Office Action (final) dated Jul. 15, 2009 for U.S. Appl. No. 11/706,568 (7 pgs.).

Supplementary European Search Report dated May 5, 2010 for European Appln. No. EP 07750784 (8 pgs.).

Supplementary European Search Report dated Jun. 9, 2010 for European Appln. No. EP 08 78 0572 (5 pgs.).

\* cited by examiner

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
|ABX88711.1|118|F|M|A|V|M|H|F|S|L|T|A|D|R|H|D|D|D|H|L|K|V|H|V|D|S|M|N|H|G|
|CAB54908.1|118|F|M|A|V|M|H|F|S|L|T|A|D|R|H|D|D|D|H|L|K|V|H|V|D|S|M|N|H|G|
|ABF48194.1|117|F|M|A|V|M|H|F|S|L|T|A|D|R|H|D|D|D|H|L|K|V|H|V|D|S|M|N|H|G|
|ABF48193.1|118|F|M|A|V|M|H|F|S|L|T|A|D|R|H|D|D|D|H|L|K|V|H|V|D|S|M|N|H|G|
|ABF48192.1|118|F|M|A|V|M|H|F|S|L|T|A|D|R|H|D|D|D|H|L|K|V|H|V|D|S|M|N|H|G|
|ABF48191.1|118|F|M|A|V|M|H|F|S|L|T|A|D|R|H|D|D|D|H|L|K|V|H|V|D|S|M|N|H|G|
|ABF48190.1|118|F|M|A|V|M|H|F|S|L|T|A|D|R|H|D|D|D|H|L|K|V|H|V|D|S|M|N|H|G|
|ABF48189.1|118|F|M|A|V|M|H|F|S|L|T|A|D|R|H|D|D|D|H|L|K|V|H|V|D|S|M|N|H|G|
|NP_395165.1|118|F|M|A|V|M|H|F|S|L|T|A|D|R|H|D|D|D|H|L|K|V|H|V|D|S|M|N|H|G|
|YP_001293940.1|118|F|M|A|V|M|H|F|S|L|T|A|D|R|H|D|D|D|H|L|K|V|H|V|D|S|M|N|H|G|
|NP_857946.1|118|F|M|A|V|M|H|F|S|L|T|A|D|R|H|D|D|D|H|L|K|V|H|V|D|S|M|N|H|G|
|NP_857751.1|118|F|M|A|V|M|H|F|S|L|T|A|D|R|H|D|D|D|H|L|K|V|H|V|D|S|M|N|H|G|
|ABR68791.1|118|F|M|A|V|M|H|F|S|L|T|A|D|R|H|D|D|D|H|L|K|V|H|V|D|S|M|N|H|G|
|ABR68790.1|118|F|M|A|V|M|H|F|S|L|T|A|D|R|H|D|D|D|H|L|K|V|H|V|D|S|M|N|H|G|
|ABR68789.1|118|F|M|A|V|M|H|F|S|L|T|A|D|R|H|D|D|D|H|L|K|V|H|V|D|S|M|N|H|G|
|ABR68788.1|118|F|M|A|V|M|H|F|S|L|T|A|D|R|H|D|D|D|H|L|K|V|H|V|D|S|M|N|H|G|
|ABR14856.1|118|F|M|A|V|M|H|F|S|L|T|A|D|R|H|D|D|D|H|L|K|V|H|V|D|S|M|N|H|G|
|AAC69799.1|118|F|M|A|V|M|H|F|S|L|T|A|D|R|H|D|D|D|H|L|K|V|H|V|D|S|M|N|H|G|
|AAC62574.1|118|F|M|A|V|M|H|F|S|L|T|A|D|R|H|D|D|D|H|L|K|V|H|V|D|S|M|N|H|G|
|AAF64077.1|118|F|M|A|V|M|I|F|S|L|T|A|D|R|H|D|D|D|H|L|K|V|H|V|D|S|M|N|H|G|
|A4TSQ1.1|118|F|M|A|V|M|H|F|S|L|T|A|D|R|H|D|D|D|H|L|K|V|H|V|D|S|M|N|H|G|
|YP_001004069.1|118|F|M|A|V|M|H|F|S|L|T|A|D|R|H|D|D|D|H|L|K|V|H|V|D|S|M|N|H|G|
|CAL10039.1|118|F|M|A|V|M|H|F|S|L|T|A|D|R|H|D|D|D|H|L|K|V|H|V|D|S|M|N|H|G|
|P23994.1|118|F|M|A|V|M|H|F|S|L|T|A|D|R|H|D|D|D|H|L|K|V|H|V|D|S|M|N|H|G|
|AAA27645.1|118|F|M|A|V|M|H|F|S|L|T|A|D|R|H|D|D|D|H|L|K|V|H|V|D|S|M|N|H|G|
|AAF64076.1|118|F|M|A|V|M|H|F|S|L|T|A|D|R|H|D|D|D|H|L|K|V|H|V|D|S|M|N|H|G|
|YP_636823.1|118|F|M|A|V|I|H|F|S|L|T|A|D|R|H|D|D|D|H|L|K|V|H|V|D|S|M|N|H|G|
|ABG16274.1|118|F|M|A|V|M|H|F|S|L|T|A|D|R|H|D|D|D|H|L|K|V|H|V|D|S|M|N|H|G|
|ABP42325.1|118|F|M|A|V|M|H|F|S|L|T|A|D|R|H|D|D|D|H|L|K|V|H|V|D|S|M|N|H|G|
|YP_001154615.1|118|F|M|A|V|M|H|F|S|L|T|A|D|R|H|D|D|D|H|L|K|V|H|V|D|S|M|N|H|G|
|ABB16313.1|118|F|M|A|V|M|H|F|S|L|T|A|D|R|H|D|D|D|H|L|K|V|H|V|D|S|M|N|H|G|
|YP_001874676.1|121|F|M|A|V|M|H|F|S|L|T|A|D|R|H|D|D|D|H|L|K|V|H|V|D|S|M|N|H|G|
|ACC91219.1|118|F|M|A|V|M|H|E|S|L|T|A|D|R|H|D|D|D|H|L|K|V|H|V|D|S|M|N|H|G|
|ABI97154.1|118|F|M|A|V|M|H|F|S|L|T|A|D|R|H|D|D|D|H|L|K|V|H|V|D|S|M|N|H|G|
|lcrV.pro|118|F|M|A|V|M|H|F|S|L|T|A|D|R|H|D|D|D|H|L|K|V|H|V|D|S|M|N|H|G|

| | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|
| ABX88711.1 | R | Q | M | V | S | D | Y | K | Q | H | F | R | N | L | A | E | H | A | S | N | F | R | S | T | H | D | S | L | Q | T | 289 |
| CAB54908.1 | R | Q | M | V | S | D | Y | K | Q | H | F | R | N | L | A | E | H | A | S | N | F | R | S | T | H | D | S | L | Q | T | 289 |
| ABF48194.1 | R | Q | M | V | S | D | Y | K | Q | H | F | R | N | L | A | E | H | A | S | N | F | R | S | T | H | D | S | L | Q | T | 289 |
| ABF48193.1 | R | Q | M | V | S | D | Y | K | Q | H | F | R | N | L | A | E | H | A | S | N | F | R | S | T | H | D | S | L | Q | T | 289 |
| ABF48192.1 | R | Q | M | V | S | D | Y | K | Q | H | F | R | N | L | A | E | H | A | S | N | F | R | S | T | H | D | S | L | Q | T | 289 |
| ABF48191.1 | R | Q | M | V | S | D | Y | K | Q | H | F | R | N | L | A | E | H | A | S | N | F | R | S | T | H | D | S | L | Q | T | 289 |
| ABF48190.1 | R | Q | M | V | S | D | Y | K | Q | H | F | R | N | L | A | E | H | A | S | N | F | R | S | T | H | D | S | L | Q | T | 289 |
| ABF48189.1 | R | Q | M | V | S | D | Y | K | Q | H | F | R | N | L | A | E | H | A | S | N | F | R | S | T | H | D | S | L | Q | T | 289 |
| NP_395165.1 | R | Q | M | V | S | D | Y | K | Q | H | F | R | N | L | A | E | H | A | S | N | F | R | S | T | H | D | S | L | Q | T | 289 |
| YP_001293940.1 | R | Q | M | V | S | D | Y | K | Q | H | F | R | N | L | A | E | H | A | S | N | F | R | S | T | H | D | S | L | Q | T | 289 |
| NP_857946.1 | R | Q | M | V | S | D | Y | K | Q | H | F | R | N | L | A | E | H | A | S | N | F | R | S | T | H | D | S | L | Q | T | 289 |
| NP_857751.1 | R | Q | M | V | S | D | Y | K | Q | H | F | R | N | L | A | E | H | A | S | N | F | R | S | T | H | D | S | L | Q | T | 289 |
| ABR68791.1 | R | Q | M | V | S | D | Y | K | Q | H | F | R | N | L | A | E | H | A | S | N | F | R | S | T | H | D | S | L | Q | T | 289 |
| ABR68790.1 | R | Q | M | V | S | D | Y | K | Q | H | F | R | N | L | A | E | H | A | S | N | F | R | S | T | H | D | S | L | Q | T | 289 |
| ABR68789.1 | R | Q | M | V | S | D | Y | K | Q | H | F | R | N | L | A | E | H | A | S | N | F | R | S | T | H | D | S | L | Q | T | 289 |
| ABR68788.1 | R | Q | M | V | S | D | Y | K | Q | H | F | R | N | L | A | E | H | A | S | N | F | R | S | T | H | D | S | L | Q | T | 289 |
| ABR14856.1 | R | Q | M | V | S | D | Y | K | Q | H | F | R | N | L | A | E | H | A | S | N | F | R | S | T | H | D | S | L | Q | T | 289 |
| AAC69799.1 | R | Q | M | V | S | D | Y | K | Q | H | F | R | N | L | A | E | H | A | S | N | F | R | S | T | H | D | S | L | Q | T | 289 |
| AAC62574.1 | R | Q | M | V | S | D | Y | K | Q | H | F | R | N | L | A | E | H | A | S | N | F | R | S | T | H | D | S | L | Q | T | 289 |
| AAF64077.1 | R | Q | M | V | S | D | Y | K | Q | H | F | R | N | L | A | E | H | A | S | N | F | R | S | T | H | D | S | L | Q | T | 289 |
| A4TSQ1.1 | R | Q | M | V | S | D | Y | K | Q | H | F | R | N | L | A | E | H | A | S | N | F | R | S | T | H | D | S | L | Q | T | 289 |
| YP_001004069.1 | R | Q | M | V | S | D | Y | K | Q | H | F | R | N | L | A | E | H | A | S | N | F | R | S | T | H | D | S | L | Q | T | 289 |
| CAL10039.1 | R | Q | M | V | S | D | Y | K | Q | H | F | R | N | L | A | E | H | A | S | N | F | R | S | T | H | D | S | L | Q | T | 289 |
| P23994.1 | R | Q | M | V | S | D | Y | K | Q | H | F | R | N | L | A | E | H | A | S | N | F | R | S | T | H | D | S | L | Q | T | 289 |
| AAA27645.1 | R | Q | M | V | S | D | Y | K | Q | H | F | R | N | L | A | E | H | A | S | N | F | R | S | T | H | D | S | L | Q | T | 289 |
| AAF64076.1 | R | Q | M | V | S | D | Y | K | Q | H | F | R | N | L | A | E | H | A | S | N | F | R | S | T | H | D | S | L | Q | T | 289 |
| YP_636823.1 | R | Q | M | V | S | D | Y | K | Q | H | F | R | N | L | A | E | H | A | S | N | F | R | S | T | H | D | S | L | Q | T | 289 |
| ABG16274.1 | R | Q | M | V | S | D | Y | K | Q | H | F | R | N | L | A | E | H | A | S | N | F | R | S | T | H | D | S | L | Q | T | 289 |
| ABP42325.1 | R | Q | M | V | S | D | Y | K | Q | H | F | R | N | L | A | E | H | A | S | N | F | R | S | T | H | D | S | L | Q | T | 289 |
| YP_001154615.1 | R | Q | M | V | S | D | Y | K | Q | H | F | R | N | L | A | E | H | A | S | N | F | R | S | T | H | D | S | L | Q | T | 289 |
| ABB16313.1 | R | Q | M | V | S | D | Y | K | Q | H | F | R | N | L | A | E | H | A | S | N | F | R | S | T | H | D | S | L | Q | T | 289 |
| YP_001874676.1 | R | Q | M | V | S | D | Y | K | Q | H | F | R | N | L | A | E | H | A | S | N | F | R | S | T | H | D | S | L | Q | T | 289 |
| ACC91219.1 | R | Q | M | V | S | D | Y | K | Q | H | F | R | N | L | A | E | H | A | S | N | F | R | S | T | H | D | S | L | Q | T | 292 |
| ABI97154.1 | R | Q | M | V | S | D | Y | K | Q | H | F | R | N | L | A | E | H | A | S | N | F | R | S | T | H | D | S | L | Q | T | 289 |
| LcrV.pro | R | Q | M | V | S | D | Y | K | Q | I | F | R | N | L | A | E | H | A

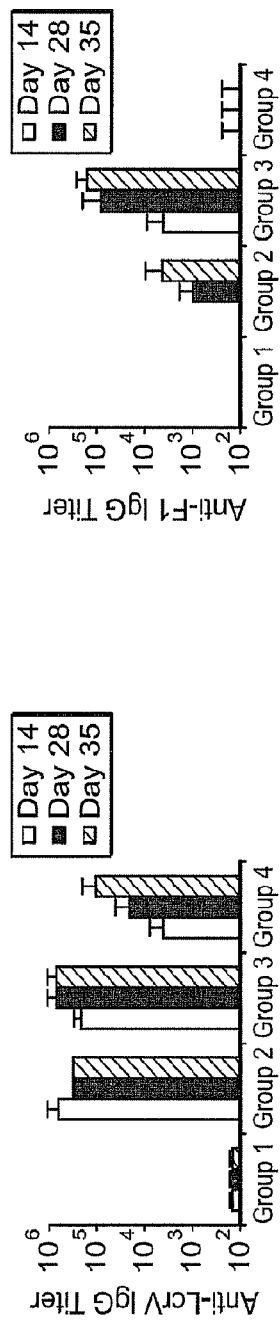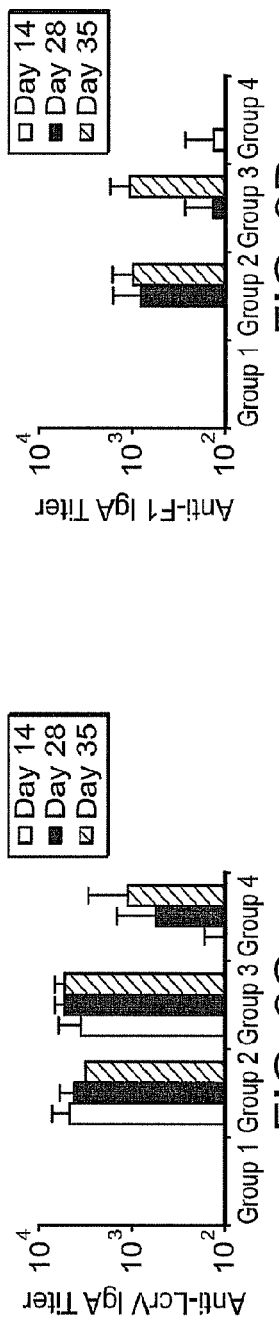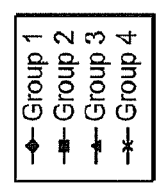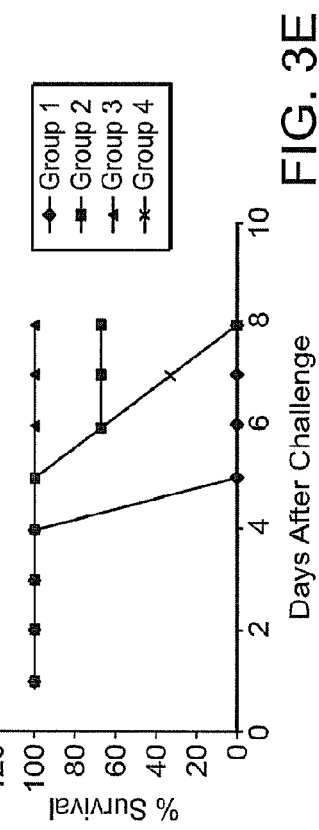

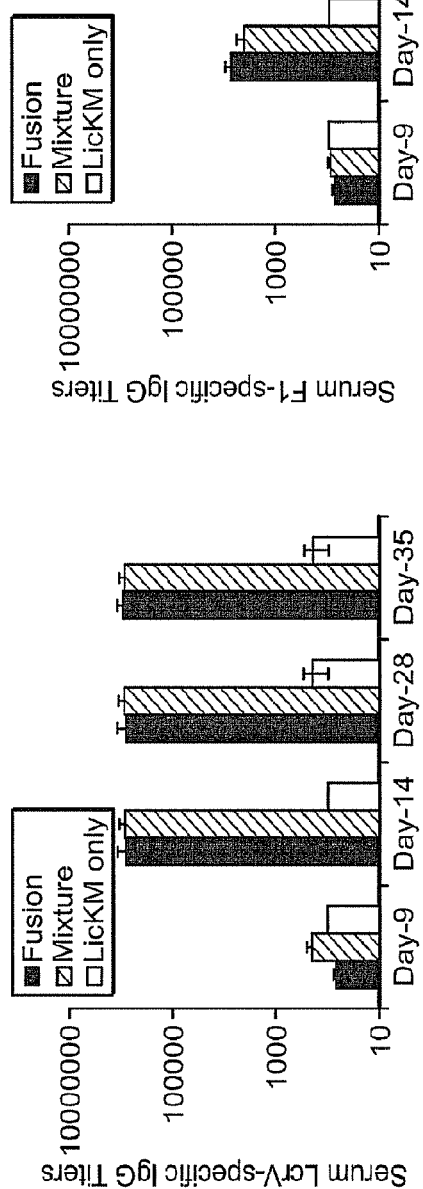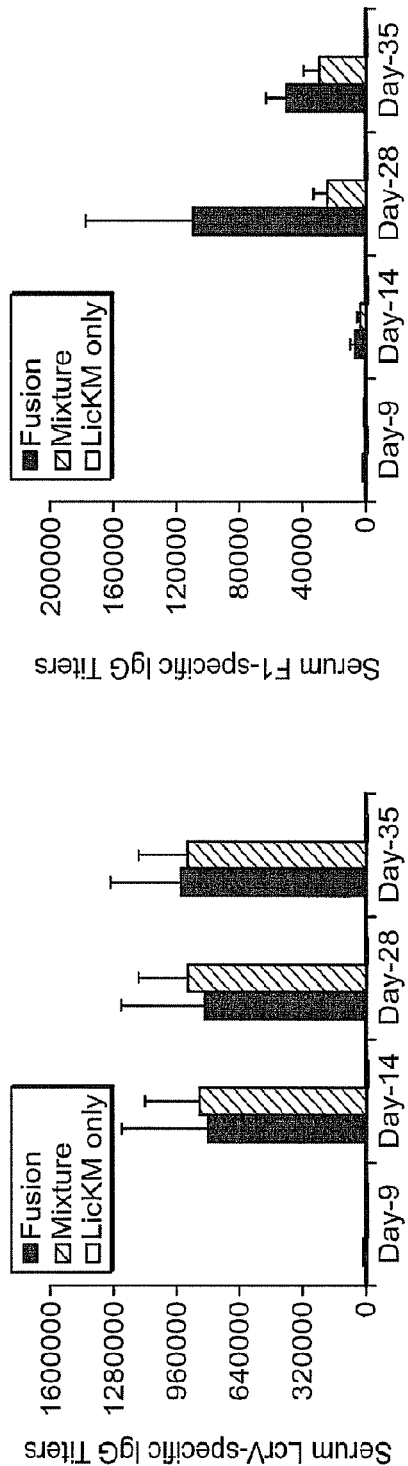
FIG. 5A, FIG. 5B, FIG. 5C, FIG. 5D

SEQUENCE LISTING

<160> NUMBER OF SEQ ID NOS: 104

<210> SEQ ID NO 1
<211> LENGTH: 170
<212> TYPE: PRT
<213> ORGANISM: Yersinia pestis CO92

<400> SEQUENCE: 1

Met Lys Lys Ile Ser Ser Val Ile Ala Ile Ala Leu Phe Gly Thr Ile
1               5                   10                  15

Ala Thr Ala Asn Ala Ala Asp Leu Thr Ala Ser Thr Thr Ala Thr Ala
            20                  25                  30

Thr Leu Val Glu Pro Ala Arg Ile Thr Leu Thr Tyr Lys Glu Gly Ala
        35                  40                  45

Pro Ile Thr Ile Met Asp Asn Gly Asn Ile Asp Thr Glu Leu Leu Val
    50                  55                  60

Gly Thr Leu Thr Leu Gly Gly Tyr Lys Thr Gly Thr Ser Thr Ser
65                  70                  75                  80

Val Asn Phe Thr Asp Ala Ala Gly Asp Pro Met Tyr Leu Thr Phe Thr
                85                  90                  95

Ser Gln Asp Gly Asn Asn His Gln Phe Thr Thr Lys Val Ile Gly Lys
            100                 105                 110

Asp Ser Arg Asp Phe Asp Ile Ser Pro Lys Val Asn Gly Glu Asn Leu
        115                 120                 125

Val Gly Asp Asp Val Val Leu Ala Thr Gly Ser Gln Asp Phe Phe Val
    130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln
                165                 170

<210> SEQ ID NO 2
<211> LENGTH: 513
<212> TYPE: DNA
<213> ORGANISM: Yersinia pestis CO92

<400> SEQUENCE: 2
atgaaaaaaa tcagttccgt tatcgccatt gcattatttg gaactattgc aactgctaat      60
gcggcagatt taactgcaag caccactgca acggcaactc ttgttgaacc agcccgcatc     120
actcttacat ataaggaagg cgctccaatt acaattatgg acaatggaaa catcgataca     180
gaattacttg ttggtacgct tactcttggc ggctataaaa caggaaccac tagcacatct     240
gttaacttta cagatgccgc gggtgatccc atgtacttaa catttacttc tcaggatgga     300
aataaccacc aattcactac aaaagtgatt ggcaaggatt ctagagattt tgatatctct     360
cctaaggtaa acggtgagaa ccttgtgggg gatgacgtcg tcttggctac gggcagccag     420
gatttctttg ttcgctcaat tggttccaaa ggcggtaaac ttgcagcagg taaatacact     480
gatgctgtaa ccgtaaccgt atctaaccaa taa                                  513

<210> SEQ ID NO 3
<211> LENGTH: 149
<212> TYPE: PRT
<213> ORGANISM: Yersinia pestis CO92

<400> SEQUENCE: 3

Ala Asp Leu Thr Ala Ser Thr Thr Ala Thr Ala Thr Leu Val Glu Pro

```
              1               5              10              15
        Ala Arg Ile Thr Leu Thr Tyr Lys Glu Gly Ala Pro Ile Thr Ile Met
                         20                  25                  30

Asp Asn Gly Asn Ile Asp Thr Glu Leu Leu Val Gly Thr Leu Thr Leu
                         35                  40                  45

Gly Gly Tyr Lys Thr Gly Thr Thr Ser Thr Ser Val Asn Phe Thr Asp
                     50                  55                  60

Ala Ala Gly Asp Pro Met Tyr Leu Thr Phe Thr Ser Gln Asp Gly Asn
         65                  70                  75                  80

Asn His Gln Phe Thr Thr Lys Val Ile Gly Lys Asp Ser Arg Asp Phe
                             85                  90                  95

Asp Ile Ser Pro Lys Val Asn Gly Glu Asn Leu Val Gly Asp Asp Val
                        100                 105                 110

Val Leu Ala Thr Gly Ser Gln Asp Phe Val Arg Ser Ile Gly Ser
                    115                 120                 125

Lys Gly Gly Lys Leu Ala Ala Gly Lys Tyr Thr Asp Ala Val Thr Val
                130                 135                 140

Thr Val Ser Asn Gln
        145

<210> SEQ ID NO 4
<211> LENGTH: 450
<212> TYPE: DNA
<213> ORGANISM: Yersinia pestis CO92

<400> SEQUENCE: 4
gcagatttaa ctgcaagcac cactgcaacg gcaactcttg ttgaaccagc ccgcatcact     60
cttacatata aggaaggcgc tccaattaca attatggaca atggaaacat cgatacagaa    120
ttacttgttg gtacgcttac tcttggcggc tataaaacag gaaccactag cacatctgtt    180
aactttacag atgccgcggg tgatcccatg tacttaacat tacttctca ggatggaaat    240
aaccaccaat tcactacaaa agtgattggc aaggattcta gagattttga tatctctcct    300
aaggtaaacg gtgagaacct tgtgggggat gacgtcgtct ggctacggg cagccaggat    360
ttctttgttc gctcaattgg ttccaaaggc ggtaaacttg cagcaggtaa atacactgat    420
gctgtaaccg taaccgtatc taaccaataa                                     450

<210> SEQ ID NO 5
<211> LENGTH: 170
<212> TYPE: PRT
<213> ORGANISM: Yersinia pestis

<400> SEQUENCE: 5

Met Lys Lys Ile Ser Ser Val Ile Ala Ile Ala Leu Phe Gly Thr Ile
          1               5                  10                  15

Ala Thr Ala Asn Ala Ala Asp Leu Thr Ala Ser Thr Thr Ala Thr Ala
                         20                  25                  30

Thr Leu Val Glu Pro Ala Arg Ile Thr Leu Thr Tyr Lys Glu Gly Ser
                         35                  40                  45

Pro Ile Thr Ile Met Asp Asn Gly Asn Ile Asp Thr Glu Leu Leu Val
                     50                  55                  60

Gly Thr Leu Thr Leu Gly Gly Tyr Lys Thr Gly Thr Thr Ser Thr Ser
         65                  70                  75                  80

Val Asn Phe Thr Asp Ala Ala Gly Asp Pro Met Tyr Leu Thr Phe Thr
                             85                  90                  95

Ser Gln Asp Gly Asn Asn His Gln Phe Thr Thr Lys Val Ile Gly Lys
```

```
                    100                 105                 110
Asp Ser Arg Asp Phe Asp Ile Ser Pro Lys Val Asn Gly Glu Asn Leu
            115                 120                 125

Val Gly Asp Asp Val Val Leu Ala Thr Gly Ser Gln Asp Phe Phe Val
        130                 135                 140

Arg Ser Ile Gly Ser Lys Gly Gly Lys Leu Ala Ala Gly Lys Tyr Thr
145                 150                 155                 160

Asp Ala Val Thr Val Thr Val Ser Asn Gln
                165                 170

<210> SEQ ID NO 6
<211> LENGTH: 513
<212> TYPE: DNA
<213> ORGANISM: Yersinia pestis

<400> SEQUENCE: 6
atgaaaaaaa tcagttccgt tatcgccatt gcattatttg gaactattgc aactgctaat      60
gcggcagatt taactgcaag caccactgca acggcaactc ttgttgaacc agcccgcatc     120
actcttacat ataaggaagg ctctccaatt acaattatgg acaatggaaa catcgataca     180
gaattacttg ttggtacgct tactcttggc ggctataaaa caggaaccac tagcacatct     240
gttaacttta cagatgccgc gggtgatccc atgtacttaa catttacttc tcaggatgga     300
aataaccacc aattcactac aaaagtgatt ggcaaggatt ctagagattt tgatatctct     360
cctaaggtaa acggtgagaa ccttgtgggg gatgacgtcg tcttggctac gggcagccag     420
gatttctttg ttcgctcaat tggttccaaa ggcggtaaac ttgcagcagg taaatacact     480
gatgctgtaa ccgtaaccgt atctaaccaa taa                                  513

<210> SEQ ID NO 7
<211> LENGTH: 149
<212> TYPE: PRT
<213> ORGANISM: Yersinia pestis

<400> SEQUENCE: 7

Ala Asp Leu Thr Ala Ser Thr Thr Ala Thr Ala Thr Leu Val Glu Pro
1               5                   10                  15

Ala Arg Ile Thr Leu Thr Tyr Lys Glu Gly Ser Pro Ile Thr Ile Met
            20                  25                  30

Asp Asn Gly Asn Ile Asp Thr Glu Leu Leu Val Gly Thr Leu Thr Leu
        35                  40                  45

Gly Gly Tyr Lys Thr Gly Thr Thr Ser Thr Ser Val Asn Phe Thr Asp
    50                  55                  60

Ala Ala Gly Asp Pro Met Tyr Leu Thr Phe Thr Ser Gln Asp Gly Asn
65                  70                  75                  80

Asn His Gln Phe Thr Thr Lys Val Ile Gly Lys Asp Ser Arg Asp Phe
                85                  90                  95

Asp Ile Ser Pro Lys Val Asn Gly Glu Asn Leu Val Gly Asp Asp Val
            100                 105                 110

Val Leu Ala Thr Gly Ser Gln Asp Phe Phe Val Arg Ser Ile Gly Ser
        115                 120                 125

Lys Gly Gly Lys Leu Ala Ala Gly Lys Tyr Thr Asp Ala Val Thr Val
    130                 135                 140

Thr Val Ser Asn Gln
145

<210> SEQ ID NO 8
```

-continued

<211> LENGTH: 449
<212> TYPE: DNA
<213> ORGANISM: Yersinia pestis

<400> SEQUENCE: 8

```
cagatttaac tgcaagcacc actgcaacgg caactcttgt tgaaccagcc cgcatcactc     60
ttacatataa ggaaggctct ccaattacaa ttatggacaa tggaaacatc gatacagaat    120
tacttgttgg tacgcttact cttggcggct ataaaacagg aaccactagc acatctgtta    180
actttacaga tgccgcgggt gatcccatgt acttaacatt tacttctcag gatggaaata    240
accaccaatt cactacaaaa gtgattggca aggattctag agattttgat atctctccta    300
aggtaaacgg tgagaacctt gtgggggatg acgtcgtctt ggctacgggc agccaggatt    360
tctttgttcg ctcaattggt tccaaaggcg gtaaacttgc agcaggtaaa tacactgatg    420
ctgtaaccgt aaccgtatct aaccaataa                                      449
```

<210> SEQ ID NO 9
<211> LENGTH: 326
<212> TYPE: PRT
<213> ORGANISM: Yersinia enterocolitica

<400> SEQUENCE: 9

```
Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270
```

```
Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 10
<211> LENGTH: 978
<212> TYPE: DNA
<213> ORGANISM: Yersinia enterocolitica

<400> SEQUENCE: 10
atgataaggg cttatgaaca aaatccacag cattttattg aagacctaga gaaagtgcga     60
gtcgaacagc tgaccggcca tggtcgtcc gttctcgaag aattggtgca attagttaaa    120
gataaaaaca tcgatatttc tattaagtac gaccctagga aggattctga ggtatttgct    180
aatagagtga ttacagatga tattgaatta ctaaaaaaga tattggcata cttccttcct    240
gaggatgcta ttcttaaggg tggacactat gacaatcaac ttcaaaacgg cattaagagg    300
gttaaggagt tcctcgaaag ctctccaaat actcaatggg agttacgtgc ttttatggct    360
gttatgcatt ttagtctgac agctgatcga attgatgatg atattctaaa ggtaattgta    420
gattccatga atcatcacgg tgacgccagg tctaagttgc gtgaagagct tgctgagttg    480
actgctgaac tgaagatata ttccgtgata caggcagaaa ttaacaagca cttatcatct    540
tcaggaacta ttaatattca cgataagtct attaatctta tggataaaaa cctatacggt    600
tatactgatg aggagatttt caaagctagt gcggagtaca aaatattaga aaagatgccc    660
caaactacta tacaggtgga tgggtctgaa aagaagattg tttctatcaa agatttcctg    720
ggtagcgaaa acaaaagaac gggagcactt gggaatctca agaattctta ttcatataac    780
aaagataaca acgagctttc acatttcgca actacttgta gtgataagtc cagaccactc    840
aacgatcttg tatcacaaaa gacaactcaa ttgtctgaca ttacttctcg tttcaacagc    900
gctattgaag cacttaatag gttcattcag aagtacgatt ctgtgatgca aagattgctt    960
gatgatacat ctggaaag                                                  978

<210> SEQ ID NO 11
<211> LENGTH: 2255
<212> TYPE: DNA
<213> ORGANISM: Artificial Sequence
<220> FEATURE:
<223> OTHER INFORMATION: Synthetic construct

<400> SEQUENCE: 11
ggtaccggat ccttaattaa atgggtttcg tgcttttctc tcagcttcct tctttccttc     60
ttgtgtctac ccttcttctt ttccttgtga tttctcactc ttgcagggct cagaatggtg    120
gttcttaccc ttacaagtct ggtgagtaca ggaccaagtc tttcttcggt tacggttact    180
acgaagtgag aatgaaggct gctaagaatg tgggtattgt gtcatctttc ttcacctaca    240
ccggtccttc agataataac ccttgggatg agattgatat tgagttcctt ggaaaggata    300
ccaccaaggt tcagttcaac tggtacaaga acggtgttgg tggaaatgag taccttcaca    360
accttggttt cgatgcttct caggatttcc acacctacgg ttttgagtgg aggcctgatt    420
acattgattt ctacgtggat ggaaagaagg tttacagggg aaccaggaac attcctgtta    480
```

```
cccctggaaa gattatgatg aacctttggc ctggtattgg tgttgatgag tggcttggta    540
gatacgatgg aaggactcct cttcaggctg agtacgagta cgttaagtac taccctaacg    600
gtagatctat gattagggct tacgagcaga atcctcagca cttcattgag gatcttgaga    660
aagttagggt ggagcagctt actggtcatg gttcttcagt gcttgaagag cttgttcagc    720
ttgtgaagga taagaacatt gatatttcta ttaagtacga tcctaggaag gattctgagg    780
tgttcgctaa cagagtgatt accgatgata ttgagcttct gaagaagatt cttgcttact    840
tccttcctga ggatgctatt cttaaggggt gtcactacga taatcagctt cagaacggta    900
ttaagagggt gaaagagttc cttgagtcat ctcctaatac ccagtgggag cttagggctt    960
ttatggctgt gatgcacttc tctcttaccg ctgataggat tgatgatgat attcttaaag   1020
tgattgtgga ttctatgaac caccatggtg atgctaggtc taagttgagg gaagagcttg   1080
ctgaacttac cgctgagttg aaaatctact ctgtgattca ggctgagatt aacaagcacc   1140
tttcttcatc tggaaccatt aacattcacg ataagtctat taaccttatg gataagaacc   1200
tttacggtta caccgatgaa gagattttca aggcttctgc tgagtacaag attcttgaga   1260
agatgcctca gactaccatt caagtggatg gttctgagaa gaaaattgtg tctattaagg   1320
atttccttgg atctgagaac aagaggactg gtgctttggg taaccttaag aactcttact   1380
cttacaacaa ggataacaac gagctttctc acttcgctac tacctgctct gataagtcta   1440
ggcctcttaa cgatcttgtg tctcaaaaga ccacccagct ttctgatatt acctctaggt   1500
tcaactctgc tattgaggct cttaacagat tcattcagaa atacgattct gtgatgcaaa   1560
ggcttcttga tgatacctct ggaaagaagc ttgttgttaa caccccttc gtggctgttt    1620 tctctaactt cgattcttct cagtgggaaa aggctgattg gctaacggt tctgtgttca    1680 actgtgtgtg gaagccttct caggtgacct ctctaacgg aaagatgatt cttaccttg    1740 ataggggaata cgtcgacgct gatttgactg cttctactac tgctactgct actcttgttg    1800
agcctgctag gattacccct acctacaaag agggtgctcc tattactatt atggataacg   1860
gtaacattga taccgagttg cttgtgggta ctccttacact tggtggttac aagaccggta   1920
ctacctctac ttctgtgaac ttcaccgatg ctgctggtga tcctatgtac cttaccttca   1980
cctctcagga tggaaataac caccagttca ccaccaaagt gattggaaag gattctaggg   2040
atttcgatat ttctcctaag gtgaacggtg aaaatcttgt gggtgacgat gttgttcttg   2100
ctaccggttc acaggatttc tttgtgagat caattggttc taagggtgga agttggctg    2160 ctggaaagta cactgatgct gtgactgtga ctgtgtctaa tcaggtcgac catcatcatc   2220
atcaccacaa ggatgagctt tgatgactcg agctc                               2255

<210> SEQ ID NO 12
<211> LENGTH: 492
<212> TYPE: DNA
<213> ORGANISM: Artificial Sequence
<220> FEATURE:
<223> OTHER INFORMATION: Synthetic oligonucleotide

<400> SEQUENCE: 12
cagaatggtg gttcttaccc ttacaagtct ggtgagtaca ggaccaagtc tttcttcggt      60
tacggttact acgaagtgag aatgaaggct gctaagaatg tgggtattgt gtcatctttc     120
ttcacctaca ccggtccttc agataataac ccttgggatg agattgatat tgagttcctt     180
ggaaaggata ccaccaaggt tcagttcaac tggtacaaga acggtgttgg tggaaatgag     240
taccttcaca accttggttt cgatgcttct caggatttcc acacctacgg ttttgagtgg     300
```

```
aggcctgatt acattgattt ctacgtggat ggaaagaagg tttacagggg aaccaggaac    360
attcctgtta cccctggaaa gattatgatg aacctttggc ctggtattgg tgttgatgag    420
tggcttggta gatacgatgg aaggactcct cttcaggctg agtacgagta cgttaagtac    480
taccctaacg gt                                                        492

<210> SEQ ID NO 13
<211> LENGTH: 159
<212> TYPE: DNA
<213> ORGANISM: Artificial Sequence
<220> FEATURE:
<223> OTHER INFORMATION: Synthetic oligonucleotide

<400> SEQUENCE: 13
gttgttaaca cccctttcgt ggctgttttc tctaacttcg attcttctca gtgggaaaag     60
gctgattggg ctaacggttc tgtgttcaac tgtgtgtgga agccttctca ggtgaccttc    120
tctaacggaa agatgattct taccttgat agggaatac                            159

<210> SEQ ID NO 14
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 14
catcatcatc atcaccac                                                   18

<210> SEQ ID NO 15
<211> LENGTH: 12
<212> TYPE: DNA
<213> ORGANISM: Artificial Sequence
<220> FEATURE:
<223> OTHER INFORMATION: Synthetic oligonucleotide

<400> SEQUENCE: 15
aaggatgagc tt                                                         12

<210> SEQ ID NO 16
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 16
atgggtttcg tgcttttctc tcagcttcct tctttccttc ttgtgtctac ccttcttctt     60
ttccttgtga tttctcactc ttgcagggct                                      90

<210> SEQ ID NO 17
<211> LENGTH: 981
<212> TYPE: DNA
<213> ORGANISM: Artificial Sequence
<220> FEATURE:
<223> OTHER INFORMATION: Synthetic oligonucletide

<400> SEQUENCE: 17
atgattaggg cttacgagca gaatcctcag cacttcattg aggatcttga gaaagttagg     60
gtggagcagc ttactggtca tggttcttca gtgcttgaag agcttgttca gcttgtgaag    120
gataagaaca ttgatatttc tattaagtac gatcctagga aggattctga ggtgttcgct    180
aacagagtga ttaccgatga tattgagctt ctgaagaaga ttcttgctta cttccttcct    240
```

```
gaggatgcta ttcttaaggg tggtcactac gataatcagc ttcagaacgg tattaagagg      300
gtgaaagagt tccttgagtc atctcctaat acccagtggg agcttagggc ttttatggct      360
gtgatgcact tctctcttac cgctgatagg attgatgatg atattcttaa agtgattgtg      420
gattctatga accaccatgg tgatgctagg tctaagttga gggaagagct tgctgaactt      480
accgctgagt tgaaaatcta ctctgtgatt caggctgaga ttaacaagca cctttcttca      540
tctggaacca ttaacattca cgataagtct attaacctta tggataagaa cctttacggt      600
tacaccgatg aagagatttt caaggcttct gctgagtaca agattcttga gaagatgcct      660
cagactacca ttcaagtgga tggttctgag aagaaaattg tgtctattaa ggatttcctt      720
ggatctgaga acaagaggac tggtgctttg gtaaccttta agaactctta ctcttacaac      780
aaggataaca acgagctttc tcacttcgct actacctgct ctgataagtc taggcctctt      840
aacgatcttg tgtctcaaaa gaccacccag ctttctgata ttacctctag gttcaactct      900
gctattgagg ctcttaacag attcattcag aaatacgatt ctgtgatgca aaggcttctt      960 gatgataccct ctggaaagaa g                                               981
```

<210> SEQ ID NO 18
<211> LENGTH: 447
<212> TYPE: DNA
<213> ORGANISM: Artificial Sequence
<220> FEATURE:
<223> OTHER INFORMATION: Synthetic oligonucleotide

<400> SEQUENCE: 18

```
gctgatttga ctgcttctac tactgctact gctactcttg ttgagcctgc taggattacc       60
cttacctaca agagggtgc tcctattact attatggata acggtaacat tgataccgag       120
ttgcttgtgg gtactcttac acttggtggt tacaagaccg gtactacctc tacttctgtg       180
aacttcaccg atgctgctgg tgatcctatg taccttacct tcacctctca ggatggaaat       240
aaccaccagt tcaccaccaa agtgattgga aaggattcta gggatttcga tatttctcct       300
aaggtgaacg gtgaaaatct gtgggtgac gatgttgttc ttgctaccgg ttcacaggat       360
ttctttgtga gatcaattgg ttctaagggt ggaaagttgg ctgctggaaa gtacactgat       420
gctgtgactg tgactgtgtc taatcag                                          447
```

<210> SEQ ID NO 19
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 19

```
ggatccttaa ttaa                                                         14
```

<210> SEQ ID NO 20
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 20

```
ggatcc                                                                   6
```

<210> SEQ ID NO 21
<211> LENGTH: 6

```
<212> TYPE: DNA
<213> ORGANISM: Artificial Sequence
<220> FEATURE:
<223> OTHER INFORMATION: Synthetic oligonucleotide

<400> SEQUENCE: 21 agactc                                                                      6

<210> SEQ ID NO 22
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 22 aagctt                                                                      6

<210> SEQ ID NO 23
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 23 gtcgac                                                                      6

<210> SEQ ID NO 24
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 24 ctcgagctc                                                                   9

<210> SEQ ID NO 25
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 25 ctcgag                                                                      6

<210> SEQ ID NO 26
<211> LENGTH: 6
<212> TYPE: DNA
<213> ORGANISM: Artificial Sequence
<220> FEATURE:
<223> OTHER INFORMATION: Synthetic oligonucleotide

<400> SEQUENCE: 26 gagctc                                                                      6

<210> SEQ ID NO 27
<211> LENGTH: 740
<212> TYPE: PRT
<213> ORGANISM: Artificial Sequence
<220> FEATURE:
<223> OTHER INFORMATION: Synthetic construct

<400> SEQUENCE: 27

Met Gly Phe Val Leu Phe Ser Gln Leu Pro Ser Phe Leu Leu Val Ser
```

```
                1               5                  10                 15
        Thr Leu Leu Leu Phe Leu Val Ile Ser His Ser Cys Arg Ala Gln Asn
                        20                  25                  30

Gly Gly Ser Tyr Pro Tyr Lys Ser Gly Glu Tyr Arg Thr Lys Ser Phe
                        35                  40                  45

Phe Gly Tyr Gly Tyr Tyr Glu Val Arg Met Lys Ala Ala Lys Asn Val
                        50                  55                  60

Gly Ile Val Ser Ser Phe Phe Thr Tyr Thr Gly Pro Ser Asp Asn Asn
         65                  70                  75                  80

Pro Trp Asp Glu Ile Asp Ile Glu Phe Leu Gly Lys Asp Thr Thr Lys
                         85                  90                  95

Val Gln Phe Asn Trp Tyr Lys Asn Gly Val Gly Gly Asn Glu Tyr Leu
                        100                 105                 110

His Asn Leu Gly Phe Asp Ala Ser Gln Asp Phe His Thr Tyr Gly Phe
                        115                 120                 125

Glu Trp Arg Pro Asp Tyr Ile Asp Phe Tyr Val Asp Gly Lys Lys Val
                        130                 135                 140

Tyr Arg Gly Thr Arg Asn Ile Pro Val Thr Pro Gly Lys Ile Met Met
        145                 150                 155                 160

Asn Leu Trp Pro Gly Ile Gly Val Asp Glu Trp Leu Gly Arg Tyr Asp
                        165                 170                 175

Gly Arg Thr Pro Leu Gln Ala Glu Tyr Glu Tyr Val Lys Tyr Tyr Pro
                        180                 185                 190

Asn Gly Arg Ser Met Ile Arg Ala Tyr Glu Gln Asn Pro Gln His Phe
                        195                 200                 205

Ile Glu Asp Leu Glu Lys Val Arg Val Glu Gln Leu Thr Gly His Gly
                        210                 215                 220

Ser Ser Val Leu Glu Glu Leu Val Gln Leu Val Lys Asp Lys Asn Ile
        225                 230                 235                 240

Asp Ile Ser Ile Lys Tyr Asp Pro Arg Lys Asp Ser Glu Val Phe Ala
                        245                 250                 255

Asn Arg Val Ile Thr Asp Asp Ile Glu Leu Leu Lys Lys Ile Leu Ala
                        260                 265                 270

Tyr Phe Leu Pro Glu Asp Ala Ile Leu Lys Gly Gly His Tyr Asp Asn
                        275                 280                 285

Gln Leu Gln Asn Gly Ile Lys Arg Val Lys Glu Phe Leu Glu Ser Ser
                        290                 295                 300

Pro Asn Thr Gln Trp Glu Leu Arg Ala Phe Met Ala Val Met His Phe
        305                 310                 315                 320

Ser Leu Thr Ala Asp Arg Ile Asp Asp Ile Leu Lys Val Ile Val
                        325                 330                 335

Asp Ser Met Asn His His Gly Asp Ala Arg Ser Lys Leu Arg Glu Glu
                        340                 345                 350

Leu Ala Glu Leu Thr Ala Glu Leu Lys Ile Tyr Ser Val Ile Gln Ala
                        355                 360                 365

Glu Ile Asn Lys His Leu Ser Ser Ser Gly Thr Ile Asn Ile His Asp
                        370                 375                 380

Lys Ser Ile Asn Leu Met Asp Lys Asn Leu Tyr Gly Tyr Thr Asp Glu
        385                 390                 395                 400

Glu Ile Phe Lys Ala Ser Ala Glu Tyr Lys Ile Leu Glu Lys Met Pro
                        405                 410                 415

Gln Thr Thr Ile Gln Val Asp Gly Ser Glu Lys Lys Ile Val Ser Ile
                        420                 425                 430
```

-continued

```
Lys Asp Phe Leu Gly Ser Glu Asn Lys Arg Thr Gly Ala Leu Gly Asn
            435                 440                 445

Leu Lys Asn Ser Tyr Ser Tyr Asn Lys Asp Asn Glu Leu Ser His
    450                 455                 460

Phe Ala Thr Thr Cys Ser Asp Lys Ser Arg Pro Leu Asn Asp Leu Val
465                 470                 475                 480

Ser Gln Lys Thr Thr Gln Leu Ser Asp Ile Thr Ser Arg Phe Asn Ser
                485                 490                 495

Ala Ile Glu Ala Leu Asn Arg Phe Ile Gln Lys Tyr Asp Ser Val Met
            500                 505                 510

Gln Arg Leu Leu Asp Asp Thr Ser Gly Lys Lys Leu Val Val Asn Thr
        515                 520                 525

Pro Phe Val Ala Val Phe Ser Asn Phe Asp Ser Ser Gln Trp Glu Lys
    530                 535                 540

Ala Asp Trp Ala Asn Gly Ser Val Phe Asn Cys Val Trp Lys Pro Ser
545                 550                 555                 560

Gln Val Thr Phe Ser Asn Gly Lys Met Ile Leu Thr Leu Asp Arg Glu
                565                 570                 575

Tyr Val Asp Ala Asp Leu Thr Ala Ser Thr Thr Ala Thr Ala Thr Leu
            580                 585                 590

Val Glu Pro Ala Arg Ile Thr Leu Thr Tyr Lys Glu Gly Ala Pro Ile
        595                 600                 605

Thr Ile Met Asp Asn Gly Asn Ile Asp Thr Glu Leu Leu Val Gly Thr
    610                 615                 620

Leu Thr Leu Gly Gly Tyr Lys Thr Gly Thr Thr Ser Thr Ser Val Asn
625                 630                 635                 640

Phe Thr Asp Ala Ala Gly Asp Pro Met Tyr Leu Thr Phe Thr Ser Gln
                645                 650                 655

Asp Gly Asn Asn His Gln Phe Thr Thr Lys Val Ile Gly Lys Asp Ser
            660                 665                 670

Arg Asp Phe Asp Ile Ser Pro Lys Val Asn Gly Glu Asn Leu Val Gly
        675                 680                 685

Asp Asp Val Val Leu Ala Thr Gly Ser Gln Asp Phe Phe Val Arg Ser
    690                 695                 700

Ile Gly Ser Lys Gly Gly Lys Leu Ala Ala Gly Lys Tyr Thr Asp Ala
705                 710                 715                 720

Val Thr Val Thr Val Ser Asn Gln Val Asp His His His His His His
                725                 730                 735

Lys Asp Glu Leu
            740

<210> SEQ ID NO 28
<211> LENGTH: 327
<212> TYPE: PRT
<213> ORGANISM: Artificial Sequence
<220> FEATURE:
<223> OTHER INFORMATION: Synthetic peptide

<400> SEQUENCE: 28

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
```

```
                50              55              60
Thr Asp Asp Ile Glu Leu Leu Lys Lys Ile Leu Ala Tyr Phe Leu Pro
 65                      70                  75                  80

Glu Asp Ala Ile Leu Lys Gly Gly His Tyr Asp Asn Gln Leu Gln Asn
                     85                  90                  95

Gly Ile Lys Arg Val Lys Glu Phe Leu Glu Ser Ser Pro Asn Thr Gln
                    100                 105                 110

Trp Glu Leu Arg Ala Phe Met Ala Val Met His Phe Ser Leu Thr Ala
                    115                 120                 125

Asp Arg Ile Asp Asp Ile Leu Lys Val Ile Val Asp Ser Met Asn
                    130                 135                 140

His His Gly Asp Ala Arg Ser Lys Leu Arg Glu Gly Leu Ala Glu Leu
145                 150                 155                 160

Thr Ala Glu Leu Lys Ile Tyr Ser Val Ile Gln Ala Glu Ile Asn Lys
                    165                 170                 175

His Leu Ser Ser Ser Gly Thr Ile Asn Ile His Asp Lys Ser Ile Asn
                    180                 185                 190

Leu Met Asp Lys Asn Leu Tyr Gly Tyr Thr Asp Glu Ile Phe Lys
                    195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                    245                 250                 255

Tyr Ser Tyr Asn Lys Asp Asn Asn Glu Leu Ser His Phe Ala Thr Thr
                    260                 265                 270

Cys Ser Asp Lys Ser Arg Pro Leu Asn Asp Leu Val Ser Gln Lys Thr
                    275                 280                 285

Thr Gln Leu Ser Asp Ile Thr Ser Arg Phe Asn Ser Ala Ile Glu Ala
                    290                 295                 300

Leu Asn Arg Phe Ile Gln Lys Tyr Asp Ser Val Met Gln Arg Leu Leu
305                 310                 315                 320

Asp Asp Thr Ser Gly Lys Lys
                    325

<210> SEQ ID NO 29
<211> LENGTH: 53
<212> TYPE: PRT
<213> ORGANISM: Artificial Sequence
<220> FEATURE:
<223> OTHER INFORMATION: Synthetic peptide

<400> SEQUENCE: 29

Val Val Asn Thr Pro Phe Val Ala Val Phe Ser Asn Phe Asp Ser Ser
 1               5                  10                  15

Gln Trp Glu Lys Ala Asp Trp Ala Asn Gly Ser Val Phe Asn Cys Val
                20                  25                  30

Trp Lys Pro Ser Gln Val Thr Phe Ser Asn Gly Lys Met Ile Leu Thr
                35                  40                  45

Leu Asp Arg Glu Tyr
    50

<210> SEQ ID NO 30
<211> LENGTH: 6
<212> TYPE: PRT
<213> ORGANISM: Artificial Sequence
```

-continued

```
<220> FEATURE:
<223> OTHER INFORMATION: Synthetic peptide

<400> SEQUENCE: 30

His His His His His His
 1               5

<210> SEQ ID NO 31
<211> LENGTH: 4
<212> TYPE: PRT
<213> ORGANISM: Artificial Sequence
<220> FEATURE:
<223> OTHER INFORMATION: Synthetic peptide

<400> SEQUENCE: 31

Lys Asp Glu Leu
 1

<210> SEQ ID NO 32
<211> LENGTH: 30
<212> TYPE: PRT
<213> ORGANISM: Artificial Sequence
<220> FEATURE:
<223> OTHER INFORMATION: Synthetic peptide

<400> SEQUENCE: 32

Met Gly Phe Val Leu Phe Ser Gln Leu Pro Ser Phe Leu Leu Val Ser
 1               5                  10                  15

Thr Leu Leu Leu Phe Leu Val Ile Ser His Ser Cys Arg Ala
            20                  25                  30

<210> SEQ ID NO 33
<211> LENGTH: 327
<212> TYPE: PRT
<213> ORGANISM: Artificial Sequence
<220> FEATURE:
<223> OTHER INFORMATION: Synthetic peptide

<400> SEQUENCE: 33

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175
```

```
His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Ile Phe Lys
        195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
                275                 280                 285

Thr Gln Leu Ser Asp Ile Thr Ser Arg Phe Asn Ser Ala Ile Glu Ala
                290                 295                 300

Leu Asn Arg Phe Ile Gln Lys Tyr Asp Ser Val Met Gln Arg Leu Leu
305                 310                 315                 320

Asp Asp Thr Ser Gly Lys Lys
                325

<210> SEQ ID NO 34
<211> LENGTH: 149
<212> TYPE: PRT
<213> ORGANISM: Artificial Sequence
<220> FEATURE:
<223> OTHER INFORMATION: Synthetic peptide

<400> SEQUENCE: 34

Ala Asp Leu Thr Ala Ser Thr Thr Ala Thr Leu Val Glu Pro
1               5                   10                  15

Ala Arg Ile Thr Leu Thr Tyr Lys Glu Gly Ala Pro Ile Thr Ile Met
            20                  25                  30

Asp Asn Gly Asn Ile Asp Thr Glu Leu Leu Val Gly Thr Leu Thr Leu
        35                  40                  45

Gly Gly Tyr Lys Thr Gly Thr Thr Ser Thr Ser Val Asn Phe Thr Asp
    50                  55                  60

Ala Ala Gly Asp Pro Met Tyr Leu Thr Phe Thr Ser Gln Asp Gly Asn
65                  70                  75                  80

Asn His Gln Phe Thr Thr Lys Val Ile Gly Lys Asp Ser Arg Asp Phe
                85                  90                  95

Asp Ile Ser Pro Lys Val Asn Gly Glu Asn Leu Val Gly Asp Asp Val
                100                 105                 110

Val Leu Ala Thr Gly Ser Gln Asp Phe Phe Val Arg Ser Ile Gly Ser
            115                 120                 125

Lys Gly Gly Lys Leu Ala Ala Gly Lys Tyr Thr Asp Ala Val Thr Val
130                 135                 140

Thr Val Ser Asn Gln
145

<210> SEQ ID NO 35
<211> LENGTH: 2
<212> TYPE: PRT
<213> ORGANISM: Artificial Sequence
<220> FEATURE:
<223> OTHER INFORMATION: Synthetic peptide corresponds to a BglII site

<400> SEQUENCE: 35
```

Arg Ser
 1

<210> SEQ ID NO 36
<211> LENGTH: 2
<212> TYPE: PRT
<213> ORGANISM: Artificial Sequence
<220> FEATURE:
<223> OTHER INFORMATION: Synthetic peptide corresponds to a HindIII site

<400> SEQUENCE: 36

Lys Leu
 1

<210> SEQ ID NO 37
<211> LENGTH: 2
<212> TYPE: PRT
<213> ORGANISM: Artificial Sequence
<220> FEATURE:
<223> OTHER INFORMATION: Synthetic peptide correspond to two SalI sites

<400> SEQUENCE: 37

Val Asp
 1

<210> SEQ ID NO 38
<211> LENGTH: 326
<212> TYPE: PRT
<213> ORGANISM: Artificial Sequence
<220> FEATURE:
<223> OTHER INFORMATION: Majority sequence

<400> SEQUENCE: 38

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

```
Gln Val Asp Gly Ser Glu Lys Ile Val Ser Ile Lys Asp Phe Leu
225                 230                 235                 240

Gly Ser Glu Asn Lys Arg Thr Gly Ala Leu Gly Asn Leu Lys Asn Ser
            245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 39
<211> LENGTH: 324
<212> TYPE: PRT
<213> ORGANISM: Yersinia enterocolitica

<400> S

```
Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Arg

<210> SEQ ID NO 40
<211> LENGTH: 333
<212> TYPE: PRT
<213> ORGANISM: Yersinia enterocolitica

<400> SEQUENCE: 40

Met Ile Arg Ala Tyr Glu Gln Asn Pro Gln His Phe Ile Glu Asp Leu
1               5                   10                  15

Glu Lys Val Arg Val Gln Leu Thr Gly His Gly Ser Ser Val Leu
            20                  25                  30

Glu Glu Leu Val Gln Leu Val Lys Asp Lys Lys Ile Asp Ile Ser Ile
        35                  40                  45

Lys Tyr Asp Pro Lys Lys Asp Ser Glu Val Phe Ala Glu Arg Val Ile
50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
            130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Glu Lys Ser Ile Asn
            180                 185                 190

Leu Met Asp Lys Asn Leu Tyr Gly Tyr Thr Asp Glu Gly Ile Phe Lys
        195                 200                 205

Ala Ser Ala Glu Tyr Lys Ile Leu Lys Lys Met Pro Gln Thr Thr Ile
210                 215                 220

Lys Asp Asp Glu Leu His Glu Val Gly Val Ile Ala Gly Ala Glu Lys
225                 230                 235                 240

Gln Ile Val Ser Ile Lys Asn Phe Leu Glu Ser Glu Asn Lys Arg Thr
                245                 250                 255

Gly Ala Leu Gly Asn Leu Lys Asp Ser Tyr Ser Tyr Asn Lys Asp Asn
            260                 265                 270

Asn Glu Leu Ser His Phe Ala Thr Ala Cys Ser Asp Lys Ser Arg Pro
        275                 280                 285

Leu Asn Asp Leu Val Ser Gln Lys Thr Thr Gln Leu Ser Asp Ile Thr
        290                 295                 300

Ser Arg Phe Asn Ser Ala Ile Glu Ala Leu Asn Arg Phe Ile Gln Lys
305                 310                 315                 320
```

Tyr Asp Ser Val Met Gln Arg Leu Leu Asp Asp Thr Arg
              325                 330

<210> SEQ ID NO 41
<211> LENGTH: 324
<212> TYPE: PRT
<213> ORGANISM: Yersinia enterocolitica

<400> SEQUENCE: 41

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Lys Ile Asp Ile Ser Ile
        35                  40                  45

Lys Tyr Asp Pro Lys Lys Asp Ser Glu Val Phe Ala

```
Met Ile Arg Ala Tyr Glu Gln Asn Pro Gln His Phe Ile Glu Asp Leu
  1               5                  10                  15

Glu Lys Val Arg Val Glu Gln Leu Thr Gly His Gly Ser Ser Val Leu
             20                  25                  30

Glu Glu Leu Val Gln Leu Val Lys Asp Lys Lys Ile Asp Ile Ser Ile
         35                  40                  45

Lys Tyr Asp Pro Lys Lys Asp Ser Glu Val Phe Ala Glu Arg Val Ile
 50                  55                  60

Thr Asp Asp Ile Glu Leu Leu Lys Lys Ile Leu Ala Tyr Phe Leu Pro
 65                  70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
            115                 120                 125

Asp Arg Ile Asp Asp Ile Leu Lys Val Ile Val Asp Ser Met Asn
            130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

Tyr Leu Ser Asn Ser Gly Thr Ile Asn Ile His Asp Lys Ser Ile Asn
                180                 185                 190

Leu Met Asp Lys Asn Leu Tyr Gly Tyr Thr Asp Glu Ile Phe Lys
            195                 200                 205

Ala Ser Ala Glu Tyr Lys Ile Leu Glu Lys Met Ser Gln Thr Thr Ile
            210                 215                 220

Lys Glu Gly Glu Thr Glu Lys Lys Ile Val Ser Ile Lys Asn Phe Leu
225                 230                 235                 240

Glu Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Ala
                260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
            290                 295                 300

Leu Asn Arg Phe Ile Gln Lys Tyr Asp Ser Val Met Gln Arg Leu Leu
305                 310                 315                 320

Asp Asp Thr Arg

<210> SEQ ID NO 43
<211> LENGTH: 333
<212> TYPE: PRT
<213> ORGANISM: Yersinia enterocolitica

<400> SEQUENCE: 43

Met Ile Arg Ala Tyr Glu Gln Asn Pro Gln His Phe Ile Glu Asp Leu
  1               5                  10                  15

Glu Lys Val Arg Val Glu Gln Leu Thr Gly His Gly Ser Ser Val Leu
             20                  25                  30

Glu Glu Leu Val Gln Leu Val Lys Asp Lys Lys Ile Asp Ile Ser Ile
         35                  40                  45
```

Lys Tyr Asp Pro Lys Lys Asp Ser Glu Val Phe Ala Glu Arg Val Ile
            50                  55                  60

Thr Asp Asp Ile Glu Leu Leu Lys Lys Ile Leu Ala Tyr Phe Leu Pro
 65                  70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
            115                 120                 125

Asp Arg Ile Asp Asp Ile Leu Lys Val Ile Asp Ser Met Asn
            130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Glu Lys Ser Ile Asn
            180                 185                 190

Leu Met Asp Lys Asn Leu Tyr Gly Tyr Thr Asp Glu Glu Ile Phe Lys
            195                 200                 205

Ala Ser Ala Glu Tyr Lys Ile Leu Lys Lys Met Pro Gln Thr Thr Ile
210                 215                 220

Lys Asp Asp Glu Leu His Glu Val Gly Val Ile Ala Gly Ala Glu Lys
225                 230                 235                 240

Gln Ile Val Ser Ile Lys Asn Phe Leu Glu Ser Glu Asn Lys Arg Thr
                245                 250                 255

Gly Ala Leu Gly Asn Leu Lys Asp Ser Tyr Ser Tyr Asn Lys Asp Asn
            260                 265                 270

Asn Glu Leu Ser His Phe Ala Thr Ala Cys Ser Asp Lys Ser Arg Pro
            275                 280                 285

Leu Asn Asp Leu Val Ser Gln Lys Thr Thr Gln Leu Ser Asp Ile Thr
            290                 295                 300

Ser Arg Phe Asn Ser Ala Ile Glu Ala Leu Asn Arg Phe Ile Gln Lys
305                 310                 315                 320

Tyr Asp Ser Val Met Gln Arg Leu Leu Asp Asp Thr Arg
                325                 330

<210> SEQ ID NO 44
<211> LENGTH: 324
<212> TYPE: PRT
<213> ORGANISM: Yersinia enterocolitica

<400> SEQUENCE:

```
Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
            115                 120                 125

Asp Arg Ile Asp Asp Ile Leu Lys Val Ile Val Asp Ser Met Asn
130                 135                 140

His His Gly Asp Ala Arg Gly Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Asn Ser Asp Thr Ile Asn Ile His Asp Lys Ser Ile Asn
            180                 185                 190

Leu Met Asp Lys Asn Leu Tyr Gly Tyr Thr Asp Glu Glu Ile Phe Lys
            195                 200                 205

Ala Ser Ala Glu Tyr Lys Ile Leu Glu Lys Met Pro Gln Thr Thr Ile
        210                 215                 220

Lys Glu Gly Glu Thr Glu Lys Lys Ile Val Ser Ile Lys Asn Phe Leu
225                 230                 235                 240

Glu Ser Glu Asn Lys Arg Thr Gly Ala Leu Gly Asn Leu Lys Asp Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Arg

<210> SEQ ID NO 45
<211> LENGTH: 326
<212> TYPE: PRT
<213> ORGANISM: Yersinia pseudotuberculosis

<400> SEQUENCE: 45

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Ile His Phe Ser Leu Thr Ala
            115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
```

```
                145                 150                 155                 160
Thr Ala Glu Leu Lys Ile Tyr Ser Val Ile Gln Ala Glu Ile Asn Lys
                    165                 170                 175

His Leu Ser Ser Gly Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Glu Gly Glu Thr Glu Lys Lys Ile Val Ser Ile Lys Asn Phe Leu
225                 230                 235                 240

Glu Ser Glu Lys Lys Arg Thr Gly Ala Leu Gly Asn Leu Lys Asp Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 46
<211> LENGTH: 326
<212> TYPE: PRT
<213> ORGANISM: Yersinia pseudotuberculosis

<400> SEQUENCE: 46

Met Ile Arg Ala Tyr Glu Gln Asn Pro Gln His Phe Ile Glu Asp Leu
  1               5                  10                  15

Glu Lys Val Arg Val Glu Gln Leu Thr Gly His Gly Ser Ser Val Leu
                20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
        50                  55                  60

Thr Asp Asp Ile Glu Leu Leu Lys Lys Ile Leu Ala Tyr Phe Leu Pro
 65                 70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
                100                 105                 110

Trp Glu Leu Arg Ala Phe Met Ala Val Ile His Phe Ser Leu Thr Ala
            115                 120                 125

Asp Arg Ile Asp Asp Ile Leu Lys Val Ile Val Asp Ser Met Asn
        130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Gly Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
```

```
                195                 200                 205

Ala Ser Ala Glu Tyr Lys Ile Leu Glu Lys Met Pro Gln Thr Thr Ile
    210                 215                 220

Gln Glu Gly Glu Thr Glu Lys Lys Ile Val Ser Ile Lys Asn Phe Leu
225                 230                 235                 240

Glu Ser Glu Lys Lys Arg Thr Gly Ala Leu Gly Asn Leu Lys Asp Ser
                    245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
                275                 280                 285

Thr Gln Leu Ser Asp Ile Thr Ser Arg Phe Asn Ser Ala Ile Glu Ala
                290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 47
<211> LENGTH: 326
<212> TYPE: PRT
<213> ORGANISM: Yersinia pestis

<400> SEQUENCE: 47

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
                20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
        50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
                135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
```

```
                        245                 250                 255
Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
            290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 48
<211> LENGTH: 324
<212> TYPE: PRT
<213> ORGANISM: Yersinia pestis biovar Microtus

<400> SEQUENCE: 48

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Gly Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
```

```
                290                 295                 300
Leu Asn Arg Phe Ile Gln Lys Tyr Asp Ser Val Met Gln Arg Leu Leu
305                 310                 315                 320

Asp Asp Thr Arg

<210> SEQ ID NO 49
<211> LENGTH: 324
<212> TYPE: PRT
<213> ORGANISM: Yersinia pestis biovar Microtus

<400> SEQUENCE: 49

Met Ile Arg Ala Tyr Glu Gln Asn Pro Gln His Phe Ile Glu Asp Leu
  1               5                  10                  15

Glu Lys Val Arg Val Glu Gln Leu Thr Gly His Gly Ser Ser Val Leu
             20                  25                  30

Glu Glu Leu Val Gln Leu Val Lys Asp Lys Asn Ile Asp Ile Ser Ile
         35                  40                  45

Lys Tyr Asp Pro Arg Lys Asp Ser Glu Val Phe Ala Asn Arg Val Ile
 50                  55                  60

Thr Asp Asp Ile Glu Leu Leu Lys Lys Ile Leu Ala Tyr Phe Leu Pro
 65                  70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Pro Asn Thr Gln
            100                 105                 110

Trp Glu Leu Arg Ala Phe Met Ala Val Met His Phe Ser Leu Thr Ala
            115                 120                 125

Asp Arg Ile Asp Asp Ile Leu Lys Val Ile Val Asp Ser Met Asn
130                 135                 140

His His Gly Asp Ala Arg Ser Lys Leu Arg Glu Gln Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
            195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Arg

<210> SEQ ID NO 50
<211> LENGTH: 326
```

```
<212> TYPE: PRT
<213> ORGANISM: Yersinia pestis biovar Mediaevalis

<400> SEQUENCE: 50

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
130                 135                 140

His His Gly Asp Ala Arg Ser Lys Leu Arg Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Ile Phe Lys
        195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 51
<211> LENGTH: 326
<212> TYPE: PRT
<213> ORGANISM: Yersinia pestis biovar Orientalis

<400> SEQUENCE: 51

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
```

```
                   20                  25                  30
Glu Glu Leu Val Gln Leu Val Lys Asp Lys Asn Ile Asp Ile Ser Ile
                35                  40                  45
Lys Tyr Asp Pro Arg Lys Asp Ser Glu Val Phe Ala Asn Arg Val Ile
            50                  55                  60
Thr Asp Asp Ile Glu Leu Leu Lys Lys Ile Leu Ala Tyr Phe Leu Pro
65                  70                  75                  80
Glu Asp Ala Ile Leu Lys Gly Gly His Tyr Asp Asn Gln Leu Gln Asn
                85                  90                  95
Gly Ile Lys Arg Val Lys Glu Phe Leu Glu Ser Ser Pro Asn Thr Gln
            100                 105                 110
Trp Glu Leu Arg Ala Phe Met Ala Val Met His Phe Ser Leu Thr Ala
            115                 120                 125
Asp Arg Ile Asp Asp Ile Leu Lys Val Ile Val Asp Ser Met Asn
            130                 135                 140
His His Gly Asp Ala Arg Ser Lys Leu Arg Glu Glu Leu Ala Glu Leu
145                 150                 155                 160
Thr Ala Glu Leu Lys Ile Tyr Ser Val Ile Gln Ala Glu Ile Asn Lys
                165                 170                 175
His Leu Ser Ser Ser Gly Thr Ile Asn Ile His Asp Lys Ser Ile Asn
                180                 185                 190
Leu Met Asp Lys Asn Leu Tyr Gly Tyr Thr Asp Glu Gly Ile Phe Lys
                195                 200                 205
Ala Ser Ala Glu Tyr Lys Ile Leu Glu Lys Met Pro Gln Thr Thr Ile
            210                 215                 220
Gln Val Asp Gly Ser Glu Lys Lys Ile Val Ser Ile Lys Asp Phe Leu
225                 230                 235                 240
Gly Ser Glu Asn Lys Arg Thr Gly Ala Leu Gly Asn Leu Lys Asn Ser
                245                 250                 255
Tyr Ser Tyr Asn Lys Asp Asn Asn Glu Leu Ser His Phe Ala Thr Thr
                260                 265                 270
Cys Ser Asp Lys Ser Arg Pro Leu Asn Asp Leu Val Ser Gln Lys Thr
            275                 280                 285
Thr Gln Leu Ser Asp Ile Thr Ser Arg Phe Asn Ser Ala Ile Glu Ala
            290                 295                 300
Leu Asn Arg Phe Ile Gln Lys Tyr Asp Ser Val Met Gln Arg Leu Leu
305                 310                 315                 320
Asp Asp Thr Ser Gly Lys
                325
```

<210> SEQ ID NO 52
<211> LENGTH: 326
<212> TYPE: PRT
<213> ORGANISM: Yersinia pestis biovar Orientalis

<400> SEQUENCE: 52

```
Met Ile Arg Ala Tyr Glu Gln Asn Pro Gln His Phe Ile Glu Asp Leu
1               5                   10                  15
Glu Lys Val Arg Val Glu Gln Leu Thr Gly His Gly Ser Ser Val Leu
                20                  25                  30
Glu Glu Leu Val Gln Leu Val Lys Asp Lys Asn Ile Asp Ile Ser Ile
                35                  40                  45
Lys Tyr Asp Pro Arg Lys Asp Ser Glu Val Phe Ala Asn Arg Val Ile
            50                  55                  60
Thr Asp Asp Ile Glu Leu Leu Lys Lys Ile Leu Ala Tyr Phe Leu Pro
```

```
                65                  70                  75                  80
Glu Asp Ala Ile Leu Lys Gly Gly His Tyr Asp Asn Gln Leu Gln Asn
                    85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 53
<211> LENGTH: 326
<212> TYPE: PRT
<213> ORGANISM: Yersinia pestis biovar Orientalis

<400> SEQUENCE: 53

Met Ile Arg Ala Tyr Glu Gln Asn Pro Gln His Phe Ile Glu Asp Leu
  1               5                  10                  15

Glu Lys Val Arg Val Glu Gln Leu Thr Gly His Gly Ser Ser Val Leu
                20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
        50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
```

```
            115                 120                 125
Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 54
<211> LENGTH: 306
<212> TYPE: PRT
<213> ORGANISM: Yersinia pestis biovar Antiqua

<400> SEQUENCE: 54

Met Glu Gln Leu Thr Gly His Gly Ser Ser Val Leu Glu Glu Leu Val
1               5                   10                  15

Gln Leu Val Lys Asp Lys Asn Ile Asp Ile Ser Ile Lys Tyr Asp Pro
            20                  25                  30

Arg Lys Asp Ser Glu Val Phe Ala Asn Arg Val Ile Thr Asp Asp Ile
        35                  40                  45

Glu Leu Leu Lys Lys Ile Leu Ala Tyr Phe Leu Pro Glu Asp Ala Ile
    50                  55                  60

Leu Lys Gly Gly His Tyr Asp Asn Gln Leu Gln Asn Gly Ile Lys Arg
65                  70                  75                  80

Val Lys Glu Phe Leu Glu Ser Ser Pro Asn Thr Gln Trp Glu Leu Arg
                85                  90                  95

Ala Phe Met Ala Val Met His Phe Ser Leu Thr Ala Asp Arg Ile Asp
            100                 105                 110

Asp Asp Ile Leu Lys Val Ile Val Asp Ser Met Asn His Gly Asp
        115                 120                 125

Ala Arg Ser Lys Leu Arg Glu Glu Leu Ala Glu Leu Thr Ala Glu Leu
    130                 135                 140

Lys Ile Tyr Ser Val Ile Gln Ala Glu Ile Asn Lys His Leu Ser Ser
145                 150                 155                 160

Ser Gly Thr Ile Asn Ile His Asp Lys Ser Ile Asn Leu Met Asp Lys
```

```
                165                 170                 175
Asn Leu Tyr Gly Tyr Thr Asp Glu Glu Ile Phe Lys Ala Ser Ala Glu
            180                 185                 190

Tyr Lys Ile Leu Glu Lys Met Pro Gln Thr Thr Ile Gln Val Asp Gly
        195                 200                 205

Ser Glu Lys Lys Ile Val Ser Ile Lys Asp Phe Leu Gly Ser Glu Asn
    210                 215                 220

Lys Arg Thr Gly Ala Leu Gly Asn Leu Lys Asn Ser Tyr Ser Tyr Asn
225                 230                 235                 240

Lys Asp Asn Asn Glu Leu Ser His Phe Ala Thr Thr Cys Ser Asp Lys
                245                 250                 255

Ser Arg Pro Leu Asn Asp Leu Val Ser Gln Lys Thr Thr Gln Leu Ser
            260                 265                 270

Asp Ile Thr Ser Arg Phe Asn Ser Ala Ile Glu Ala Leu Asn Arg Phe
        275                 280                 285

Ile Gln Lys Tyr Asp Ser Val Met Gln Arg Leu Leu Asp Asp Thr Ser
    290                 295                 300

Gly Lys
305

<210> SEQ ID NO 55
<211> LENGTH: 326
<212> TYPE: PRT
<213> ORGANISM: Yersinia pestis biovar Mediaevalis

<400> SEQUENCE: 55

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
```

```
                        225                 230                 235                 240
Gly Ser Glu Asn Lys Arg Thr Gly Ala Leu Gly Asn Leu Lys Asn Ser
                    245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 56
<211> LENGTH: 306
<212> TYPE: PRT
<213> ORGANISM: Yersinia pestis biovar Antiqua

<400> SEQUENCE: 56

Met Glu Gln Leu Thr Gly His Gly Ser Ser Val Leu Glu Glu Leu Val
 1               5                  10                  15

Gln Leu Val Lys Asp Lys Asn Ile Asp Ile Ser Ile Lys Tyr Asp Pro
            20                  25                  30

Arg Lys Asp Ser Glu Val Phe Ala Asn Arg Val Ile Thr Asp Asp Ile
        35                  40                  45

Glu Leu Leu Lys Lys Ile Leu Ala Tyr Phe Leu Pro Glu Asp Ala Ile
    50                  55                  60

Leu Lys Gly Gly His Tyr Asp Asn Gln Leu Gln Asn Gly Ile Lys Arg
65                  70                  75                  80

Val Lys Glu Phe Leu Glu Ser Ser Pro Asn Thr Gln Trp Glu Leu Arg
                85                  90                  95

Ala Phe Met Ala Val Met His Phe Ser Leu Thr Ala Asp Arg Ile Asp
            100                 105                 110

Asp Asp Ile Leu Lys Val Ile Val Asp Ser Met Asn His His Gly Asp
        115                 120                 125

Ala Arg Ser Lys Leu Arg Glu Glu Leu Ala Glu Leu Thr Ala Glu Leu
    130                 135                 140

Lys Ile Tyr Ser Val Ile Gln Ala Glu Ile Asn Lys His Leu Ser Ser
145                 150                 155                 160

Ser Gly Thr Ile Asn Ile His Asp Lys Ser Ile Asn Leu Met Asp Lys
                165                 170                 175

Asn Leu Tyr Gly Tyr Thr Asp Glu Glu Ile Phe Lys Ala Ser Ala Glu
            180                 185                 190

Tyr Lys Ile Leu Glu Lys Met Pro Gln Thr Thr Ile Gln Val Asp Gly
        195                 200                 205

Ser Glu Lys Lys Ile Val Ser Ile Lys Asp Phe Leu Gly Ser Glu Asn
    210                 215                 220

Lys Arg Thr Gly Ala Leu Gly Asn Leu Lys Asn Ser Tyr Ser Tyr Asn
225                 230                 235                 240

Lys Asp Asn Asn Glu Leu Ser His Phe Ala Thr Thr Cys Ser Asp Lys
                245                 250                 255

Ser Arg Pro Leu Asn Asp Leu Val Ser Gln Lys Thr Thr Gln Leu Ser
            260                 265                 270

Asp Ile Thr Ser Arg Phe Asn Ser Ala Ile Glu Ala Leu Asn Arg Phe
```

```
                  275                 280                 285
Ile Gln Lys Tyr Asp Ser Val Met Gln Arg Leu Leu Asp Asp Thr Ser
    290                 295                 300

Gly Lys
305

<210> SEQ ID NO 57
<211> LENGTH: 326
<212> TYPE: PRT
<213> ORGANISM: Yersinia pestis biovar Orientalis

<400> SEQUENCE: 57

Met Ile Arg Ala Tyr Glu Gln Asn Pro Gln His Phe Ile Glu Asp Leu
1               5                   10                  15

Glu Lys Val Arg Val Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325
```

```
<210> SEQ ID NO 58
<211> LENGTH: 326
<212> TYPE: PRT
<213> ORGANISM: Yersinia pestis biovar Orientalis

<400> SEQUENCE: 58

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 59
<211> LENGTH: 326
<212> TYPE: PRT
<213> ORGANISM: Yersinia pestis biovar Orientalis

<400> SEQUENCE: 59

Met Ile Arg Ala Tyr Glu Gln Asn Pro Gln His Phe Ile Glu Asp Leu
 1               5                  10                  15
```

```
Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
 50                  55                  60

Thr Asp Asp Ile Glu Leu Leu Lys Lys Ile Leu Ala Tyr Phe Leu Pro
 65                  70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Ser Pro Asn Thr Gln
                100                 105                 110

Trp Glu Leu Arg Ala Phe Met Ala Val Met His Phe Ser Leu Thr Ala
            115                 120                 125

Asp Arg Ile Asp Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Ile Phe Lys
            195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 60
<211> LENGTH: 326
<212> TYPE: PRT
<213> ORGANISM: Yersinia pestis biovar Antiqua

<400> SEQUENCE: 60

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
 50                  55                  60
```

```
Thr Asp Asp Ile Glu Leu Leu Lys Lys Ile Leu Ala Tyr Phe Leu Pro
 65                  70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 61
<211> LENGTH: 326
<212> TYPE: PRT
<213> ORGANISM: Yersinia pestis biovar Antiqua

<400> SEQUENCE: 61

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
                20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
        50                  55                  60

Thr Asp Asp Ile Glu Leu Leu Lys Lys Ile Leu Ala Tyr Phe Leu Pro
 65                 70                  75                  80

Glu Asp Ala Ile Leu Lys Gly Gly His Tyr Asp Asn Gln Leu Gln Asn
                 85                 90                  95

Gly Ile Lys Arg Val Lys Glu Phe Leu Glu Ser Ser Pro Asn Thr Gln
            100                 105                 110
```

```
Trp Glu Leu Arg Ala Phe Met Ala Val Met His Phe Ser Leu Thr Ala
            115                 120                 125
Asp Arg Ile Asp Asp Ile Leu Lys Val Ile Val Asp Ser Met Asn
    130                 135                 140
His His Gly Asp Ala Arg Ser Lys Leu Arg Glu Glu Leu Ala Glu Leu
145                 150                 155                 160
Thr Ala Glu Leu Lys Ile Tyr Ser Val Ile Gln Ala Glu Ile Asn Lys
                165                 170                 175
His Leu Ser Ser Ser Gly Thr Ile Asn Ile His Asp Lys Ser Ile Asn
            180                 185                 190
Leu Met Asp Lys Asn Leu Tyr Gly Tyr Thr Asp Glu Ile Phe Lys
    195                 200                 205
Ala Ser Ala Glu Tyr Lys Ile Leu Glu Lys Met Pro Gln Thr Thr Ile
            210                 215                 220
Gln Val Asp Gly Ser Glu Lys Lys Ile Val Ser Ile Lys Asp Phe Leu
225                 230                 235                 240
Gly Ser Glu Asn Lys Arg Thr Gly Ala Leu Gly Asn Leu Lys Asn Ser
                245                 250                 255
Tyr Ser Tyr Asn Lys Asp Asn Asn Glu Leu Ser His Phe Ala Thr Thr
            260                 265                 270
Cys Ser Asp Lys Ser Arg Pro Leu Asn Asp Leu Val Ser Gln Lys Thr
    275                 280                 285
Thr Gln Leu Ser Asp Ile Thr Ser Arg Phe Asn Ser Ala Ile Glu Ala
            290                 295                 300
Leu Asn Arg Phe Ile Gln Lys Tyr Asp Ser Val Met Gln Arg Leu Leu
305                 310                 315                 320
Asp Asp Thr Ser Gly Lys
                325

<210> SEQ ID NO 62
<211> LENGTH: 326
<212> TYPE: PRT
<213> ORGANISM: Yersinia pestis biovar Antiqua

<400> SEQUENCE: 62

Met Ile Arg Ala Tyr Glu Gln Asn Pro Gln His Phe Ile Glu Asp Leu
1               5                   10                  15
Glu Lys Val Arg Val Glu Gln Leu Thr Gly His Gly Ser Ser Val Leu
                20                  25                  30
Glu Glu Leu Val Gln Leu Val Lys Asp Lys Asn Ile Asp Ile Ser Ile
            35                  40                  45
Lys Tyr Asp Pro Arg Lys Asp Ser Glu Val Phe Ala Asn Arg Val Ile
    50                  55                  60
Thr Asp Asp Ile Glu Leu Leu Lys Lys Ile Leu Ala Tyr Phe Leu Pro
65                  70                  75                  80
Glu Asp Ala Ile Leu Lys Gly Gly His Tyr Asp Asn Gln Leu Gln Asn
                85                  90                  95
Gly Ile Lys Arg Val Lys Glu Phe Leu Glu Ser Ser Pro Asn Thr Gln
            100                 105                 110
Trp Glu Leu Arg Ala Phe Met Ala Val Met His Phe Ser Leu Thr Ala
            115                 120                 125
Asp Arg Ile Asp Asp Ile Leu Lys Val Ile Val Asp Ser Met Asn
    130                 135                 140
His His Gly Asp Ala Arg Ser Lys Leu Arg Glu Glu Leu Ala Glu Leu
145                 150                 155                 160
```

```
Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
            195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Ser Gly Lys
            325

<210> SEQ ID NO 63
<211> LENGTH: 326
<212> TYPE: PRT
<213> ORGANISM: Yersinia pestis biovar Antiqua

<400> SEQUENCE: 63

Met Ile Arg Ala Tyr Glu Gln Asn Pro Gln His Phe Ile Glu Asp Leu
  1               5                  10                  15

Glu Lys Val Arg Val Glu Gln Leu Thr Gly His Gly Ser Ser Val Leu
                 20                  25                  30

Glu Glu Leu Val Gln Leu Val Lys Asp Lys Asn Ile Asp Ile Ser Ile
             35                  40                  45

Lys Tyr Asp Pro Arg Lys Asp Ser Glu Val Phe Ala Asn Arg Val Ile
     50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Ser Pro Asn Thr Gln
                100                 105                 110

Trp Glu Leu Arg Ala Phe Met Ala Val Met His Phe Ser Leu Thr Ala
            115                 120                 125

Asp Arg Ile Asp Asp Ile Leu Lys Val Ile Val Asp Ser Met Asn
        130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
            195                 200                 205
```

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
                275                 280                 285

Thr Gln Leu Ser Asp Ile Thr Ser Arg Phe Asn Ser Ala Ile Glu Ala
                290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 64
<211> LENGTH: 326
<212> TYPE: PRT
<213> ORGANISM: Yersinia pestis biovar Orientalis

<400> SEQUENCE: 64

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
                20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
                100                 105                 110

Trp Glu Leu Arg Ala Phe Met Ala Val Met His Phe Ser Leu Thr Ala
            115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
                180                 185                 190

Leu Met Asp Lys Asn Leu Tyr Gly Tyr Thr Asp Glu Glu Ile Phe Lys
                195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
            290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 65
<211> LENGTH: 306
<212> TYPE: PRT
<213> ORGANISM: Yersinia pestis biovar Orientalis

<400> SEQUENCE: 65

Met Glu Gln Leu Thr Gly His Gly Ser Ser Val Leu Glu Glu Leu Val
1               5                   10                  15

Gln Leu Val Lys Asp Lys Asn Ile Asp Ile Ser Ile Lys Tyr Asp Pro
            20                  25                  30

Arg Lys Asp Ser Glu Val Phe Ala Asn Arg Val Ile Thr Asp Asp Ile
            35                  40                  45

Glu Leu Leu Lys Lys Ile Leu Ala Tyr Phe Leu Pro Glu Asp Ala Ile
            50                  55                  60

Leu Lys Gly Gly His Tyr Asp Asn Gln Leu Gln Asn Gly Ile Lys Arg
65                  70                  75                  80

Val Lys Glu Phe Leu Glu Ser Ser Pro Asn Thr Gln Trp Glu Leu Arg
            85                  90                  95

Ala Phe Met Ala Val Met His Phe Ser Leu Thr Ala Asp Arg Ile Asp
            100                 105                 110

Asp Asp Ile Leu Lys Val Ile Val Asp Ser Met Asn His His Gly Asp
            115                 120                 125

Ala Arg Ser Lys Leu Arg Glu Glu Leu Ala Glu Leu Thr Ala Glu Leu
            130                 135                 140

Lys Ile Tyr Ser Val Ile Gln Ala Glu Ile Asn Lys His Leu Ser Ser
145                 150                 155                 160

Ser Gly Thr Ile Asn Ile His Asp Lys Ser Ile Asn Leu Met Asp Lys
            165                 170                 175

Asn Leu Tyr Gly Tyr Thr Asp Glu Glu Ile Phe Lys Ala Ser Ala Glu
            180                 185                 190

Tyr Lys Ile Leu Glu Lys Met Pro Gln Thr Thr Ile Gln Val Asp Gly
            195                 200                 205

Ser Glu Lys Lys Ile Val Ser Ile Lys Asp Phe Leu Gly Ser Glu Asn
            210                 215                 220

Lys Arg Thr Gly Ala Leu Gly Asn Leu Lys Asn Ser Tyr Ser Tyr Asn
225                 230                 235                 240

Lys Asp Asn Asn Glu Leu Ser His Phe Ala Thr Thr Cys Ser Asp Lys
            245                 250                 255

Ser Arg Pro Leu Asn Asp Leu Val Ser Gln Lys Thr Thr Gln Leu Ser
            260                 265                 270

Asp Ile Thr Ser Arg Phe Asn Ser Ala Ile Glu Ala Leu Asn Arg Phe
            275                 280                 285

Ile Gln Lys Tyr Asp Ser Val Met Gln Arg Leu Leu Asp Thr Ser
            290                 295                 300

Gly Lys
305

<210> SEQ ID NO 66
<211> LENGTH: 306
<212> TYPE: PRT
<213> ORGANISM: Yersinia pestis biovar Orientalis

<400> SEQUENCE: 66

Met Glu Gln Leu Thr Gly His Gly Ser Ser Val Leu Glu Glu Leu Val
1               5                   10                  15

Gln Leu Val Lys Asp Lys Asn Ile Asp Ile Ser Ile Lys Tyr Asp Pro
            20                  25                  30

Arg Lys Asp Ser Glu Val Phe Ala Asn Arg Val Ile Thr Asp Asp Ile
        35                  40                  45

Glu Leu Leu Lys Lys Ile Leu Ala Tyr Phe Leu Pro Glu Asp Ala Ile
    50                  55                  60

Leu Lys Gly Gly His Tyr Asp Asn Gln Leu Gln Asn Gly Ile Lys Arg
65                  70                  75                  80

Val Lys Glu Phe Leu Glu Ser Ser Pro Asn Thr Gln Trp Glu Leu Arg
                85                  90                  95

Ala Phe Met Ala Val Met His Phe Ser Leu Thr Ala Asp Arg Ile Asp
            100                 105                 110

Asp Asp Ile Leu Lys Val Ile Val Asp Ser Met Asn His His Gly Asp
        115                 120                 125

Ala Arg Ser Lys Leu Arg Glu Glu Leu Ala Glu Leu Thr Ala Glu Leu
    130                 135                 140

Lys Ile Tyr Ser Val Ile Gln Ala Glu Ile Asn Lys His Leu Ser Ser
145                 150                 155                 160

Ser Gly Thr Ile Asn Ile His Asp Lys Ser Ile Asn Leu Met Asp Lys
                165                 170                 175

Asn Leu Tyr Gly Tyr Thr Asp Glu Glu Ile Phe Lys Ala Ser Ala Glu
            180                 185                 190

Tyr Lys Ile Leu Glu Lys Met Pro Gln Thr Thr Ile Gln Val Asp Gly
        195                 200                 205

Ser Glu Lys Lys Ile Val Ser Ile Lys Asp Phe Leu Gly Ser Glu Asn
    210                 215                 220

Lys Arg Thr Gly Ala Leu Gly Asn Leu Lys Asn Ser Tyr Ser Tyr Asn
225                 230                 235                 240

Lys Asp Asn Asn Glu Leu Ser His Phe Ala Thr Thr Cys Ser Asp Lys
                245                 250                 255

Ser Arg Pro Leu Asn Asp Leu Val Ser Gln Lys Thr Thr Gln Leu Ser
            260                 265                 270

Asp Ile Thr Ser Arg Phe Asn Ser Ala Ile Glu Ala Leu Asn Arg Phe
        275                 280                 285

Ile Gln Lys Tyr Asp Ser Val Met Gln Arg Leu Leu Asp Asp Thr Ser
    290                 295                 300

Gly Lys
305

<210> SEQ ID NO 67
<211> LENGTH: 326
<212> TYPE: PRT
<213> ORGANISM: Yersinia pestis biovar Orientalis

<400> SEQUENCE: 67

-continued

```
Met Ile Arg Ala Tyr Glu Gln Asn Pro Gln His Phe Ile Glu Asp Leu
 1               5                  10                 15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
         35                  40                  45

Lys Tyr Asp Pro Arg Lys Asp Ser Glu Val Phe Ala Asn Arg Val Ile
 50                  55                  60

Thr Asp Asp Ile Glu Leu Leu Lys Lys Ile Leu Ala Tyr Phe Leu Pro
 65                  70                  75                  80

Glu Asp Ala Ile Leu Lys Gly Gly His Tyr Asn Gln Leu Gln Asn
                 85                  90                  95

Gly Ile Lys Arg Val Lys Glu Phe Leu Glu Ser Ser Pro Asn Thr Gln
                100                 105                 110

Trp Glu Leu Arg Ala Phe Met Ala Val Met His Phe Ser Leu Thr Ala
            115                 120                 125

Asp Arg Ile Asp Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
                180                 185                 190

Leu Met Asp Lys Asn Leu Tyr Gly Tyr Thr Asp Glu Ile Phe Lys
            195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
            290                 295                 300

Leu Asn Arg Phe Ile Gln Lys Tyr Asp Ser Val Met Gln Arg Leu Leu
305                 310                 315                 320

Asp Asp Thr Ser Gly Lys
                325
```

<210> SEQ ID NO 68
<211> LENGTH: 326
<212> TYPE: PRT
<213> ORGANISM: Yersinia pestis Angola

<400> SEQUENCE: 68

```
Met Ile Arg Ala Tyr Glu Gln Asn Pro Gln His Phe Ile Glu Asp Leu
 1               5                  10                 15

Glu Asn Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
         35                  40                  45
```

```
Lys Tyr Asp Pro Arg Lys Asp Ser Glu Val Phe Ala Asn Arg Val Ile
 50                  55                  60

Thr Asp Asp Ile Glu Leu Leu Arg Lys Ile Leu Ala Tyr Phe Leu Pro
 65                      70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
                180                 185                 190

Leu Met Asp Lys Asn Leu Tyr Gly Tyr Thr Asp Glu Gly Ile Phe Lys
            195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Ser Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 69
<211> LENGTH: 326
<212> TYPE: PRT
<213> ORGANISM: Yersinia pestis Angola

<400> SEQUENCE: 69

Met Ile Arg Ala Tyr Glu Gln Asn Pro Gln His Phe Ile Glu Asp Leu
  1               5                  10                  15

Glu Asn Val Arg Val Glu Gln Leu Thr Gly His Gly Ser Ser Val Leu
                 20                  25                  30

Glu Glu Leu Val Gln Leu Val Lys Asp Lys Asn Ile Asp Ile Ser Ile
             35                  40                  45

Lys Tyr Asp Pro Arg Lys Asp Ser Glu Val Phe Ala Asn Arg Val Ile
 50                  55                  60

Thr Asp Asp Ile Glu Leu Leu Arg Lys Ile Leu Ala Tyr Phe Leu Pro
 65                      70                  75                  80

Glu Asp Ala Ile Leu Lys Gly Gly His Tyr Asp Asn Gln Leu Gln Asn
                 85                  90                  95
```

```
Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
            115                 120                 125

Asp Arg Ile Asp Asp Ile Leu Lys Val Ile Val Asp Ser Met Asn
130                 135                 140

His His Gly Asp Ala Arg Ser Lys Leu Arg Glu Gly Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
            195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Ser Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
            290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 70
<211> LENGTH: 326
<212> TYPE: PRT
<213> ORGANISM: Yersinia pestis CO92

<400> SEQUENCE: 70

Met Ile Arg Ala Tyr Glu Gln Asn Pro Gln His Phe Ile Glu Asp Leu
  1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
 50                  55                  60

Thr Asp Asp Ile Glu Leu Leu Lys Lys Ile Leu Ala Tyr Phe Leu Pro
 65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
            115                 120                 125

Asp Arg Ile Asp Asp Ile Leu Lys Val Ile Val Asp Ser Met Asn
130                 135                 140
```

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
            165                 170                 175

His Leu Ser Ser Ser Gly Thr Ile Asn Ile His Asp Lys Ser Ile Asn
        180                 185                 190

Leu Met Asp Lys Asn Leu Tyr Gly Tyr Thr Asp Glu Ile Phe Lys
        195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
            245                 250                 255

Tyr Ser Tyr Asn Lys Asp Asn Asn Glu Leu Ser His Phe Ala Thr Thr
        260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Ser Gly Lys
            325

<210> SEQ ID NO 71
<211> LENGTH: 324
<212> TYPE: PRT
<213> ORGANISM: Yersinia pestis subsp. caucasica

<400> SEQUENCE: 71

Met Ile Arg Ala Tyr Glu Gln Asn Pro Gln His Phe Ile Glu Asp Leu
 1               5                  10                  15

Glu Asn Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
50                  55                  60

Thr Asp Asp Ile Glu Leu Leu Arg Lys Ile Leu Ala Tyr Phe Leu Pro
65                  70                  75                  80

Glu Asp Ala Ile Leu Lys Gly Gly His Tyr Asp Asn Gln Leu Gln Asn
            85                  90                  95

Gly Ile Lys Arg Val Lys Gly Phe Leu Glu Ser Ser Pro Asn Thr Gln
        100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
            165                 170                 175

His Leu Ser Ser Ser Gly Thr Ile Asn Ile His Asp Lys Ser Ile Asn
        180                 185                 190

```
Leu Met Asp Lys Asn Leu Tyr Gly Tyr Thr Asp Glu Glu Ile Phe Lys
            195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Ser Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Arg

<210> SEQ ID NO 72
<211> LENGTH: 325
<212> TYPE: PRT
<213> ORGANISM: Yersinia pestis subsp. altaica

<400> SEQUENCE: 72

Met Pro Ala Tyr Glu Gln Asn Pro Gln His Phe Ile Glu Asp Leu Glu
  1               5                  10                  15

Asn Val Arg Val Glu Gln Leu Thr Gly His Gly Ser Ser Val Leu Glu
                 20                  25                  30

Glu Leu Val Gln Leu Val Lys Asp Lys Asn Ile Asp Ile Ser Ile Lys
             35                  40                  45

Tyr Asp Pro Arg Lys Asp Ser Glu Val Phe Ala Asn Arg Val Ile Thr
 50                  55                  60

Asp Asp Ile Glu Leu Leu Arg Lys Ile Leu Ala Tyr Phe Leu Pro Glu
65                  70                  75                  80

Asp Ala Ile Leu Lys Gly Gly His Tyr Asp Asn Gln Leu Gln Asn Gly
                 85                  90                  95

Ile Lys Arg Val Lys Glu Phe Leu Glu Ser Pro Asn Thr Gln Glu
            100                 105                 110

Glu Leu Arg Ala Phe Met Ala Val Met His Phe Ser Leu Thr Ala Asp
        115                 120                 125

Arg Ile Asp Asp Asp Ile Leu Lys Val Ile Val Asp Ser Met Asn His
130                 135                 140

His Gly Asp Ala Arg Ser Lys Leu Arg Glu Glu Leu Ala Glu Leu Thr
145                 150                 155                 160

Ala Glu Leu Lys Ile Tyr Ser Val Ile Gln Ala Glu Ile Asn Lys His
                165                 170                 175

Leu Ser Ser Ser Gly Thr Ile Asn Ile His Asp Lys Ser Ile Asn Leu
            180                 185                 190

Met Asp Lys Asn Leu Tyr Gly Tyr Thr Asp Glu Glu Ile Phe Lys Ala
        195                 200                 205

Ser Ala Glu Tyr Lys Ile Leu Glu Lys Met Pro Gln Thr Thr Ile Gln
    210                 215                 220

Val Asp Gly Ser Glu Lys Lys Ile Val Ser Ile Lys Asp Phe Leu Gly
225                 230                 235                 240

Ser Glu Asn Lys Arg Thr Gly Ala Leu Gly Asn Leu Lys Asn Ser Tyr
```

```
                        245                 250                 255
Ser Tyr Asn Lys Asp Asn Asn Glu Leu Ser His Phe Ala Thr Thr Ser
                260                 265                 270

Ser Asp Lys Ser Arg Pro Leu Asn Asp Leu Val Ser Gln Lys Thr Thr
            275                 280                 285

Gln Leu Ser Asp Ile Thr Ser Arg Phe Asn Ser Ala Ile Glu Ala Leu
        290                 295                 300

Asn Arg Phe Ile Gln Lys Tyr Asp Ser Val Met Gln Arg Leu Leu Asp
305                 310                 315                 320

Asp Thr Ser Gly Lys
                325

<210> SEQ ID NO 73
<211> LENGTH: 326
<212> TYPE: PRT
<213> ORGANISM: Yersinia pestis subsp. altaica

<400> SEQUENCE: 73

Met Ile Arg Ala Tyr Glu Gln Asn Pro Gln His Phe Ile Glu Asp Leu
1               5                   10                  15

Glu Asn Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Arg Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Gly Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Gly Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Ser Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
```

Leu Asn Arg Phe Ile Gln Lys Tyr Asp Ser Val Met Gln Arg Leu Leu
305                 310                 315                 320

Asp Asp Thr Ser Gly Lys
            325

<210> SEQ ID NO 74
<211> LENGTH: 326
<212> TYPE: PRT
<213> ORGANISM: Yersinia pestis subsp. ulegeica

<400> SEQUENCE: 74

Met Ile Ile Ala Tyr Glu Arg Asn Pro Gln His Phe Ile Glu Asp Leu
1               5                   10                  15

Glu Asn Val Arg Val Gln Leu Thr Gly His Gly Ser Ser Val Leu
            20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
    50                  55                  60

Thr Asp Asp Ile Glu Leu Leu Arg Lys Ile Leu Ala Tyr Phe Leu Pro
65                  70                  75                  80

Glu Asp Ala Leu Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
            325

```
<210> SEQ ID NO 75
<211> LENGTH: 326
<212> TYPE: PRT
<213> ORGANISM: Yersinia pestis subsp. ulegeica

<400> SEQUENCE: 75

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 76
<211> LENGTH: 324
<212> TYPE: PRT
<213> ORGANISM: Yersinia pestis subsp. hissarica

<400> SEQUENCE: 76

Met Ile Arg Ala Tyr Glu Gln Asn Pro Gln His Phe Ile Glu Asp Leu
1               5                   10                  15
```

Glu Asn Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
 50                  55                  60

Thr Asp Asp Ile Glu Leu Leu Arg Lys Ile Leu Ala Tyr Phe Leu Pro
 65                  70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
            115                 120                 125

Asp Arg Ile Asp Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Ile Phe Lys
            195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Ser Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
            290                 295                 300

Leu Asn Arg Phe Ile Gln Lys Tyr Asp Ser Val Met Gln Arg Leu Leu
305                 310                 315                 320

Asp Asp Thr Arg

<210> SEQ ID NO 77
<211> LENGTH: 326
<212> TYPE: PRT
<213> ORGANISM: Yersinia pestis CO92

<400> SEQUENCE: 77

Met Ile Arg Ala Tyr Glu Gln Asn Pro Gln His Phe Ile Glu Asp Leu
 1                   5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
 50                  55                  60

-continued

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 78
<211> LENGTH: 326
<212> TYPE: PRT
<213> ORGANISM: Yersinia pestis CA88-4125

<400> SEQUENCE: 78

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
                20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
        50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

-continued

Trp Glu Leu Arg Ala Phe Met Ala Val Met His Phe Ser Leu Thr Ala
    115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 79
<211> LENGTH: 326
<212> TYPE: PRT
<213> ORGANISM: Yersinia pestis KIM

<400> SEQUENCE: 79

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

```
Thr Ala Glu Leu Lys Ile Tyr Ser Val Ile Gln Ala Glu Ile Asn Lys
            165                 170                 175

His Leu Ser Ser Ser Gly Thr Ile Asn Ile His Asp Lys Ser Ile Asn
        180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
        210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 80
<211> LENGTH: 326
<212> TYPE: PRT
<213> ORGANISM: Yersinia pestis KIM

<400> SEQUENCE: 80

Met Ile Arg Ala Tyr Glu Gln Asn Pro Gln His Phe Ile Glu Asp Leu
1               5                   10                  15

Glu Lys Val Arg Val Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
        130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205
```

```
Ala Ser Ala Glu Tyr Lys Ile Leu Glu Lys Met Pro Gln Thr Thr Ile
        210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
                275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 81
<211> LENGTH: 324
<212> TYPE: PRT
<213> ORGANISM: Yersinia pestis subsp. caucasica

<400> SEQUENCE: 81

Met Ile Arg Ala Tyr Glu Gln Asn Pro Gln His Phe Ile Glu Asp Leu
  1               5                  10                  15

Glu Lys Val Arg Val Glu Gln Leu Thr Gly His Gly Ser Ser Val Leu
                 20                  25                  30

Glu Glu Leu Val Gln Leu Val Lys Asp Lys Asn Ile Asp Ile Ser Ile
             35                  40                  45

Lys Tyr Asp Pro Arg Lys Asp Ser Glu Val Phe Ala Asn Arg Val Ile
         50                  55                  60

Thr Asp Asp Ile Glu Leu Leu Lys Lys Ile Leu Ala Tyr Phe Leu Pro
 65                  70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Ser Pro Asn Thr Gln
                100                 105                 110

Trp Glu Leu Arg Ala Phe Met Ala Val Met His Phe Ser Leu Thr Ala
            115                 120                 125

Asp Arg Ile Asp Asp Ile Leu Lys Val Ile Val Asp Ser Met Asn
        130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
        210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255
```

```
Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Arg

<210> SEQ ID NO 82
<211> LENGTH: 326
<212> TYPE: PRT
<213> ORGANISM: Yersinia pestis subsp. pestis

<400> SEQUENCE: 82

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
```

Asp Asp Thr Ser Gly Lys
            325

<210> SEQ ID NO 83
<211> LENGTH: 326
<212> TYPE: PRT
<213> ORGANISM: Yersinia pestis subsp. pestis

<400> SEQUENCE: 83

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
            325

<210> SEQ ID NO 84
<211> LENGTH: 324
<212> TYPE: PRT

<213> ORGANISM: Yersinia pestis subsp. caucasica

<400> SEQUENCE: 84

```
Met Ile Arg Ala Tyr Glu Gln Asn Pro Gln His Phe Ile Glu Asp Leu
 1               5                  10                  15
Glu Lys Val Arg Val Glu Gln Leu Thr Gly His Gly Ser Ser Val Leu
            20                  25                  30
Glu Glu Leu Val Gln Leu Val Lys Asp Lys Asn Ile Asp Ile Ser Ile
        35                  40                  45
Lys Tyr Asp Pro Arg Lys Asp Ser Glu Val Phe Ala Asn Arg Val Ile
 50                  55                  60
Thr Asp Asp Ile Glu Leu Leu Lys Lys Ile Leu Ala Tyr Phe Leu Pro
 65                  70                  75                  80
Glu Asp Ala Ile Leu Lys Gly Gly His Tyr Asp Asn Gln Leu Gln Asn
                85                  90                  95
Gly Ile Lys Arg Val Lys Glu Phe Leu Glu Ser Ser Pro Asn Thr Gln
            100                 105                 110
Trp Glu Leu Arg Ala Phe Met Ala Val Met His Phe Ser Leu Thr Ala
        115                 120                 125
Asp Arg Ile Asp Asp Ile Leu Lys Val Ile Val Asp Ser Met Asn
130                 135                 140
His His Gly Asp Ala Arg Ser Lys Leu Arg Glu Glu Leu Ala Glu Leu
145                 150                 155                 160
Thr Ala Glu Leu Lys Ile Tyr Ser Val Ile Gln Ala Glu Ile Asn Lys
                165                 170                 175
His Leu Ser Ser Ser Gly Thr Ile Asn Ile His Asp Lys Ser Ile Asn
            180                 185                 190
Leu Met Asp Lys Asn Leu Tyr Gly Tyr Thr Asp Glu Gly Ile Phe Lys
        195                 200                 205
Ala Ser Ala Glu Tyr Lys Ile Leu Glu Lys Met Pro Gln Thr Thr Ile
    210                 215                 220
Gln Val Asp Gly Ser Glu Lys Lys Ile Val Ser Ile Lys Asp Phe Leu
225                 230                 235                 240
Gly Ser Glu Asn Lys Arg Thr Gly Ala Leu Gly Asn Leu Lys Asn Ser
                245                 250                 255
Tyr Ser Tyr Asn Lys Asp Asn Asn Glu Leu Ser His Phe Ala Thr Thr
            260                 265                 270
Cys Ser Asp Lys Ser Arg Pro Leu Asn Asp Leu Val Ser Gln Lys Thr
        275                 280                 285
Thr Gln Leu Ser Asp Ile Thr Ser Arg Phe Asn Ser Ala Ile Glu Ala
    290                 295                 300
Leu Asn Arg Phe Ile Gln Lys Tyr Asp Ser Val Met Gln Arg Leu Leu
305                 310                 315                 320
Asp Asp Thr Arg
```

<210> SEQ ID NO 85
<211> LENGTH: 326
<212> TYPE: PRT
<213> ORGANISM: Yersinia pestis CA88-4125

<400> SEQUENCE: 85

```
Met Ile Arg Ala Tyr Glu Gln Asn Pro Gln His Phe Ile Glu Asp Leu
 1               5                  10                  15
Glu Lys Val Arg Val Glu Gln Leu Thr Gly His Gly Ser Ser Val Leu
            20                  25                  30
```

```
Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
 50                  55                  60

Thr Asp Asp Ile Glu Leu Leu Lys Ile Leu Ala Tyr Phe Leu Pro
 65                  70                  75                  80

Glu Asp Ala Ile Leu Lys Gly Gly His Tyr Asp Asn Gln Leu Gln Asn
                    85                  90                  95

Gly Ile Lys Arg Val Lys Glu Phe Leu Glu Ser Ser Pro Asn Thr Gln
                100                 105                 110

Trp Glu Leu Arg Ala Phe Met Ala Val Met His Phe Ser Leu Thr Ala
                115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
                180                 185                 190

Leu Met Asp Lys Asn Leu Tyr Gly Tyr Thr Asp Glu Glu Ile Phe Lys
                195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
                275                 280                 285

Thr Gln Leu Ser Asp Ile Thr Ser Arg Phe Asn Ser Ala Ile Glu Ala
                290                 295                 300

Leu Asn Arg Phe Ile Gln Lys Tyr Asp Ser Val Met Gln Arg Leu Leu
305                 310                 315                 320

Asp Asp Thr Ser Gly Lys
                325
```

<210> SEQ ID NO 86
<211> LENGTH: 326
<212> TYPE: PRT
<213> ORGANISM: Yersinia pestis KIM

<400> SEQUENCE: 86

```
Met Ile Arg Ala Tyr Glu Gln Asn Pro Gln His Phe

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
            115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Ile Phe Lys
                195                 200                 205

Ala Ser Ala Glu Tyr Lys Ile Leu Glu Lys Met Pro Gln Thr Thr Ile
            210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 87
<211> LENGTH: 326
<212> TYPE: PRT
<213> ORGANISM: Yersinia pestis KIM

<400> SEQUENCE: 87

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
            115                 120                 125

Asp Arg Ile Asp Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 88
<211> LENGTH: 326
<212> TYPE: PRT
<213> ORGANISM: Yersinia pestis

<400> SEQUENCE: 88

Met Ile Arg Ala Tyr Glu Gln Asn Pro Gln His Phe Ile Glu Asp Leu
1               5                   10                  15

Glu Asn Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Arg Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

```
His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Ser Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 89
<211> LENGTH: 324
<212> TYPE: PRT
<213> ORGANISM: Yersinia pestis Pestoides F

<400> SEQUENCE: 89

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220
```

```
Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Arg

<210> SEQ ID NO 90
<211> LENGTH: 324
<212> TYPE: PRT
<213> ORGANISM: Yersinia enterocolitica subsp. enterocolitica 80

<400> SEQUENCE:

```
                275                 280                 285
Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Arg

<210> SEQ ID NO 91
<211> LENGTH: 324
<212> TYPE: PRT
<213> ORGANISM: Yersinia enterocolitica subsp. enterocolitica 8081

<400> SEQUENCE: 91

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
                20                  25                  30

Glu Glu Leu Val Gln Leu Val Lys Asp Lys Ile Asp Ile Ser

<210> SEQ ID NO 92
<211> LENGTH: 326
<212> TYPE: PRT
<213> ORGANISM: Yersinia pseudotuberculosis

<400> SEQUENCE: 92

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Ile His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Gly Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
    210                 215                 220

Gln Glu Gly Glu Thr Glu Lys Lys Ile Val Ser Ile Lys Asn Phe Leu
225                 230                 235                 240

Glu Ser Glu Lys Lys Arg Thr Gly Ala Leu Gly Asn Leu Lys Asp Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
    290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 93
<211> LENGTH: 326
<212> TYPE: PRT
<213> ORGANISM: Yersinia pseudotuberculosis

<400> SEQUENCE: 93

Met Ile Arg Ala Tyr Glu Gln Asn Pro Gln His Phe Ile Glu Asp Leu

```
                 1               5                  10                 15
Glu Lys Val Arg Val Glu Gln Leu Thr Gly His Gly Ser Ser Val Leu
                20                  25                 30

Glu Glu Leu Val Gln Leu Val Lys Asp Lys Asn Ile Asp Ile Ser Ile
                35                  40                 45

Lys Tyr Asp Pro Arg Lys Asp Ser Glu Val Phe Ala Asn Arg Val Ile
            50                  55                 60

Thr Asp Asp Ile Glu Leu Leu Lys Lys Ile Leu Ala Tyr Phe Leu Pro
65                  70                  75                 80

Glu Asp Ala Ile Leu Lys Gly Gly His Tyr Asp Asn Gln Leu Gln Asn
                85                  90                 95

Gly Ile Lys Arg Val Lys Glu Phe Leu Glu Ser Ser Pro Asn Thr Gln
                100                 105                110

Trp Glu Leu Arg Ala Phe Met Ala Val Ile His Phe Ser Leu Thr Ala
                115                 120                125

Asp Arg Ile Asp Asp Ile Leu Lys Val Ile Asp Ser Met Asn
                130                 135                140

His His Gly Asp Ala Arg Ser Lys Leu Arg Glu Glu Leu Ala Glu Leu
145                 150                 155                160

Thr Ala Glu Leu Lys Ile Tyr Ser Val Ile Gln Ala Glu Ile Asn Lys
                165                 170                175

His Leu Ser Ser Gly Gly Thr Ile Asn Ile His Asp Lys Ser Ile Asn
                180                 185                190

Leu Met Asp Lys Asn Leu Tyr Gly Tyr Thr Asp Glu Glu Ile Phe Lys
                195                 200                205

Ala Ser Ala Glu Tyr Lys Ile Leu Glu Lys Met Pro Gln Thr Thr Ile
                210                 215                220

Gln Glu Gly Glu Thr Glu Lys Lys Ile Val Ser Ile Lys Asn Phe Leu
225                 230                 235                240

Glu Ser Glu Lys Lys Arg Thr Gly Ala Leu Gly Asn Leu Lys Asp Ser
                245                 250                255

Tyr Ser Tyr Asn Lys Asp Asn Asn Glu Leu Ser His Phe Ala Thr Thr
                260                 265                270

Cys Ser Asp Lys Ser Arg Pro Leu Asn Asp Leu Val Ser Gln Lys Thr
                275                 280                285

Thr Gln Leu Ser Asp Ile Thr Ser Arg Phe Asn Ser Ala Ile Glu Ala
                290                 295                300

Leu Asn Arg Phe Ile Gln Lys Tyr Asp Ser Val Met Gln Arg Leu Leu
305                 310                 315                320

Asp Asp Thr Ser Gly Lys
                325

<210> SEQ ID NO 94
<211> LENGTH: 324
<212> TYPE: PRT
<213> ORGANISM: Yersinia pestis Pestoides F

<400> SEQUENCE: 94

Met Ile Arg Ala Tyr Glu Gln Asn Pro Gln His Phe Ile Glu Asp Leu
1               5                   10                 15

Glu Lys Val Arg Val Glu Gln Leu Thr Gly His Gly Ser Ser Val Leu
                20                  25                 30

Glu Glu Leu Val Gln Leu Val Lys Asp Lys Asn Ile Asp Ile Ser Ile
                35                  40                 45

Lys Tyr Asp Pro Arg Lys Asp Ser Glu Val Phe Ala Asn Arg Val Ile
```

```
                50                  55                  60
Thr Asp Asp Ile Glu Leu Leu Lys Lys Ile Leu Ala Tyr Phe Leu Pro
 65                  70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Ser Pro Asn Thr Gln
                100                 105                 110

Trp Glu Leu Arg Ala Phe Met Ala Val Met His Phe Ser Leu Thr Ala
                115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
                180                 185                 190

Leu Met Asp Lys Asn Leu Tyr Gly Tyr Thr Asp Glu Glu Ile Phe Lys
                195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
                275                 280                 285

Thr Gln Leu Ser Asp Ile Thr Ser Arg Phe Asn Ser Ala Ile Glu Ala
                290                 295                 300

Leu Asn Arg Phe Ile Gln Lys Tyr Asp Ser Val Met Gln Arg Leu Leu
305                 310                 315                 320

Asp Asp Thr Arg

<210> SEQ ID NO 95
<211> LENGTH: 326
<212> TYPE: PRT
<213> ORGANISM: Yersinia pestis Antiqua

<400> SEQUENCE: 95

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
                 20                  25                  30

Glu Glu Leu Val Gln Leu Val Lys Asp Lys Asn Ile Asp Ile Ser Ile
                 35                  40                  45

Lys Tyr Asp Pro Arg Lys Asp Ser Glu Val Phe Ala Asn Arg Val Ile
 50                  55                  60

Thr Asp Asp Ile Glu Leu Leu Lys Lys Ile Leu Ala Tyr Phe Leu Pro
 65                  70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Ser Pro Asn Thr Gln
                100                 105                 110
```

```
Trp Glu Leu Arg Ala Phe Met Ala Val Met His Phe Ser Leu Thr Ala
            115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Ile Phe Lys
        195                 200                 205

Ala Ser Ala Glu Tyr Lys Ile Leu Glu Lys Met Pro Gln Thr Thr Ile
    210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 96
<211> LENGTH: 326
<212> TYPE: PRT
<213> ORGANISM: Yersinia pestis Antiqua

<400> SEQUENCE: 96

Met Ile Arg Ala Tyr Glu Gln Asn Pro Gln His Phe Ile Glu Asp Leu
1               5                   10                  15

Glu Lys Val Arg Val Glu Gln Leu Thr Gly His Gly Ser Ser Val Leu
                20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
            115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160
```

Thr Ala Glu Leu Lys Ile Tyr Ser Val Ile Gln Ala Glu Ile Asn Lys
            165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
            195                 200                 205

Ala Ser Ala Glu Tyr Lys Ile Leu Glu Lys Met Pro Gln Thr Thr Ile
        210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 97
<211> LENGTH: 324
<212> TYPE: PRT
<213> ORGANISM: Yersinia pestis Pestoides F

<400> SEQUENCE: 97

Met Ile Arg Ala Tyr Glu Gln Asn Pro Gln His Phe Ile Glu Asp Leu
  1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
    50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
    130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
            165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
            195                 200                 205

```
Ala Ser Ala Glu Tyr Lys Ile Leu Glu Lys Met Pro Gln Thr Thr Ile
    210                 215                 220
Gln Val Asp Gly Ser Glu Lys Lys Ile Val Ser Ile Lys Asp Phe Leu
225                 230                 235                 240
Gly Ser Glu Asn Lys Arg Thr Gly Ala Leu Gly Asn Leu Lys Asn Ser
                245                 250                 255
Tyr Ser Tyr Asn Lys Asp Asn Asn Glu Leu Ser His Phe Ala Thr Thr
                260                 265                 270
Cys Ser Asp Lys Ser Arg Pro Leu Asn Asp Leu Val Ser Gln Lys Thr
                275                 280                 285
Thr Gln Leu Ser Asp Ile Thr Ser Arg Phe Asn Ser Ala Ile Glu Ala
                290                 295                 300
Leu Asn Arg Phe Ile Gln Lys Tyr Asp Ser Val Met Gln Arg Leu Leu
305                 310                 315                 320
Asp Asp Thr Arg

<210> SEQ ID NO 98
<211> LENGTH: 324
<212> TYPE: PRT
<213> ORGANISM: Yersinia pestis Pestoides F

<400> SEQUENCE: 98

Met Ile Arg Ala Tyr Glu Gln Asn Pro Gln His Phe Ile Glu Asp Leu
  1                 5                  10                  15
Glu Lys Val Arg Val Gln Leu Thr Gly His Gly Ser Ser Val Leu
                 20                  25                  30
Glu Glu Leu Val Gln Leu Val Lys Asp Lys Asn Ile Asp Ile Ser Ile
             35                  40                  45
Lys Tyr Asp Pro Arg Lys Asp Ser Glu Val Phe Ala Asn Arg Val Ile
         50                  55                  60
Thr Asp Asp Ile Glu Leu Leu Lys Lys Ile Leu Ala Tyr Phe Leu Pro
 65                  70                  75                  80
Glu Asp Ala Ile Leu Lys Gly Gly His Tyr Asp Asn Gln Leu Gln Asn
                 85                  90                  95
Gly Ile Lys Arg Val Lys Glu Phe Leu Glu Ser Ser Pro Asn Thr Gln
                100                 105                 110
Trp Glu Leu Arg Ala Phe Met Ala Val Met His Phe Ser Leu Thr Ala
            115                 120                 125
Asp Arg Ile Asp Asp Ile Leu Lys Val Ile Val Asp Ser Met Asn
        130                 135                 140
His His Gly Asp Ala Arg Ser Lys Leu Arg Glu Glu Leu Ala Glu Leu
145                 150                 155                 160
Thr Ala Glu Leu Lys Ile Tyr Ser Val Ile Gln Ala Glu Ile Asn Lys
                165                 170                 175
His Leu Ser Ser Ser Gly Thr Ile Asn Ile His Asp Lys Ser Ile Asn
                180                 185                 190
Leu Met Asp Lys Asn Leu Tyr Gly Tyr Thr Asp Glu Glu Ile Phe Lys
                195                 200                 205
Ala Ser Ala Glu Tyr Lys Ile Leu Glu Lys Met Pro Gln Thr Thr Ile
    210                 215                 220
Gln Val Asp Gly Ser Glu Lys Lys Ile Val Ser Ile Lys Asp Phe Leu
225                 230                 235                 240
Gly Ser Glu Asn Lys Arg Thr Gly Ala Leu Gly Asn Leu Lys Asn Ser
                245                 250                 255
```

```
Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Arg

<210> SEQ ID NO 99
<211> LENGTH: 326
<212> TYPE: PRT
<213> ORGANISM: Artificial Sequence
<220> FEATURE:
<223> OTHER INFORMATION: Synthetic construct-immunomodulator V

<400> SEQUENCE: 99

Met Ile Arg Ala Tyr Glu Gln Asn Pro Gln His Phe Ile Glu Asp Leu
 1               5                  10                  15

Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
        35                  40                  45

Lys Tyr Asp Pro Arg Lys Asp Ser Glu Val Phe Ala Asn Arg Val Ile
 50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Met His Phe Ser Leu Thr Ala
        115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
290                 295                 300
```

```
Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 100
<211> LENGTH: 326
<212> TYPE: PRT
<213> ORGANISM: Yersinia pseudotuberculosis PB1/+

<400> SEQUENCE: 100

Met Ile Arg Ala Tyr Glu Gln Asn Pro Gln His Phe Ile Glu Asp Leu
  1               5                  10                  15

Glu Lys Val Arg Val Glu Gln Leu Thr Gly His Gly Ser Ser Val Leu
             20                  25                  30

Glu Glu Leu Val Gln Leu Val Lys Asp Lys Asn Ile Asp Ile Ser Ile
         35                  40                  45

Lys Tyr Asp Pro Arg Lys Asp Ser Glu Val Phe Ala Asn Arg Val Ile
 50                  55                  60

Thr Asp Asp Ile Glu Leu Leu Lys Lys Ile Leu Ala Tyr Phe Leu Pro
 65                  70                  75                  80

Glu Asp Ala Ile Leu Lys Gly Gly His Tyr Asp Asn Gln Leu Gln Asn
                 85                  90                  95

Gly Ile Lys Arg Val Lys Glu Phe Leu Glu Ser Ser Pro Asn Thr Gln
            100                 105                 110

Trp Glu Leu Arg Ala Phe Met Ala Val Ile His Phe Ser Leu Thr Ala
        115                 120                 125

Asp Arg Ile Asp Asp Ile Leu Lys Val Ile Val Asp Ser Met Asn
130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Gly Gly Thr Ile Asn Ile His Asp Lys Ser Ile Asn
            180                 185                 190

Leu Met Asp Lys Asn Leu Tyr Gly Tyr Thr Asp Glu Glu Ile Phe Lys
        195                 200                 205

Ala Ser Ala Glu Tyr Lys Ile Leu Glu Lys Met Pro Gln Thr Thr Ile
210                 215                 220

Gln Glu Gly Glu Thr Glu Lys Lys Ile Val Ser Ile Lys Asn Phe Leu
225                 230                 235                 240

Glu Ser Glu Lys Lys Arg Thr Gly Ala Leu Gly Asn Leu Lys Asp Ser
                245                 250                 255

Tyr Ser Tyr Asn Lys Asp Asn Asn Glu Leu Ser His Phe Ala Thr Thr
            260                 265                 270

Cys Ser Asp Lys Ser Arg Pro Leu Asn Asp Leu Val Ser Gln Lys Thr
        275                 280                 285

Thr Gln Leu Ser Asp Ile Thr Ser Arg Phe Asn Ser Ala Ile Glu Ala
290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 101
```

<211> LENGTH: 326
<212> TYPE: PRT
<213> ORGANISM: Yersinia pseudotuberculosis PB1/+

<400> SEQUENCE: 101

| | | | | | | | | | | | | | | |
|---|---|---|---|---|---|---|---|---|---|---|---|---|---|---|
| Met | Ile | Arg | Ala | Tyr | Glu | Gln | Asn | Pro | Gln | His | Phe | Ile | Glu | Asp | Leu |
| 1 | | | | 5 | | | | | 10 | | | | | 15 | |

| Glu | Lys | Val | Arg | Val | Glu | Gln | Leu | Thr | Gly | His | Gly | Ser | Ser | Val | Leu |
|---|---|---|---|---|---|---|---|---|---|---|---|---|---|---|---|
| | | | 20 | | | | | 25 | | | | | 30 | | |

| Glu | Glu | Leu | Val | Gln | Leu | Val | Lys | Asp | Lys | Asn | Ile | Asp | Ile | Ser | Ile |
|---|---|---|---|---|---|---|---|---|---|---|---|---|---|---|---|
| | | | | 35 | | | | | 40 | | | | | 45 | |

| Lys | Tyr | Asp | Pro | Arg | Lys | Asp | Ser | Glu | Val | Phe | Ala | Asn | Arg | Val | Ile |
|---|---|---|---|---|---|---|---|---|---|---|---|---|---|---|---|
| | 50 | | | | | 55 | | | | | 60 | | | | |

| Thr | Asp | Asp | Ile | Glu | Leu | Leu | Lys | Lys | Ile | Leu | Ala | Tyr | Phe | Leu | Pro |
|---|---|---|---|---|---|---|---|---|---|---|---|---|---|---|---|
| 65 | | | | | 70 | | | | | 75 | | | | | 80 |

| Glu | Asp | Ala | Ile | Leu | Lys | Gly | Gly | His | Tyr | Asp | Asn | Gln | Leu | Gln | Asn |
|---|---|---|---|---|---|---|---|---|---|---|---|---|---|---|---|
| | | | | 85 | | | | | 90 | | | | | 95 | |

| Gly | Ile | Lys | Arg | Val | Lys | Glu | Phe | Leu | Glu | Ser | Ser | Pro | Asn | Thr | Gln |
|---|---|---|---|---|---|---|---|---|---|---|---|---|---|---|---|
| | | | 100 | | | | | 105 | | | | | 110 | | |

| Trp | Glu | Leu | Arg | Ala | Phe | Met | Ala | Val | Ile | His | Phe | Ser | Leu | Thr | Ala |
|---|---|---|---|---|---|---|---|---|---|---|---|---|---|---|---|
| | | 115 | | | | | 120 | | | | | 125 | | | |

| Asp | Arg | Ile | Asp | Asp | Ile | Leu | Lys | Val | Ile | Val | Asp | Ser | Met | Asn |
|---|---|---|---|---|---|---|---|---|---|---|---|---|---|---|
| 130 | | | | | 135 | | | | | 140 | | | | |

| His | His | Gly | Asp | Ala | Arg | Ser | Lys | Leu | Arg | Glu | Glu | Leu | Ala | Glu | Leu |
|---|---|---|---|---|---|---|---|---|---|---|---|---|---|---|---|
| 145 | | | | | 150 | | | | | 155 | | | | | 160 |

| Thr | Ala | Glu | Leu | Lys | Ile | Tyr | Ser | Val | Ile | Gln | Ala | Glu | Ile | Asn | Lys |
|---|---|---|---|---|---|---|---|---|---|---|---|---|---|---|---|
| | | | | 165 | | | | | 170 | | | | | 175 | |

| His | Leu | Ser | Ser | Gly | Gly | Thr | Ile | Asn | Ile | His | Asp | Lys | Ser | Ile | Asn |
|---|---|---|---|---|---|---|---|---|---|---|---|---|---|---|---|
| | | | 180 | | | | | 185 | | | | | 190 | | |

| Leu | Met | Asp | Lys | Asn | Leu | Tyr | Gly | Tyr | Thr | Asp | Glu | Glu | Ile | Phe | Lys |
|---|---|---|---|---|---|---|---|---|---|---|---|---|---|---|---|
| | | 195 | | | | | 200 | | | | | 205 | | | |

| Ala | Ser | Ala | Glu | Tyr | Lys | Ile | Leu | Glu | Lys | Met | Pro | Gln | Thr | Thr | Ile |
|---|---|---|---|---|---|---|---|---|---|---|---|---|---|---|---|
| 210 | | | | | 215 | | | | | 220 | | | | | |

| Gln | Glu | Gly | Glu | Thr | Lys | Lys | Ile | Val | Ser | Ile | Lys | Asn | Phe | Leu |
|---|---|---|---|---|---|---|---|---|---|---|---|---|---|---|
| 225 | | | | | 230 | | | | | 235 | | | | | 240 |

| Glu | Ser | Glu | Lys | Lys | Arg | Thr | Gly | Ala | Leu | Gly | Asn | Leu | Lys | Asp | Ser |
|---|---|---|---|---|---|---|---|---|---|---|---|---|---|---|---|
| | | | | 245 | | | | | 250 | | | | | 255 | |

| Tyr | Ser | Tyr | Asn | Lys | Asp | Asn | Asn | Glu | Leu | Ser | His | Phe | Ala | Thr | Thr |
|---|---|---|---|---|---|---|---|---|---|---|---|---|---|---|---|
| | | | 260 | | | | | 265 | | | | | 270 | | |

| Cys | Ser | Asp | Lys | Ser | Arg | Pro | Leu | Asn | Asp | Leu | Val | Ser | Gln | Lys | Thr |
|---|---|---|---|---|---|---|---|---|---|---|---|---|---|---|---|
| | | 275 | | | | | 280 | | | | | 285 | | | |

| Thr | Gln | Leu | Ser | Asp | Ile | Thr | Ser | Arg | Phe | Asn | Ser | Ala | Ile | Glu | Ala |
|---|---|---|---|---|---|---|---|---|---|---|---|---|---|---|---|
| | 290 | | | | | 295 | | | | | 300 | | | | |

| Leu | Asn | Arg | Phe | Ile | Gln | Lys | Tyr | Asp | Ser | Val | Met | Gln | Arg | Leu | Leu |
|---|---|---|---|---|---|---|---|---|---|---|---|---|---|---|---|
| 305 | | | | | 310 | | | | | 315 | | | | | 320 |

| Asp | Asp | Thr | Ser | Gly | Lys |
|---|---|---|---|---|---|
| | | | | 325 | |

<210> SEQ ID NO 102
<211> LENGTH: 329
<212> TYPE: PRT
<213> ORGANISM: Artificial Sequence
<220> FEATURE:
<223> OTHER INFORMATION: Synthetic construct-derived from Yersinia pestis

<400> SEQUENCE: 102

```
Lys Leu Ser Gly Ile Arg Ala Tyr Glu Gln Asn Pro Gln His Phe Ile
1               5                   10                  15

Glu Asp Leu Glu Lys Val Arg Val Glu Gln Leu Thr Gly His Gly Ser
            20                  25                  30

Ser Val Leu Glu Glu Leu Val Gln Leu Val Lys Asp Lys Asn Ile Asp
        35                  40                  45

Ile Ser Ile Lys Tyr Asp Pro Arg Lys Asp Ser Glu Val Phe Ala Asn
    50                  55                  60

Arg Val Ile Thr Asp Asp Ile Glu Leu Leu Lys Lys Ile Leu Ala Tyr
65                  70                  75                  80

Phe Leu Pro Glu Asp Ala Ile Leu Lys Gly Gly His Tyr Asp Asn Gln
                85                  90                  95

Leu Gln Asn Gly Ile Lys Arg Val Lys Glu Phe Leu Glu Ser Ser Pro
            100                 105                 110

Asn Thr Gln Trp Glu Leu Arg Ala Phe Met Ala Val Met His Phe Ser
        115                 120                 125

Leu Thr Ala Asp Arg Ile Asp Asp Ile Leu Lys Val Ile Val Asp
130                 135                 140

Ser Met Asn His His Gly Asp Ala Arg Ser Lys Leu Arg Glu Glu Leu
145                 150                 155                 160

Ala Glu Leu Thr Ala Glu Leu Lys Ile Tyr Ser Val Ile Gln Ala Glu
                165                 170                 175

Ile Asn Lys His Leu Ser Ser Gly Thr Ile Asn Ile His Asp Lys
            180                 185                 190

Ser Ile Asn Leu Met Asp Lys Asn Leu Tyr Gly Tyr Thr Asp Glu Glu
        195                 200                 205

Ile Phe Lys Ala Ser Ala Glu Tyr Lys Ile Leu Glu Lys Met Pro Gln
    210                 215                 220

Thr Thr Ile Gln Val Asp Gly Ser Glu Lys Lys Ile Val Ser Ile Lys
225                 230                 235                 240

Asp Phe Leu Gly Ser Glu Asn Lys Arg Thr Gly Ala Leu Gly Asn Leu
                245                 250                 255

Lys Asn Ser Tyr Ser Tyr Asn Lys Asp Asn Asn Glu Leu Ser His Phe
            260                 265                 270

Ala Thr Thr Cys Ser Asp Lys Ser Arg Pro Leu Asn Asp Leu Val Ser
        275                 280                 285

Gln Lys Thr Thr Gln Leu Ser Asp Ile Thr Ser Arg Phe Asn Ser Ala
    290                 295                 300

Ile Glu Ala Leu Asn Arg Phe Ile Gln Lys Tyr Asp Ser Val Met Gln
305                 310                 315                 320

Arg Leu Leu Asp Asp Thr Ser Gly Lys
                325
```

<210> SEQ ID NO 103
<211> LENGTH: 326
<212> TYPE: PRT
<213> ORGANISM: Artificial Sequence
<220> FEATURE:
<223> OTHER INFORMATION: Synthetic construct

<400> SEQUENCE: 103

```
Met Ile Arg Ala Tyr Glu Gln Asn Pro Gln His Phe Ile Glu Asp Leu
1               5                   10                  15
```

```
Glu Lys Val Arg Val Glu Gln Leu Thr Gly His Gly Ser Ser Val Leu
            20                  25                  30

Glu Glu Leu Val Gln Leu Val Lys Asp Lys Asn Ile Asp Ile Ser Ile
            35                  40                  45

Lys Tyr Asp Pro Arg Lys Asp Ser Glu Val Phe Ala Asn Arg Val Ile
        50                  55                  60

Thr Asp Asp Ile Glu Leu Leu Lys Lys Ile Leu Ala Tyr Phe Leu Pro
65                  70                  75                  80

Glu Asp Ala Ile Leu Lys Gly Gly His Tyr Asp Asn Gln Leu Gln Asn
                85                  90                  95

Gly Ile Lys Arg Val Lys Glu Phe Leu Glu Ser Ser Pro Asn Thr Gln
                100                 105                 110

Trp Glu Leu Arg Ala Phe Met Ala Val Met His Phe Ser Leu Thr Ala
            115                 120                 125

Asp Arg Ile Asp Asp Asp Ile Leu Lys Val Ile Val Asp Ser Met Asn
        130                 135                 140

His His Gly Asp Ala Arg Ser Lys Leu Arg Glu Glu Leu Ala Glu Leu
145                 150                 155                 160

Thr Ala Glu Leu Lys Ile Tyr Ser Val Ile Gln Ala Glu Ile Asn Lys
                165                 170                 175

His Leu Ser Ser Ser Gly Thr Ile Asn Ile His Asp Lys Ser Ile Asn
                180                 185                 190

Leu Met Asp Lys Asn Leu Tyr Gly Tyr Thr Asp Glu Glu Ile Phe Lys
            195                 200                 205

Ala Ser Ala Glu Tyr Lys Ile Leu Glu Lys Met Pro Gln Thr Thr Ile
        210                 215                 220

Gln Val Asp Gly Ser Glu Lys Lys Ile Val Ser Ile Lys Asp Phe Leu
225                 230                 235                 240

Gly Ser Glu Asn Lys Arg Thr Gly Ala Leu Gly Asn Leu Lys Asn Ser
                245                 250                 255

Tyr Ser Tyr Asn Lys Asp Asn Asn Glu Leu Ser His Phe Ala Thr Thr
                260                 265                 270

Cys Ser Asp Lys Ser Arg Pro Leu Asn Asp Leu Val Ser Gln Lys Thr
            275                 280                 285

Thr Gln Leu Ser Asp Ile Thr Ser Arg Phe Asn Ser Ala Ile Glu Ala
        290                 295                 300

Leu Asn Arg Phe Ile Gln Lys Tyr Asp Ser Val Met Gln Arg Leu Leu
305                 310                 315                 320

Asp Asp Thr Ser Gly Lys
                325

<210> SEQ ID NO 104
<211> LENGTH: 8
<212> TYPE: DNA
<213> ORGANISM: Artificial Sequence
<220> FEATURE:
<223> OTHER INFORMATION: Synthetic oligonucleotide

<400> SEQUENCE: 104 ttaattaa                                                                8
```

YERSINIA PESTIS ANTIGENS, VACCINE COMPOSITIONS, AND RELATED METHODS

CROSS-REFERENCE TO RELATED APPLICATIONS

This application claims priority under 35 U.S.C. §119(e) to U.S. provisional patent application, U.S. Ser. No. 60/949,115, filed Jul. 11, 2007 ("the '115 application"). The entire contents of the '115 application are incorporated herein by reference.

BACKGROUND OF THE INVENTION

Historically plague has been a major infectious disease afflicting human populations, leading to millions of deaths. The etiologic agent of plague is *Yersinia pestis* and infection with this pathogen can develop into a highly contagious pneumonic disease with almost 100% lethality. Continued outbreaks of plague, along with the suitability of *Y. pestis* for weaponization has heightened interest in developing a vaccine. Currently, there is no safe and effective vaccine against *Y. pestis*.

Thus, there is a need to provide sources of vaccines and antigens for production of vaccines. Improved vaccine design and development, as well as methods of making and using such compositions of matter are needed which provide inexpensive and highly accessible sources of such therapeutic and/or prophylactic compositions.

SUMMARY OF THE INVENTION

The present invention provides *Yersinia pestis* antigens and vaccine components produced in plants. The present invention provides one or more *Y. pestis* antigens generated as a fusion with a thermostable protein (e.g. lichenase). The invention provides vaccine compositions containing *Y. pestis* antigens. Furthermore, the invention provides *Y. pestis* vaccines comprising at least two different *Y. pestis* antigens. In some embodiments, compositions in accordance with the invention include one or more plant components. Still further provided are methods for production and use of antigen and vaccine compositions in accordance with the invention.

BRIEF DESCRIPTION OF THE DRAWING

FIG. 3. Antibody responses elicited by plant-produced plague vaccine antigens and their protective efficacy against *Y. pestis* challenge. Serum samples were tested by ELISA for the presence of LcrV- (A and C) and F1- (B and D) specific IgG (A and C) and IgA (B and D). Data are represented as average titer±standard deviation. Animals were challenged with 100×LD$_{50}$ aerosolized *Y. pestis*, and the percent survivors for each experimental group were graphed over time (E).

FIG. 5. Antibody responses elicited by plant-produced plague vaccine antigens and their protective efficacy against *Y. pestis* challenge. Serum samples were tested by ELISA for the presence of LcrV- (A and C) and F1- (B and D) specific IgG. Data are represented as average titer±standard deviation. The graphs shown in (A) and (B) differ from those in (C) and (D) only in the scale of the Y-axis.

DEFINITIONS

Figure 1C:
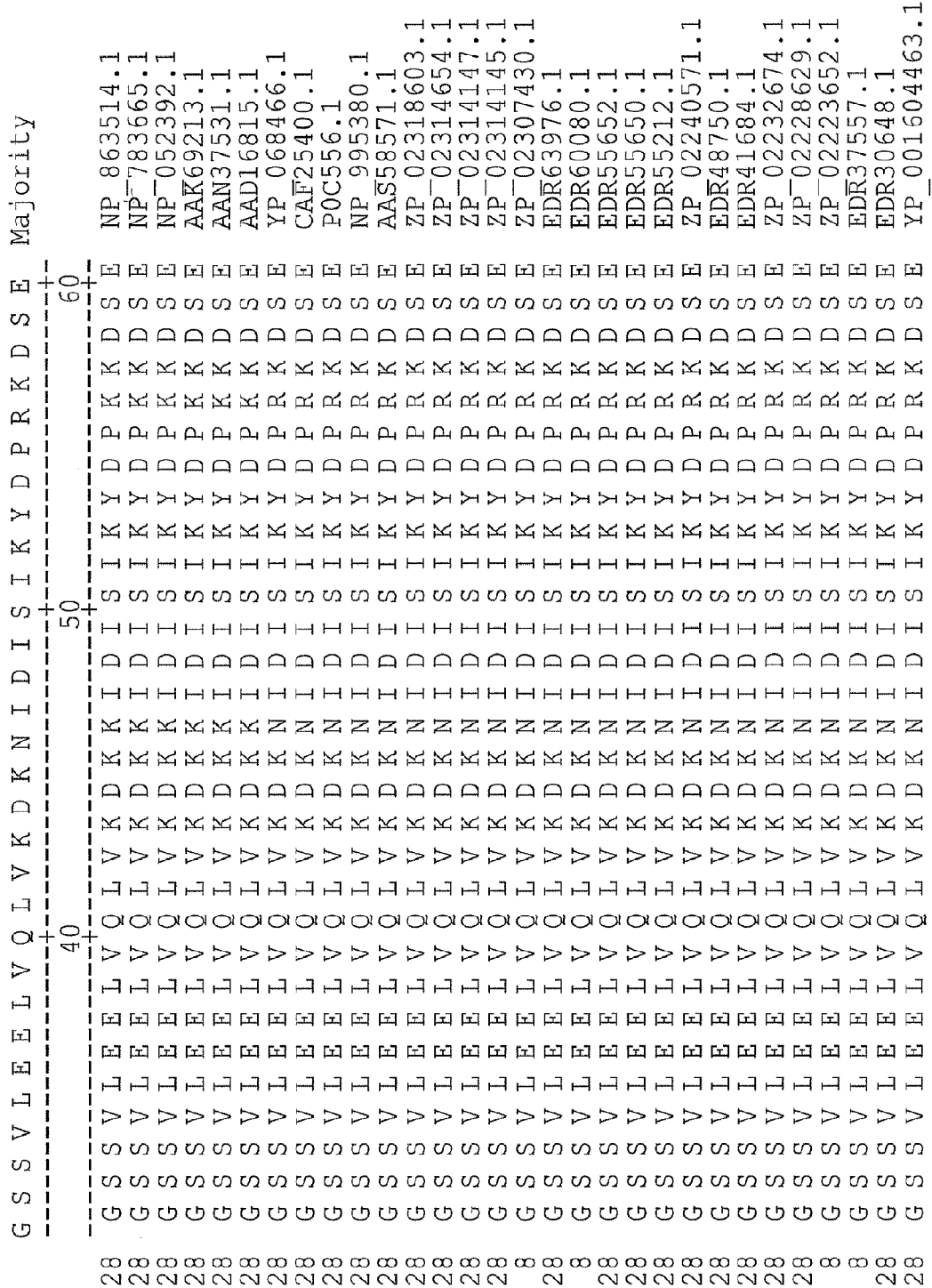
FIGS. 1a-1x. Alignment of amino acid sequences of LcrV protein from multiple *Y. pestis* strains. CLUSTAL W multiple sequence alignments of LcrV amino acid sequences from 64 different *Y. pestis* strains (GenBank accession numbers NP_863514.1; NP_783665.1; NP_052392.1; AAK69213.1; AAN37531.1; AAD16815.1; YP_068466.1; CAF25400.1; P00556.1; NP_995380.1; AAS58571.1; ZP_02318603.1; ZP_02314654.1; ZP_02314147.1; ZP_02314145.1; ZP_02307430.1; EDR63976.1; EDR60080.1; EDR55652.1; EDR55650.1; EDR55212.1; ZP_02240571.1; EDR48750.1; EDR41684.1; ZP_02232674.1; ZP_02228629.1; ZP_02223652.1; EDR37557.1; EDR30648.1; YP_001604463.1; ABX88711.1; CAB54908.1; ABF48194.1; ABF48193.1; ABF48192.1; ABF48191.1; ABF48190.1; ABF48189.1; NP_395165.1; YP_001293940.1; NP_857946.1; NP_857751.1; ABR68791.1; ABR68790.1; ABR68789.1; ABR68788.1; ABR14856.1; AAC69799.1; AAC62574.1; AAF64077.1; A4TSQ1.1; YP_001004069.1; CAL10039.1; P23994.1; AAA27645.1; AAF64076.1; YP_636823.1; ABG16274.1; ABP42325.1; YP_001154615.1; ABB16313.1; YP_001874676.1; ACC91219.1; ABI97154.1) aligned with the sequence of LcrV that was used in the production of antigen constructs in the Exemplification ("LcrV.pro").
Figure 1E:
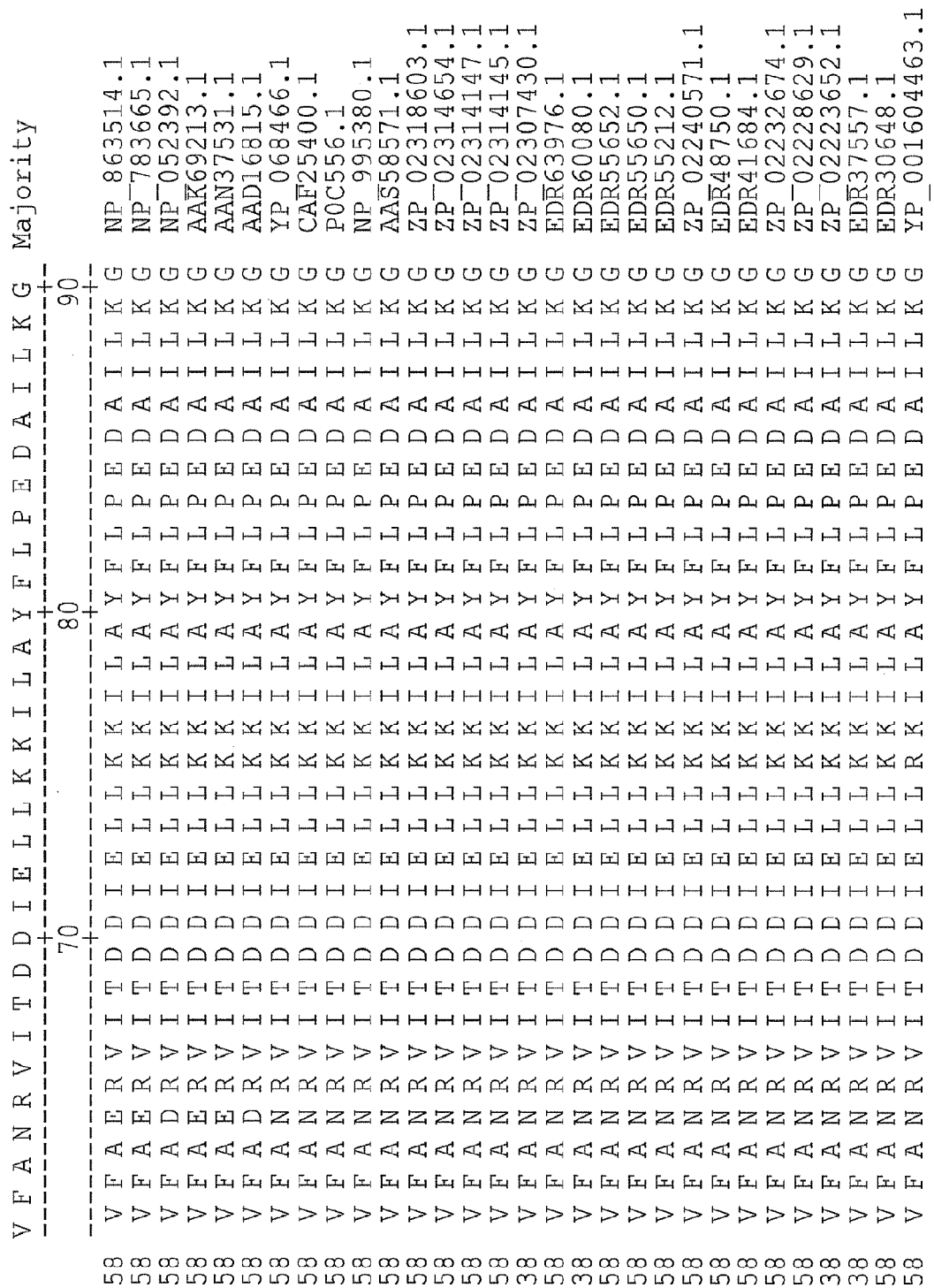
Figure 1I:
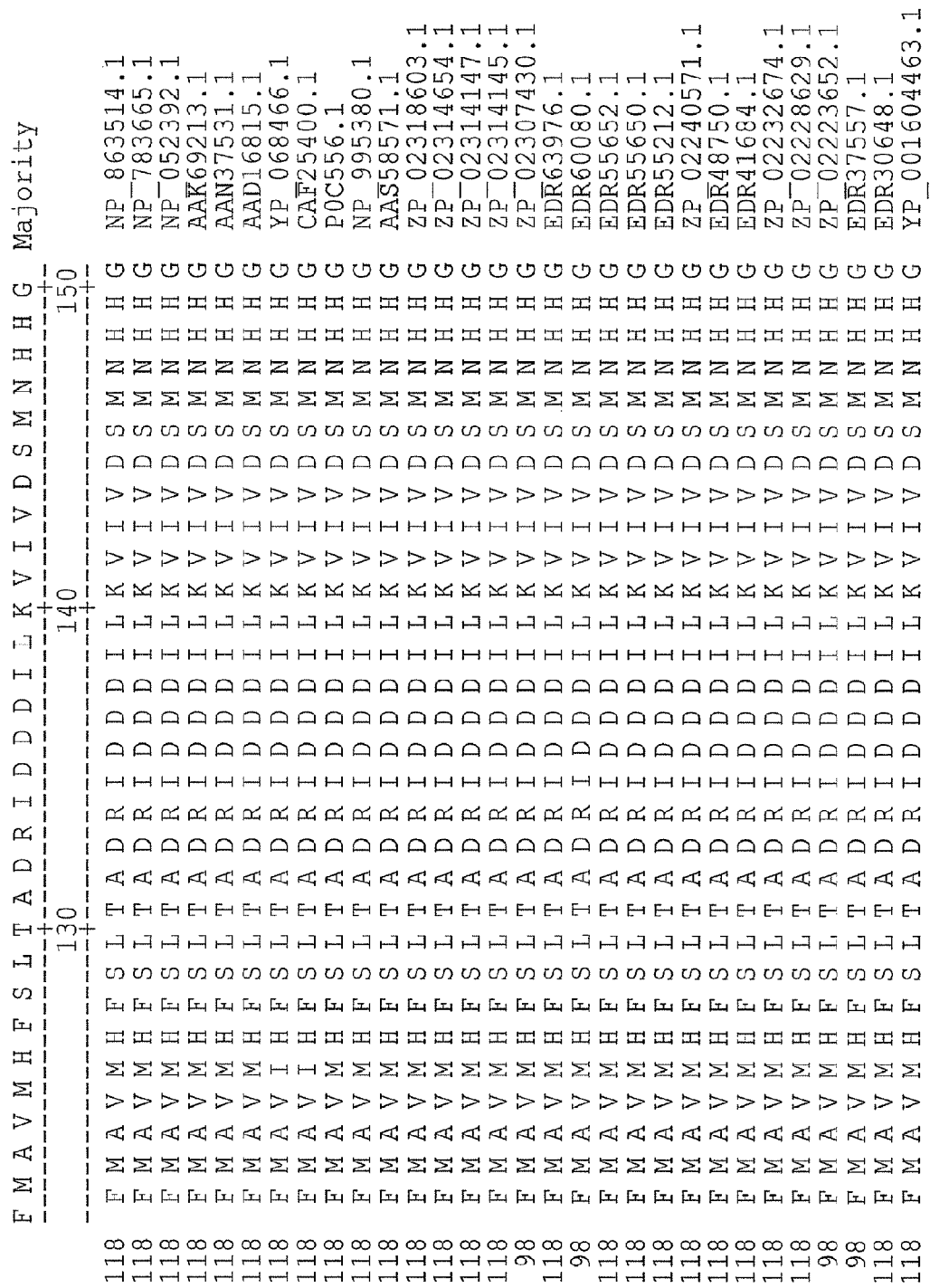
Figure 1K:
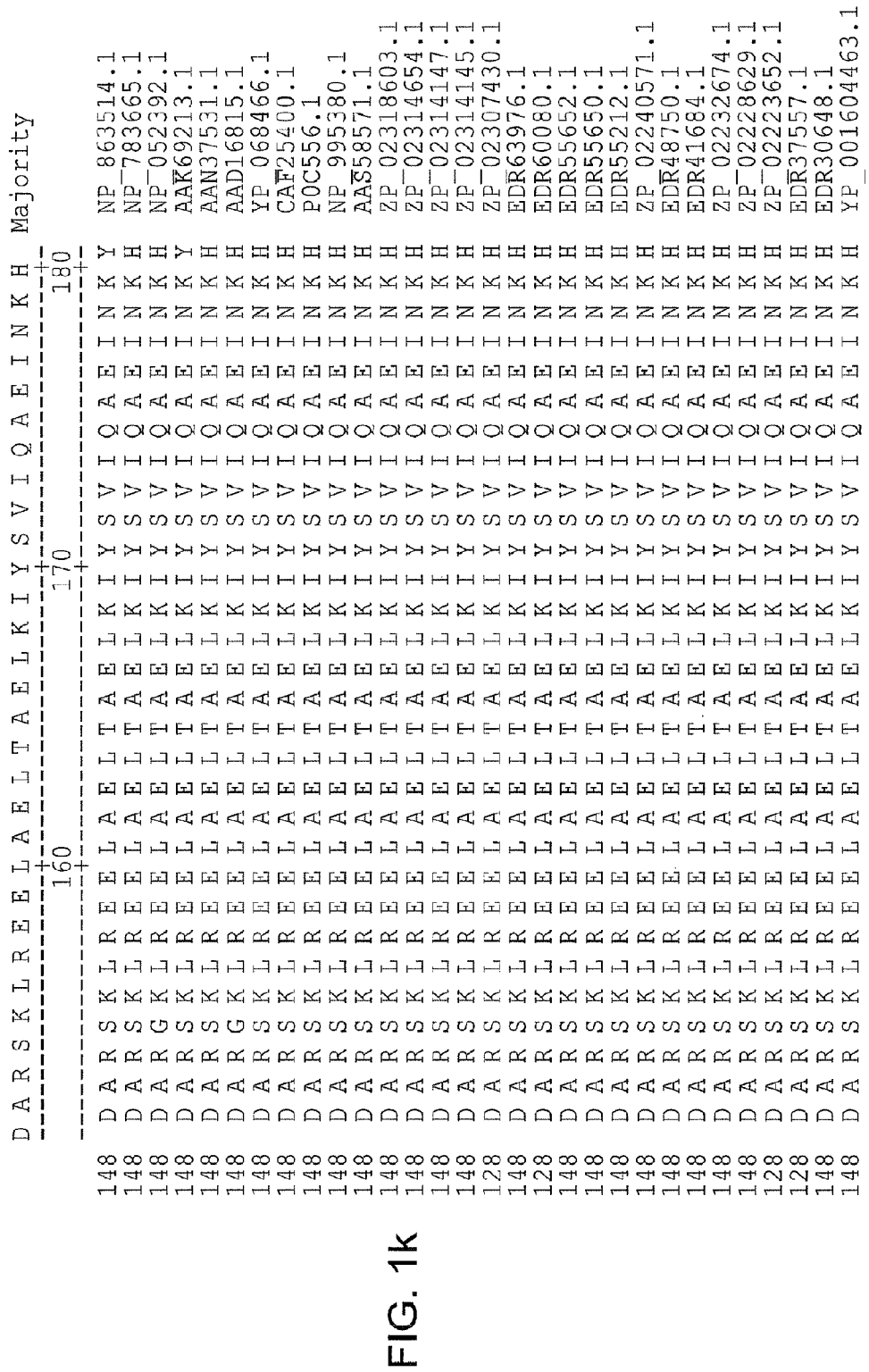

Amino acid: As used herein, term "amino acid," in its broadest sense, refers to any compound and/or substance that can be incorporated into a polypeptide chain. In some embodiments, an amino acid has the general structure H$_2$N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions Amino acids, including carboxy- and/or amino-terminal amino acids in peptides, can be modified by methylation, amidation, acetylation, and/or substitution with other chemical groups that can change the peptide's circulating half-life without adversely affecting their activity Amino acids may participate in a disulfide bond. The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Antibody: As used herein, the term "antibody" refers to any immunoglobulin, whether natural or wholly or partially synthetically produced. All derivatives thereof which maintain specific binding ability are also included in the term. The term also covers any protein having a binding domain which is homologous or largely homologous to an immunoglobulin binding domain. Such proteins may be derived from natural sources, or partly or wholly synthetically produced. An antibody may be monoclonal or polyclonal. An antibody may be a member of any immunoglobulin class, including any of the human classes: IgG, IgM, IgA, IgD, and IgE. As used herein, the terms "antibody fragment" or "characteristic portion of an antibody" are used interchangeably and refer to any derivative of an antibody which is less than full-length. In general, an antibody fragment retains at least a significant portion of the full-length antibody's specific binding ability. Examples of antibody fragments include, but are not limited to, Fab, Fab', F(ab')2, scFv, Fv, dsFv diabody, and Fd fragments. An antibody fragment may be produced by any means. For example, an antibody fragment may be enzymatically or chemically produced by fragmentation of an intact antibody and/or it may be recombinantly produced from a gene encoding the partial antibody sequence. Alternatively or additionally, an antibody fragment may be wholly or partially synthetically produced. An antibody fragment may optionally comprise a single chain antibody fragment. Alternatively or additionally, an antibody fragment may comprise multiple chains which are linked together, for example, by disulfide linkages. An antibody fragment may optionally comprise a multimolecular complex. A functional antibody fragment typically comprises at least about 50 amino acids and more typically comprises at least about 200 amino acids.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, and/or 3' end formation); (3) translation of an RNA into a polypeptide or protein; (4) post-translational modification of a polypeptide or protein.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as tRNAs. For the purpose of clarity we note that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used in this document refers to a protein-coding nucleic acid.

Gene product: As used herein, the term "gene product" or "expression product" generally refers to an RNA transcribed from the gene (pre-and/or post-processing) or a polypeptide (pre- and/or post-modification) encoded by an RNA transcribed from the gene.

Homology: As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least about 25%, about 30%, about 35%, about 40%, about 45%, about 50%, about 55%, about 60%, about 65%, about 70%, about 75%, about 80%, about 85%, about 90%, about 95%, or about 99% identical. In some embodiments, polymeric molecules are considered to be "homologous" to one another if their sequences are at least about 25%, about 30%, about 35%, about 40%, about 45%, about 50%, about 55%, about 60%, about 65%, about 70%, about 75%, about 80%, about 85%, about 90%, about 95%, or about 99% similar.

Identity: As used herein, the term "identity" refers to the overall relatedness between polymeric molecules, e.g. between nucleic acid molecules (e.g. DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least about 30%, at least about 40%, at least about 50%, at least about 60%, at least about 70%, at least about 80%, at least about 90%, at least about 95%, or about 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, at least 4, at least 5, at least 6, at least 7, at least 8, at least 9, at least 10, or more residues. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention may be specifically directed to "unmodified nucleic acids," meaning nucleic acids (e.g. polynucleotides and residues, including nucleotides and/or nucleosides) that have not been chemically modified in order to facilitate or achieve delivery.

Operably linked: As used herein, the term "operably linked" refers to a relationship between two nucleic acid sequences wherein the expression of one of the nucleic acid sequences is controlled by, regulated by, modulated by, etc., the other nucleic acid sequence. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport or localization of a nucleic acid or polypeptide is directed by an operably linked transport or localization sequence; and the post-translational processing of a polypeptide is directed by an operably linked processing sequence. A nucleic acid sequence that is operably linked to a second nucleic acid sequence may be covalently linked, either directly or indirectly, to such a sequence, although any effective three-dimensional association is acceptable.

Portion: As used herein, the phrase a "portion" or "fragment" of a substance, in the broadest sense, is one that shares some degree of sequence and/or structural identity and/or at least one functional characteristic with the relevant intact substance. For example, a "portion" of a protein or polypeptide is one that contains a continuous stretch of amino acids, or a collection of continuous stretches of amino acids, that together are characteristic of a protein or polypeptide. In some embodiments, each such continuous stretch generally will contain at least about 2, about 5, about 10, about 15, about 20 or more amino acids. In general, a portion is one that, in addition to the sequence identity specified above, shares at least one functional characteristic with the relevant intact protein. In some embodiments, the portion may be biologically active.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, etc. In some embodiments, proteins may comprise natural amino acids, non-natural amino acids, synthetic amino acids, and combinations thereof The term "peptide" is generally used to refer to a polypeptide having a length of less than about 100 amino acids.

Similarity: As used herein, the term "similarity" refers to the overall relatedness between polymeric molecules, e.g. between nucleic acid molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Subject: As used herein, the term "subject" or "patient" refers to any organism to which compositions in accordance with the invention may be administered, e.g., for experimental, diagnostic, prophylactic, and/or therapeutic purposes. Typical subjects include animals (e.g., mammals such as mice, rats, rabbits, non-human primates, and humans; insects; worms; etc.).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, and/or condition has been diagnosed with or displays one or more symptoms of the disease, disorder, and/or condition.

Susceptible to: An individual who is "susceptible to" a disease, disorder, and/or condition has not been diagnosed with the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition.

Therapeutic agent: As used herein, the phrase "therapeutic agent" refers to any agent that, when administered to a subject, has a therapeutic effect and/or elicits a desired biological and/or pharmacological effect.

Treatment: As used herein, the term "treatment" (also "treat" or "treating") refers to any administration of a biologically active agent that partially or completely alleviates, ameliorates, relives, inhibits, delays onset of, prevents, reduces severity of and/or reduces incidence of one or more symptoms or features of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Vector: As used herein, "vector" refers to a nucleic acid molecule which can transport another nucleic acid to which it has been linked. In some embodiment, vectors can achieve extra-chromosomal replication and/or expression of nucleic acids to which they are linked in a host cell such as a eukaryotic and/or prokaryotic cell. Vectors capable of directing the expression of operatively linked genes are referred to herein as "expression vectors."

DETAILED DESCRIPTION OF THE INVENTION

The invention relates to *Yersinia pestis* antigens useful in the preparation of vaccines against *Y. pestis* infection, and fusion proteins comprising such *Y. pestis* antigens operably linked a thermostable protein (e.g. lichenase). The invention relates to methods of production of provided antigens, including but not limited to, production in plant systems. Further, the invention relates to vectors, fusion proteins, plant cells, plants and vaccine compositions comprising antigens and fusion proteins in accordance with the invention. Still further provided are methods of inducing immune response against *Y. pestis* infection in a subject comprising administering vaccine compositions in accordance with the invention to a subject.

*Yersinia pestis* Antigens

*Yersinia pestis* (also known as *Pasteurella pestis*) is a Gram-negative rod-shaped bacterium belonging to the family Enterobacteriaceae. It is a facultative anaerobe with bipolar staining (giving it a safety pin appearance). Similar to other *Yersinia* members, it tests negative for urease, lactose fermentation, and indole. *Y. pestis* can infect humans and other animals. Human *Y. pestis* infection takes three main forms: pneumonic, septicemic, and bubonic. All three forms have been responsible for high mortality rates in epidemics throughout human history, including the Black Death (a bubonic plague) that accounted for the death of approximately one-third of the European population in 1347 to 1353. During many of these epidemics, *Y. pestis* was transmitted by fleas infesting rats.

Three biovars of *Y. pestis* are known, each thought to correspond to one of the historical pandemics of bubonic plague. Biovar Antiqua is thought to correspond to the Plague of Justinian; it is not known whether this biovar also corresponds to earlier, smaller epidemics of bubonic plague, or whether these were even truly bubonic plague. Biovar Medievalis is thought to correspond to the Black Death. Biovar Orientalis is thought to correspond to the Third Pandemic and the majority of modern outbreaks of plague.

The complete genomic sequence is available for two of the three sub-species of *Y. pestis*: strain KIM (of biovar Medievalis) (Deng et al., 2002, *J. Bacteria*, 184:4601-11; incorporated herein by reference) and strain CO92 (of biovar Orientalis, obtained from a clinical isolate in the United States) (Parkhill et al., 2001, *Nature*, 413:523-7; incorporated herein by reference). As of 2006, the genomic sequence of a strain of biovar Antiqua has been recently completed (Chain et al., 2006, *J. Bacteriol.*, 188:4453-63; incorporated herein by reference). The chromosome of strain KIM is 4,600,755 base pairs (bp) long; the chromosome of strain CO92 is 4,653,728 bp long.

Like its cousins *Y. pseudotuberculosis* and *Y. enterocolitica*, *Y. pestis* is host to the plasmid pCD1. In addition, it also hosts two other plasmids, pPCP1 and pMT1, which are not carried by the other *Yersinia* species. Together, these plasmids, and a pathogenicity island called HPI, encode several proteins which are thought to cause pathogenesis. Among other things, these virulence factors are involved in bacterial adhesion and injection of proteins into the host cell, invasion of bacteria into the host cell, and acquisition and binding of iron harvested from red blood cells.

*Y. pestis* is thought to be descendant from *Y. pseudotuberculosis*, differing only in the presence of specific virulence plasmids. For example, *Y. pestis* LcrV sequences are typically between about 90%—about 100% identical (e.g., about 90%, about 91%, about 92%, about 93%, about 94%, about 95%, about 96%, about 97%, about 98%, about 99%, or about 100% identical) to LcrV sequences from *Y. pseudotuberculosis*. *Y. pestis* LcrV sequences are typically between about 90%—about 100% identical (e.g., about 90%, about 91%, about 92%, about 93%, about 94%, about 95%, about 96%, about 97%, about 98%, about 99%, or about 100% identical) to LcrV sequences from *Y. enterocolitica*. Thus, the present invention encompasses the recognition that *Y. pestis* antigens may be useful for conferring protectivity and/or mounting an immune response against multiple *Yersinia* species, including *Y. pestis*, *Y. pseudotuberculosis*, and/or *Y. enterocolitica*.

The traditional first line treatment for *Y. pestis* has been streptomycin, chloramphenicol, tetracycline, and fluoroquinolones. In some cases, doxycycline or gentamicin might be useful to treat *Y. pestis* infection. Antibiotic treatment alone is insufficient for some patients, who may also require circulatory, ventilator, or renal support. Prior to the present invention, no plant-produced *Y. pestis* vaccine has been shown to be safe and effective in humans or non-human primates (Alvarez et al., 2006, *Vaccine*, 24:2477-90; and Santi et al., 2006, *Proc. Natl. Acad. Sci., USA*, 103:861-6; Williamson et al., *Infect. Immun.*, 2005, 73:3598-608; Anderson et al., 1996, *Infect. Immun.*, 64:4580-5; Andrews et al., 1996, *Infect. Immun.*, 64:2180-7; Williamson et al., 2000, *Vaccine*, 19:566-71; Williamson et al., 1995, *FEMS Immunol. Med. Microbiol.*, 12:223-30; and Heath et al., 1998, *Vaccine*, 16:1131-7; all of which are incorporated herein by reference).

*Y. pestis* antigen proteins in accordance with the invention include any immunogenic protein or peptide capable of eliciting an immune response against *Y. pestis*. Generally, immunogenic proteins of interest include *Y. pestis* antigens (e.g., *Y. pestis* proteins, fusion proteins, etc.), immunogenic portions thereof, or immunogenic variants thereof and combinations of any of the foregoing.

Any *Y. pestis* protein can be produced and utilized as an antigen in accordance with the present invention. Typically, *Y. pestis* proteins (i.e. full-length proteins, portions, fragments, and/or domains thereof, peptides, etc.) that are useful as antigens are not substantially identical and/or homologous to proteins which are expressed by the animal being vaccinated. In some embodiments, *Y. pestis* proteins are less than 90%, less than 80%, less than 70%, less than 60%, less than 50%, less than 40%, less than 30%, less than 20%, or less than 10% identical and/or homologous to proteins which are expressed by the animal being vaccinated. In some embodiments, a particular *Y. pestis* protein may have portions and/or domains that are substantially identical and/or homologous to proteins which are expressed by the animal being vaccinated as well as portions and/or domains that are not substantially identical and/or homologous to proteins which are expressed by the animal being vaccinated. In some embodiments, proteins and/or peptides to be used in accordance with the present invention are protein portions and/or domains that are not substantially identical and/or homologous to proteins which are expressed by the animal being vaccinated that have been separated and/or isolated from protein portions and/or domains that are substantially identical and/or homologous to proteins which are expressed by the animal being vaccinated.

*Y. pestis* antigens for use in accordance with the present invention may include full-length *Y. pestis* proteins or portions (i.e. fragments, domains, etc.) of *Y. pestis* proteins, and/or fusion proteins comprising full-length *Y. pestis* proteins or portions of *Y. pestis* proteins. Where portions of *Y. pestis* proteins are utilized, whether alone or in fusion proteins, such portions retain immunological activity (e.g., cross-reactivity with anti-*Y. pestis* antibodies). The present invention relates to two *Y. pestis* antigens that are of interest for developing a vaccine against *Y. pestis*: the anti-phagocytic capsular envelope glycoprotein (F1) and the low calcium-response V (LcrV) protein. Additional antigens (e.g., proteins, lipoproteins, glycoproteins, proteoglycans, and/or peptidoglycans associated with cell membranes and/or cell surfaces; surface antigens; periplasmic proteins; etc.) may be useful in production of vaccines (e.g., combination vaccines) in order to improve efficacy of immunoprotection.

Thus, the invention provides plant cells and/or plants expressing a heterologous protein, such as a *Y. pestis* antigen (e.g., *Y. pestis* protein or a fragment thereof, a fusion protein comprising a *Y. pestis* protein or portion thereof). A heterologous protein in accordance with the invention can comprise any *Y. pestis* antigen of interest, including, but not limited to F1, LcrV, or fusion proteins, portions, or combinations of F1, LcrV, a portion of F1, and/or a portion of LcrV. In some embodiments, the invention provides plant cells and/or plants expressing a full-length heterologous protein. In some embodiments, the invention provides plant cells and/or plants expressing a portion of a heterologous protein. In some embodiments, the invention provides plant cells and/or plants expressing multiple portions of a heterologous protein. In some embodiments, such multiple portions are each produced from an individual vector. In some embodiments, such multiple protein portions are tandemly expressed from the same vector (i.e. a "polytope"). In some embodiments, all of the multiple protein portions of a polytope are identical to one another. In some embodiments, not all of the multiple protein portions are identical to one another.

Amino acid sequences of a variety of different *Y. pestis* proteins (e.g., F1 and/or LcrV) are known in the art and are available in public databases such as GenBank. In some embodiments, *Y. pestis* antigens comprise F1 protein and/or a characteristic portion thereof In some embodiments, F1 protein is variable at amino acid position 48. In some embodiments, the amino acid at position 48 is alanine. In some embodiments, the amino acid at position 48 is serine. In some embodiments, multiple F1 protein variants differ only at position 48.

Exemplary full-length amino acid sequences for F1 protein which comprise an alanine at residue 48 include, but are not limited to, amino acid sequences as set forth in GenBank accession numbers NP_395430; AAM94402.1; AAM94401.1; AAM94400.1; AAM94399.1; AAM94398.1; AAM94397.1; AAM94396.1; AAM94395.1; NP_995523.1; AAS58714.1; CAA43966.1; NP_857881.1; AAC82758.1; YP_636639.1; and YP_636755.1. In some embodiments, an F1 protein comprising an alanine at residue 48 may be obtained, isolated, purified, and/or derived from *Y. pestis* strains CO92, Antigua, Microtus, Str.91001, KIM, Nepal 516, and/or FV 1.

One exemplary full length protein sequence for F1 protein comprising an alanine at position 48 is:

(SEQ ID NO: 1)
5'MKKISSVIAIALFGTIATANAADLTASTTATATLVEPARITLTYKEGAPITIMDNGNIDTELLVGTLTLGGYKTGTTSTSVNFTDAAGDPMYLTFTSQDGNNHQFTTKVIGKDSRDFDISPKVNGENLVGDDVVLATGSQDFFVRSIGSKGGKLAAGKYTDAVTVTVSNQ 3'.

The bold, underlined sequence above (i.e., MKK...ANA) corresponds to a signal sequence. The bold, underlined alanine residue at position 48 corresponds to a site of variability in the F1 protein.

In some embodiments, a *Y. pestis* antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to SEQ ID NO: 1.

In some embodiments, a *Y. pestis* antigen comprises an amino acid sequence which comprises about 100 contiguous amino acids of SEQ ID NO: 1. In some embodiments, a *Y. pestis* antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 100 amino acids of SEQ ID NO: 1.

One exemplary full-length nucleotide sequence encoding F1 protein comprising an alanine at position 48 corresponds to GenBank accession number NC_003134 (83368 . . . 85869):

(SEQ ID NO: 2)
5'ATGAAAAAAATCAGTTCCGTTATCGCCATTGCATTATTTGGAACTATTGCAACTGCTAATGCGGCAGATTTAACTGCAAGCACCACTGCAACGGCAACTCTTGTTGAACCAGCCCGCATCACTCTTACATATAAGGAAGGCGCTCCAATTACAATTATGGACAATGGAAACATCGATACAGAATTACTTGTTGGTACGCTTACTCTTGGCGGCTATAAAACAGGAACCACTAGCACATCTGTTAACTTTACAGATGCCGCGGGTGATCCCATGTACTTAACATTTACTTCTCAGGATGGAAATAACCACCAATTCACTACAAAAGTGATTGGCAAGGATTCTAGAGATTTTGATATCTCTCCTAAGGTAAACGGTGAGAACCTTGTGGGGGATGACGTCGTCTTGGCTACGGGCAGCCAGGATTTCTTTGTTCGCTCAATTGGTTCCAAAGGCGGTAAACTTGCAGCAGGTAAATACACTGATGCTGTAACCGTAACCGTATCTAACCAATAA 3'.

The bold, underlined sequence above (i.e., ATG...GCG) corresponds to the nucleotide sequence encoding a signal sequence of F1 protein. The bold, underlined codon (i.e., GCT) corresponds to the nucleotide sequence encoding the alanine residue at position 48.

In some embodiments, full length F1 protein does not comprise the signal sequence. One exemplary full length protein sequence for F1 protein comprising an alanine at position 48 but not comprising a signal sequence is:

(SEQ ID NO: 3)
5'ADLTASTTATATLVEPARITLTYKEGAPITIMDNGNIDTELLVGTLTLGGYKTGTTSTSVNFTDAAGDPMYLTFTSQDGNNHQFTTKVIGKDSRDFDISPKVNGENLVGDDVVLATGSQDFFVRSIGSKGGKLAAGKYTDAVTVTVSNQ 3'.

The bold, underlined alanine residue at position 48 corresponds to a site of variability in the F1 protein.

In some embodiments, a *Y. pestis* antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to SEQ ID NO: 3.

In some embodiments, a *Y. pestis* antigen comprises an amino acid sequence which comprises about 100 contiguous amino acids of SEQ ID NO: 3. In some embodiments, a *Y. pestis* antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 100 amino acids of SEQ ID NO: 3.

One exemplary full-length nucleotide sequence encoding F1 protein comprising an alanine at position 48 but not comprising a signal sequence is:

(SEQ ID NO: 4)
5'GCAGATTTAACTGCAAGCACCACTGCAACGGCAACTCTTGTTGAACCAGCCCGCATCACTCTTACATATAAGGAAGGCGCTCCAATTACAATTATGGACAATGGAAACATCGATACAGAATTACTTGTTGGTACGCTTACTCTTGGCGGCTATAAAACAGGAACCACTAGCACATCTGTTAACTTTACAGATGCCGCGGGTGATCCCATGTACTTAACATTTACTTCTCAGGATGGAATAACCACCAATTCACTACAAAAGTGATTGGCAAGGATTCTAGAGATTTTGATATCTCTCCTAAGGTAAACGGTGAGAACCTTGTGGGGGATGACGTCGTCTTGGCTACGGGCAGCCAGGATTTCTTTGTTCGCTCAATTGGTTCCAAAGGCGGTAAACTTGCAGCAGGTAAATACACTGATGCTGTAACCGTATCTAACCAATAA 3'.

The bold, underlined codon (i.e., GCT) corresponds to the nucleotide sequence encoding the alanine residue at position 48.

Exemplary full-length amino acid sequences for F1 protein which comprise a serine at residue 48 include, but are not limited to, amino acid sequences as set forth in GenBank accession numbers YP_093952, YP_001154728.1, CAG27478.1, and/or ABP42491.1. In some embodiments, an F1 protein comprising a serine at residue 48 may be obtained, isolated, purified, and/or derived from *Y. pestis* strains Pestoides, CA 88-4125, and/or EV.

One exemplary full length protein sequence for F1 protein comprising a serine at position 48 is:

(SEQ ID NO: 5)
5'MKKISSVIAIALFGTIATANAADLTASTTATATLVEPARITLTYK
EGSPITIMDNGNIDTELLVGTLTLGGYKTGTTSTSVNFTDAAGDPMY
LTFTSQDGNNHQFTTKVIGKDSRDFDISPKVNGENLVGDDVVLATGS
QDFFVRSIGSKGGKLAAGKYTDAVTVTVSNQ 3'.

The bold, underlined sequence above (i.e., MKK...ANA) corresponds to a signal sequence. The bold, underlined serine residue at position 48 corresponds to a site of variability in the F1 protein.

In some embodiments, a *Y. pestis* antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to SEQ ID NO: 5.

In some embodiments, a *Y. pestis* antigen comprises an amino acid sequence which comprises about 100 contiguous amino acids of SEQ ID NO: 5. In some embodiments, a *Y. pestis* antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 100 amino acids of SEQ ID NO: 5.

One exemplary full-length nucleotide sequence encoding F1 protein comprising an serine at position 48 corresponds to GenBank accession number NC_006323.1:

(SEQ ID NO: 6)
5'ATGAAAAAAATCAGTTCCGTTATCGCCATTGCATTATTTGGAACT
ATTGCAACTGCTAATGCGGCAGATTTAACTGCAAGCACCACTGCAAC
GGCAACTCTTGTTGAACCAGCCCGCATCACTCTTACATATAAGGAAG
GCTCTCCAATTACAATTATGGACAATGGAAACATCGATACAGAATTA
CTTGTTGGTACGCTTACTCTTGGCGGCTATAAAACAGGAACCACTAG
CACATCTGTTAACTTTACAGATGCCGCGGGTGATCCCATGTACTTAA
CATTTACTTCTCAGGATGGAAATAACCACCAATTCACTACAAAAGTG
ATTGGCAAGGATTCTAGAGATTTTGATATCTCTCCTAAGGTAAACGG
TGAGAACCTTGTGGGGATGACGTCGTCTTGGCTACGGGCAGCCAGG
ATTTCTTTGTTCGCTCAATTGGTTCCAAAGGCGGTAAACTTGCAGCA
GGTAAATACACTGATGCTGTAACCGTAACCGTATCTAACCAATA
A 3'.

The bold, underlined sequence above (i.e., ATG...GCG) corresponds to the nucleotide sequence encoding a signal sequence of F1 protein. The bold, underlined codon (i.e., TCT) corresponds to the nucleotide sequence encoding the serine residue at position 48.

In some embodiments, full length F1 protein does not comprise the signal sequence. One exemplary full length protein sequence for F1 protein comprising an alanine at position 48 but not comprising a signal sequence is:

(SEQ ID NO: 7)
5'ADLTASTTATATLVEPARITLTYKEGSPITIMDNGNIDTELLVGT
LTLGGYKTGTTSTSVNFTDAAGDPMYLTFTSQDGNNHQFTTKVIGKD
SRDFDISPKVNGENLVGDDVVLATGSQDFFVRSIGSKGGKLAAGKYT
DAVTVTVSNQ 3'.

The bold, underlined serine residue at position 48 corresponds to a site of variability in the F1 protein.

In some embodiments, a *Y. pestis* antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to SEQ ID NO: 7.

In some embodiments, a *Y. pestis* antigen comprises an amino acid sequence which comprises about 100 contiguous amino acids of SEQ ID NO: 7. In some embodiments, a *Y. pestis* antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 100 amino acids of SEQ ID NO: 7.

One exemplary full-length nucleotide sequence encoding F1 protein comprising an serine at position 48 but not comprising a signal sequence is:

(SEQ ID NO: 8)
5'CAGATTTAACTGCAAGCACCACTGCAACGGCAACTCTTGTTGAAC
CAGCCCGCATCACTCTTACATATAAGGAAGGCTCTCCAATTACAATT
ATGGACAATGGAAACATCGATACAGAATTACTTGTTGGTACGCTTAC
TCTTGGCGGCTATAAAACAGGAACCACTAGCACATCTGTTAACTTTA
CAGATGCCGCGGGTGATCCCATGTACTTAACATTTACTTCTCAGGAT
GGAAATAACCACCAATTCACTACAAAAGTGATTGGCAAGGATTCTAG
AGATTTTGATATCTCTCCTAAGGTAAACGGTGAGAACCTTGTGGGGG
ATGACGTCGTCTTGGCTACGGGCAGCCAGGATTTCTTTGTTCGCTCA
ATTGGTTCCAAAGGCGGTAAACTTGCAGCAGGTAAATACACTGATGC
TGTAACCGTAACCGTATCTAACCAATAA 3'.

The bold, underlined codon (i.e., TCT) corresponds to the nucleotide sequence encoding the serine residue at position 48.

In certain embodiments, full length F1 protein is utilized in vaccine compositions in accordance with the invention. In some embodiments, one or more portions and/or domains of F1 protein is used. In certain embodiments, two or three or more portions and/or domains are utilized, as one or more separate polypeptides or linked together in one or more fusion polypeptides.

In some embodiments, *Y. pestis* antigens comprise LcrV protein and/or a characteristic portion thereof Exemplary full-length amino acid sequences for LcrV protein include, but are not limited to, amino acid sequences as set forth in GenBank accession numbers NP_863514.1; NP_783665.1; NP_052392.1; AAK69213.1; AAN37531.1; AAD16815.1;

YP_068466.1; CAF25400.1; P00556.1; NP_995380.1;
AAS58571.1; ZP_02318603.1; ZP_02314654.1;
ZP_02314147.1; ZP_02314145.1; ZP_02307430.1;
EDR63976.1; EDR60080.1; EDR55652.1; EDR55650.1;
EDR55212.1; ZP_02240571.1; EDR48750.1;
EDR41684.1; ZP_02232674.1; ZP_02228629.1;
ZP_02223652.1; EDR37557.1; EDR30648.1;
YP_001604463.1; ABX88711.1; CAB54908.1;
ABF48194.1; ABF48193.1; ABF48192.1; ABF48191.1;
ABF48190.1; ABF48189.1; NP_395165.1;
YP_001293940.1; NP_857946.1; NP_857751.1;
ABR68791.1; ABR68790.1; ABR68789.1; ABR68788.1;
ABR14856.1; AAC69799.1; AAC62574.1; AAF64077.1;
A4TSQ1.1; YP_001004069.1; CAL10039.1; P23994.1;
AAA27645.1; AAF64076.1; YP_636823.1; ABG16274.1;
ABP42325.1; YP_001154615.1; ABB16313.1;
YP_001874676.1; ACC91219.1; and/or ABI97154.1 (SEQ ID NOs: 38-102, respectively; see FIG. 1). In some embodiments, an LcrV protein may be obtained, isolated, purified, and/or derived from *Y. pestis* strains, for example, from Antigua strain E1979001, Antigua strain B42003004, Ulegeica, CA88-4125, KIM, Orientalis strain MG05-1020, and/or Mediaevalis strain K1973002. FIG. 1 presents multiple LcrV protein variants from different *Y. pestis* strains aligned with the sequence of LcrV that was used in the production of antigen constructs in the Exemplification ("LcrV.pro," SEQ ID NO: 103).

One exemplary full length protein sequence for LcrV protein is:

(SEQ ID NO: 9)
5'MIRAYEQNPQHFIEDLEKVRVEQLTGHGSSVLEELVQLVKDKNID

ISIKYDPRKDSEVFANRVITDDIELLKKILAYFLPEDAILKGGHYDN

QLQNGIKRVKEFLESSPNTQWELRAFMAVMHFSLTADRIDDDILKVI

VDSMNHHGDARSKLREELAELTAELKIYSVIQAEINKHLSSSGTINI

HDKSINLMDKNLYGYTDEEIFKASAEYKILEKMPQTTIQVDGSEKKI

VSIKDFLGSENKRTGALGNLKNSYSYNKDNNELSHFATTCSDKSRPL

NDLVSQKTTQLSDITSRFNSAIEALNRFIQKYDSVMQRLLDDTSG

K 3'.

In some embodiments, a *Y. pestis* antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to SEQ ID NO: 9.

In some embodiments, a *Y. pestis* antigen comprises an amino acid sequence which comprises about 100 contiguous amino acids of SEQ ID NO: 9. In some embodiments, a *Y. pestis* antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 100 amino acids of SEQ ID NO: 9.

One exemplary full-length nucleotide sequence encoding LcrV protein is:

(SEQ ID NO: 10)
5'ATGATAAGGGCTTATGAACAAAATCCACAGCATTTTATTGAAGA

CCTAGAGAAAGTGCGAGTCGAACAGCTGACCGGCCATGGGTCGTCC

GTTCTCGAAGAATTGGTGCAATTAGTTAAAGATAAAAACATCGATA

TTTCTATTAAGTACGACCCTAGGAAGGATTCTGAGGTATTTGCTAA

TAGAGTGATTACAGATGATATTGAATTACTAAAAAAGATATTGGCA

TACTTCCTTCCTGAGGATGCTATTCTTAAGGGTGGACACTATGACA

ATCAACTTCAAAACGGCATTAAGAGGGTTAAGGAGTTCCTCGAAAG

CTCTCCAAATACTCAATGGGAGTTACGTGCTTTTATGGCTGTTATG

CATTTTAGTCTGACAGCTGATCGAATTGATGATGATATTCTAAAGG

TAATTGTAGATTCCATGAATCATCACGGTGACGCCAGGTCTAAGTT

GCGTGAAGAGCTTGCTGAGTTGACTGCTGAACTGAAGATATATTCC

GTGATACAGGCAGAAATTAACAAGCACTTATCATCTTCAGGAACTA

TTAATATTCACGATAAGTCTATTAATCTTATGGATAAAAACCTATA

CGGTTATACTGATGAGGAGATTTTCAAAGCTAGTGCGGAGTACAAA

ATATTAGAAAAGATGCCCCAAACTACTATACAGGTGGATGGGTCTG

AAAAGAAGATTGTTTCTATCAAAGATTTCCTGGGTAGCGAAAACAA

AAGAACGGGAGCACTTGGGAATCTCAAGAATTCTTATTCATATAAC

AAAGATAACAACGAGCTTTCACATTTCGCAACTACTTGTAGTGATA

AGTCCAGACCACTCAACGATCTTGTATCACAAAAGACAACTCAATT

GTCTGACATTACTTCTCGTTTCAACAGCGCTATTGAAGCACTTAAT

AGGTTCATTCAGAAGTACGATTCTGTGATGCAAAGATTGCTTGATG

ATACATCTGGAAAG 3'.

In certain embodiments, full length LcrV protein is utilized in vaccine compositions in accordance with the invention. In some embodiments one or more portions and/or domains of LcrV protein is used. In certain embodiments, two or three or more portions and/or domains are utilized, as one or more separate polypeptides or linked together in one or more fusion polypeptides.

In some embodiments, a *Y. pestis* antigen composition comprises a fusion protein. In some embodiments, the fusion protein may contain two or more identical antigen proteins. In some embodiments, the fusion protein may contain two or more distinct antigen proteins. In some embodiments, a *Y. pestis* antigen composition comprises a fusion of F1 and LcrV proteins.

In some embodiments, a fusion of F1 and LcrV proteins has an amino acid sequence that is identical to that set forth in SEQ ID NO: 27. In some embodiments, a *Y. pestis* antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to SEQ ID NO: 27.

In some embodiments, a *Y. pestis* antigen comprises an amino acid sequence which comprises about 100 contiguous amino acids of SEQ ID NO: 27. In some embodiments, a *Y. pestis* antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 100 amino acids of SEQ ID NO: 27.

In some embodiments, a fusion of F1 and LcrV proteins comprises an amino acid sequence that is identical to that set forth in SEQ ID NO: 33. In some embodiments, a Y. pestis antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to SEQ ID NO: 33.

In some embodiments, a Y. pestis antigen comprises an amino acid sequence which comprises about 100 contiguous amino acids of SEQ ID NO: 33. In some embodiments, a Y. pestis antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 100 amino acids of SEQ ID NO: 33.

In some embodiments, a fusion of F1 and LcrV proteins comprises an amino acid sequence that is identical to that set forth in SEQ ID NO: 34. In some embodiments, a Y. pestis antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to SEQ ID NO: 34.

In some embodiments, a Y. pestis antigen comprises an amino acid sequence which comprises about 100 contiguous amino acids of SEQ ID NO: 34. In some embodiments, a Y. pestis antigen comprises an amino acid sequence which is about 60% identical, about 7% identical, about 80% identical, about 85% identical, about 90% identical, about 91% identical, about 92% identical, about 93% identical, about 94% identical, about 95% identical, about 96% identical, about 97% identical, about 98% identical, about 99% identical, or 100% identical to a contiguous stretch of about 100 amino acids of SEQ ID NO: 34.

In some embodiments, a fusion of F1 and LcrV proteins comprises amino acid sequences that are identical to those set forth in SEQ ID NOs: 33 and 34.

In some embodiments, a Y. pestis antigen comprises amino acid sequences which are greater than 60% identical, greater than 7% identical, greater than 80% identical, greater than 85% identical, greater than 90% identical, greater than 91% identical, greater than 92% identical, greater than 93% identical, greater than 94% identical, greater than 95% identical, greater than 96% identical, greater than 97% identical, greater than 98% identical, greater than 99% identical, or 100% identical to SEQ ID NOs: 33 and 34.

In some embodiments, a Y. pestis antigen comprises amino acid sequences which comprise about 100 contiguous amino acids of each of SEQ ID NOs: 33 and 34. In some embodiments, a Y. pestis antigen comprises amino acid sequences which are greater than 60% identical, greater than 7% identical, greater than 80% identical, greater than 85% identical, greater than 90% identical, greater than 91% identical, greater than 92% identical, greater than 93% identical, greater than 94% identical, greater than 95% identical, greater than 96% identical, greater than 97% identical, greater than 98% identical, greater than 99% identical, or 100% identical to contiguous stretches of about 100 amino acids of each of SEQ ID NOs: 33 and 34.

As exemplary antigens, we have utilized sequences from Y. pestis F1 and LcrV as described in detail herein. However, it will be understood by one skilled in the art that the methods and compositions provided herein may be adapted to utilize any Y. pestis sequences. It will also be understood by one skilled in the art that the methods and compositions provided herein may be adapted to utilize sequences of any Y. pestis species and/or subtype. Such variation is contemplated and encompassed within the methods and compositions provided herein.

Production of Yersinia pestis Antigens

In accordance with the present invention, Y. pestis antigens (including Y. pestis protein(s), portions, fragments, domains, variants, and/or fusions thereof) may be produced in any desirable system; production is not limited to plant systems. Vector constructs and expression systems are well known in the art and may be adapted to incorporate use of Y. pestis antigens provided herein. For example, Y. pestis antigens (including Y. pestis protein(s), portions, fragments, domains, variants, and/or fusions thereof) can be produced in known expression systems, including mammalian cell systems, transgenic animals, microbial expression systems, insect cell systems, and plant systems, including transgenic and transient plant systems. Particularly where Y. pestis antigens are produced as fusion proteins, it may be desirable to produce such fusion proteins in non-plant systems.

In some embodiments, Y. pestis antigens are desirably produced in plant systems. Plants are relatively easy to manipulate genetically, and have several advantages over alternative sources such as human fluids, animal cell lines, recombinant microorganisms and transgenic animals. Plants have sophisticated post-translational modification machinery for proteins that is similar to that of mammals (although it should be noted that there are some differences in glycosylation patterns between plants and mammals). This enables production of bioactive reagents in plant tissues. Also, plants can economically produce very large amounts of biomass without requiring sophisticated facilities. Thus, protein production in plants typically requires a much lower capital investment and cost-of-goods than does protein production using other systems. Moreover, plants are not subject to contamination with animal pathogens. Like liposomes and microcapsules, plant cells are expected to provide protection for passage of antigen to the gastrointestinal tract. In many instances, production of proteins in plants leads to improved consumer safety.

Plants may be utilized for production of heterologous proteins via use of various production systems. One such system includes use of transgenic/genetically-modified plants where a gene encoding target product is permanently incorporated into the genome of the plant. Transgenic systems may generate crop production systems. A variety of foreign proteins, including many of mammalian origin and many vaccine candidate antigens, have been expressed in transgenic plants and shown to have functional activity (Tacket et al., 2000, J. Infect. Dis., 182:302; and Thanavala et al., 2005, Proc. Natl. Acad. Sci., USA, 102:3378; both of which are incorporated herein by reference). Additionally, administration of unprocessed transgenic plants expressing hepatitis B major surface antigen to non-immunized human volunteers resulted in production of immune response (Kapusta et al., 1999, FASEB J., 13:1796; incorporated herein by reference).

One system for expressing polypeptides in plants utilizes plant viral vectors engineered to express foreign sequences (e.g., transient expression). This approach allows for use of healthy non-transgenic plants as rapid production systems. Thus, genetically engineered plants and plants infected with recombinant plant viruses can serve as "green factories" to rapidly generate and produce specific proteins of interest. Plant viruses have certain advantages that make them attractive as expression vectors for foreign protein production. Several members of plant RNA viruses have been well characterized, and infectious cDNA clones are available to facilitate genetic manipulation. Once infectious viral genetic material enters a susceptible host cell, it replicates to high levels and spreads rapidly throughout the entire plant. There are several approaches to producing target polypeptides using plant viral expression vectors, including incorporation of target polypeptides into viral genomes. One approach involves engineering coat proteins of viruses that infect bacteria, animals or plants to function as carrier molecules for antigenic peptides. Such carrier proteins have the potential to assemble and form recombinant virus-like particles displaying desired antigenic epitopes on their surface. This approach allows for time-efficient production of vaccine candidates, since the particulate nature of a vaccine candidate facilitates easy and cost-effective recovery from plant tissue. Additional advantages include enhanced target-specific immunogenicity, the potential to incorporate multiple vaccine determinants, and ease of formulation into vaccines that can be delivered nasally, orally or parenterally. As an example, spinach leaves containing recombinant plant viral particles carrying epitopes of virus fused to coat protein have generated immune response upon administration (Modelska et al., 1998, *Proc. Natl. Acad. Sci., USA,* 95:2481; and Yusibov et al., 2002, *Vaccine,* 19/20:3155; both of which are incorporated herein by reference).

Plant Expression Systems

Any plant susceptible to incorporation and/or maintenance of heterologous nucleic acid and capable of producing heterologous protein may be utilized in accordance with the present invention. In general, it will often be desirable to utilize plants that are amenable to growth under defined conditions, for example in a greenhouse and/or in aqueous systems. It may be desirable to select plants that are not typically consumed by human beings or domesticated animals and/or are not typically part of the human food chain, so that they may be grown outside without concern that expressed polynucleotide may be undesirably ingested. In some embodiments, however, it will be desirable to employ edible plants. In particular embodiments, it will be desirable to utilize plants that accumulate expressed polypeptides in edible portions of a plant.

Often, certain desirable plant characteristics will be determined by the particular polynucleotide to be expressed. To give but a few examples, when a polynucleotide encodes a protein to be produced in high yield (as will often be the case, for example, when antigen proteins are to be expressed), it will often be desirable to select plants with relatively high biomass (e.g., tobacco, which has additional advantages that it is highly susceptible to viral infection, has a short growth period, and is not in the human food chain). Where a polynucleotide encodes antigen protein whose full activity requires (or is inhibited by) a particular post-translational modification, the ability (or inability) of certain plant species to accomplish relevant modification (e.g., a particular glycosylation) may direct selection. For example, plants are capable of accomplishing certain post-translational modifications (e.g., glycosylation), however, plants will not generate siaylation sialyation patterns which are found in mammalian post-translational modification. Thus, plant production of antigen may result in production of a different entity than the identical protein sequence produced in alternative systems.

In certain embodiments, crop plants, or crop-related plants are utilized. In certain specific embodiments, edible plants are utilized.

Plants for use in accordance with the present invention include Angiosperms, Bryophytes (e.g., Hepaticae, Musci, etc.), Pteridophytes (e.g., ferns, horsetails, lycopods), Gymnosperms (e.g., conifers, cycase, Ginko, Gnetales), and Algae (e.g., Chlorophyceae, Phaeophyceae, Rhodophyceae, Myxophyceae, Xanthophyceae, and Euglenophyceae). Exemplary plants are members of the family Leguminosae (Fabaceae; e.g., pea, alfalfa, soybean); Gramineae (Poaceae; e.g., corn, wheat, rice); Solanaceae, particularly of the genus *Lycopersicon* (e.g., tomato), *Solanum* (e.g., potato, eggplant), *Capsium* (e.g., pepper), or *Nicotiana* (e.g., tobacco); Umbelliferae, particularly of the genus *Daucus* (e.g., carrot), *Apium* (e.g., celery), or *Rutaceae* (e.g., oranges); Compositae, particularly of the genus *Lactuca* (e.g., lettuce); Brassicaceae (Cruciferae), particularly of the genus *Brassica* or *Sinapis*. In certain aspects, plants in accordance with the invention may be plants of the *Brassica* or *Arabidopsis* genus. Some exemplary Brassicaceae family members include *Brassica campestris, B. carinata, B. juncea, B. napus, B. nigra, B. oleraceae, B. tournifortii, Sinapis alba*, and *Raphanus sativus*. Some suitable plants that are amendable to transformation and are edible as sprouted seedlings include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as sunflower, peas, etc.

Introducing Vectors into Plants

In general, vectors may be delivered to plants according to known techniques. For example, vectors themselves may be directly applied to plants (e.g., via abrasive inoculations, mechanized spray inoculations, vacuum infiltration, particle bombardment, or electroporation). Alternatively or additionally, virions may be prepared (e.g., from already infected plants), and may be applied to other plants according to known techniques.

A wide variety of viruses are known that infect various plant species, and can be employed for polynucleotide expression according to the present invention (see, for example, in *The Classification and Nomenclature of Viruses*, "Sixth Report of the International Committee on Taxonomy of Viruses" (Ed. Murphy et al.), Springer Verlag: New York, 1995, the entire contents of which are incorporated herein by reference; Grierson et al., *Plant Molecular Biology*, Blackie, London, pp. 126-146, 1984; Gluzman et al., *Communications in Molecular Biology: Viral Vectors*, Cold Spring Harbor Laboratory, Cold Spring Harbor, N.Y., pp. 172-189, 1988; and Mathew, *Plant Viruses Online* (http://image.fs.uidaho.edu/vide/). In certain embodiments, rather than delivering a single viral vector to a plant cell, multiple different vectors are delivered which, together, allow for replication (and, optionally cell-to-cell and/or long distance movement) of viral vector(s). Some or all proteins may be encoded by the genome of transgenic plants. In certain aspects, described in further detail herein, these systems include one or more viral vector components.

Vector systems that include components of two heterologous plant viruses in order to achieve a system that readily infects a wide range of plant types and yet poses little or no risk of infectious spread. An exemplary system has been described previously (see, e.g., PCT Publication WO 00/25574 and U.S. Patent Publication 2005/0026291, both of which are incorporated herein by reference). As noted herein, in particular aspects of the invention, viral vectors are applied to plants (e.g., plant, portion of plant, sprout, etc.), for example, through infiltration or mechanical inoculation, spray, etc. Where infection is to be accomplished by direct application of a viral genome to a plant, any available technique may be used to prepare the genome. For example, many viruses that are usefully employed in accordance with the present invention have ssRNA genomes. ssRNA may be prepared by transcription of a DNA copy of the genome, or by replication of an RNA copy, either in vivo or in vitro. Given the readily availability of easy-to-use in vitro transcription systems (e.g., SP6, T7, reticulocyte lysate, etc.), and also the convenience of maintaining a DNA copy of an RNA vector, it is expected that ssRNA vectors will often be prepared by in vitro transcription, particularly with T7 or SP6 polymerase.

In certain embodiments, rather than introducing a single viral vector type into a plant, multiple different viral vectors are introduced. Such vectors may, for example, trans-complement each other with respect to functions such as replication, cell-to-cell movement, and/or long distance movement. Vectors may contain different polynucleotides encoding *Y. pestis* antigen in accordance with the invention. Selection for plant(s) or portions thereof that express multiple polypeptides encoding one or more *Y. pestis* antigen(s) may be performed as described above for single polynucleotides or polypeptides.

Plant Tissue Expression Systems

As discussed above, in accordance with the present invention, *Y. pestis* antigens may be produced in any desirable system. Vector constructs and expression systems are well known in the art and may be adapted to incorporate use of *Y. pestis* antigens provided herein. For example, transgenic plant production is known and generation of constructs and plant production may be adapted according to known techniques in the art. In some embodiments, transient expression systems in plants are desirable. Two of these systems include production of clonal roots and clonal plant systems, and derivatives thereof, as well as production of sprouted seedlings systems.

Clonal Plants

Clonal roots maintain RNA viral expression vectors and stably produce target protein uniformly in an entire root over extended periods of time and multiple subcultures. In contrast to plants, where a target gene is eliminated via recombination during cell-to-cell or long distance movement, in root cultures the integrity of a viral vector is maintained and levels of target protein produced over time are similar to those observed during initial screening. Clonal roots allow for ease of production of heterologous protein material for oral formulation of antigen and vaccine compositions. Methods and reagents for generating a variety of clonal entities derived from plants which are useful for production of antigen (e.g., antigen proteins in accordance with the invention) have been described previously and are known in the art (see, for example, PCT Publication WO 05/81905, which is incorporated herein by reference). Clonal entities include clonal root lines, clonal root cell lines, clonal plant cell lines, and clonal plants capable of production of antigen (e.g., antigen proteins in accordance with the invention). The invention further provides methods and reagents for expression of antigen polynucleotide and polypeptide products in clonal cell lines derived from various plant tissues (e.g., roots, leaves), and in whole plants derived from single cells (clonal plants). Such methods are typically based on use of plant viral vectors of various types.

For example, in one aspect, the invention provides methods of obtaining a clonal root line that expresses a polynucleotide encoding a *Y. pestis* antigen in accordance with the invention comprising steps of: (i) introducing a viral vector that comprises a polynucleotide encoding a *Y. pestis* antigen into a plant or portion thereof; and (ii) generating one or more clonal root lines from a plant. Clonal root lines may be generated, for example, by infecting a plant or plant portion (e.g., a harvested piece of leaf) with an *Agrobacterium* (e.g., *A. rhizogenes*) that causes formation of hairy roots. Clonal root lines can be screened in various ways to identify lines that maintain virus, lines that express a polynucleotide encoding a *Y. pestis* antigen at high levels, etc. The invention further provides clonal root lines, e.g., clonal root lines produced in accordance with the invention and further encompasses methods of expressing polynucleotides and producing polypeptide(s) encoding *Y. pestis* antigen(s) using clonal root lines.

The invention further provides methods of generating a clonal root cell line that expresses a polynucleotide encoding a *Y. pestis* antigen in accordance with the invention comprising steps of: (i) generating a clonal root line, cells of which contain a viral vector whose genome comprises a polynucleotide encoding a *Y. pestis* antigen; (ii) releasing individual cells from a clonal root line; and (iii) maintaining cells under conditions suitable for root cell proliferation. The invention provides clonal root cell lines and methods of expressing polynucleotides and producing polypeptides using clonal root cell lines.

In one aspect, the invention provides methods of generating a clonal plant cell line that expresses a polynucleotide encoding a *Y. pestis* antigen in accordance with the invention comprising steps of: (i) generating a clonal root line, cells of which contain a viral vector whose genome comprises a polynucleotide encoding a *Y. pestis* antigen; (ii) releasing individual cells from a clonal root line; and (iii) maintaining cells in culture under conditions appropriate for plant cell proliferation. The invention further provides methods of generating a clonal plant cell line that expresses a polynucleotide encoding a *Y. pestis* antigen comprising steps of: (i) introducing a viral vector that comprises a polynucleotide encoding a *Y. pestis* antigen into cells of a plant cell line maintained in culture; and (ii) enriching for cells that contain viral vector. Enrichment may be performed, for example, by (i) removing a portion of cells from culture; (ii) diluting removed cells so as to reduce cell concentration; (iii) allowing diluted cells to proliferate; and (iv) screening for cells that contain viral vector. Clonal plant cell lines may be used for production of a *Y. pestis* antigen in accordance with the present invention.

The invention includes a number of methods for generating clonal plants, cells of which contain a viral vector that comprises a polynucleotide encoding *Y. pestis* antigen in accordance with the invention. For example, the invention provides methods of generating a clonal plant that expresses a polynucleotide encoding *Y. pestis* antigen comprising steps of: (i) generating a clonal root line, cells of which contain a viral vector whose genome comprises a polynucleotide encoding *Y. pestis* antigen; (ii) releasing individual cells from a clonal root line; and (iii) maintaining released cells under conditions appropriate for formation of a plant. The invention further provides methods of generating a clonal plant that expresses a polynucleotide encoding *Y. pestis* antigen comprising steps of: (i) generating a clonal plant cell line, cells of which contain a viral vector whose genome comprises a polynucleotide encoding a *Y. pestis* antigen; and (ii) maintaining cells under conditions appropriate for formation of a plant. In general, clonal plants according to the invention can express any polynucleotide encoding a *Y. pestis* antigen. Such clonal plants can be used for production of an antigen polypeptide.

As noted above, the present invention provides systems for expressing a polynucleotide or polynucleotide(s) encoding *Y. pestis* antigen(s) in accordance with the invention in clonal root lines, clonal root cell lines, clonal plant cell lines (e.g., cell lines derived from leaf, stem, etc.), and in clonal plants. A polynucleotide encoding a *Y. pestis* antigen is introduced into an ancestral plant cell using a plant viral vector whose genome includes polynucleotide encoding a *Y. pestis* antigen operably linked to (i.e., under control of) a promoter. A clonal root line or clonal plant cell line is established from a cell containing virus according to any of several techniques further described below. A plant virus vector or portions thereof can be introduced into a plant cell by infection, by inoculation with a viral transcript or infectious cDNA clone, by electroporation, by T-DNA mediated gene transfer, etc.

The following sections describe methods for generating clonal root lines, clonal root cell lines, clonal plant cell lines, and clonal plants that express a polynucleotide encoding a *Y. pestis* antigen in accordance with the invention are then described. A "root line" is distinguished from a "root cell line" in that a root line produces actual root-like structures or roots while a root cell line consists of root cells that do not form root-like structures. Use of the term "line" is intended to indicate that cells of a line can proliferate and pass genetic information on to progeny cells. Cells of a cell line typically proliferate in culture without being part of an organized structure such as those found in an intact plant. Use of the term "root line" is intended to indicate that cells in a root structure can proliferate without being part of a complete plant. It is noted that the term "plant cell" encompasses root cells. However, to distinguish methods in accordance with the invention for generating root lines and root cell lines from those used to directly generate plant cell lines from non-root tissue (as opposed to generating clonal plant cell lines from clonal root lines or clonal plants derived from clonal root lines), the terms "plant cell" and "plant cell line" as used herein generally refer to cells and cell lines that consist of non-root plant tissue. Plant cells can be, for example, leaf, stem, shoot, flower part, etc. It is noted that seeds can be derived from clonal plants generated as derived herein. Such seeds may contain viral vector as will plants obtained from such seeds. Methods for obtaining seed stocks are well known in the art (see, for example, U.S Patent Publication 2004/093643; incorporated herein by reference).

Clonal Root Lines

The present invention provides systems for generating a clonal root line in which a plant viral vector is used to direct expression of a polynucleotide encoding a *Y. pestis* antigen in accordance with the invention. One or more viral expression vector(s) including a polynucleotide encoding a *Y. pestis* antigen operably linked to a promoter is introduced into a plant or a portion thereof according to any of a variety of known methods. For example, plant leaves can be inoculated with viral transcripts. Vectors themselves may be directly applied to plants (e.g., via abrasive inoculations, mechanized spray inoculations, vacuum infiltration, particle bombardment, or electroporation). Alternatively or additionally, virions may be prepared (e.g., from already infected plants), and may be applied to other plants according to known techniques.

Where infection is to be accomplished by direct application of a viral genome to a plant, any available technique may be used to prepare viral genome. For example, many viruses that are usefully employed in accordance with the present invention have ssRNA genomes. ssRNA may be prepared by transcription of a DNA copy of the genome, or by replication of an RNA copy, either in vivo or in vitro. Given the readily available, easy-to-use in vitro transcription systems (e.g., SP6, T7, reticulocyte lysate, etc.), and also the convenience of maintaining a DNA copy of an RNA vector, it is expected that ssRNA vectors will often be prepared by in vitro transcription, particularly with T7 or SP6 polymerase. Infectious cDNA clones can be used. Agrobacterially-mediated gene transfer can be used to transfer viral nucleic acids such as viral vectors (either entire viral genomes or portions thereof) to plant cells using, e.g., agroinfiltration, according to methods known in the art.

A plant or plant portion may then be then maintained (e.g., cultured or grown) under conditions suitable for replication of viral transcript. In certain embodiments in accordance with the invention virus spreads beyond the initially inoculated cell, e.g., locally from cell to cell and/or systemically from an initially inoculated leaf into additional leaves. However, in some embodiments, virus does not spread. Thus viral vector may contain genes encoding functional MP and/or CP, but may be lacking one or both of such genes. In general, viral vector is introduced into (infects) multiple cells in the plant or portion thereof.

Following introduction of viral vector into a plant, leaves are harvested. In general, leaves may be harvested at any time following introduction of a viral vector. However, it may be desirable to maintain a plant for a period of time following introduction of a viral vector into a plant, e.g., a period of time sufficient for viral replication and, optionally, spread of virus from cells into which it was initially introduced. A clonal root culture (or multiple cultures) is prepared, e.g., by known methods further described below.

In general, any available method may be used to prepare a clonal root culture from a plant or plant tissue into which a viral vector has been introduced. One such method employs genes that exist in certain bacterial plasmids. These plasmids are found in various species of *Agrobacterium* that infect and transfer DNA to a wide variety of organisms. As a genus, *Agrobacteria* can transfer DNA to a large and diverse set of plant types including numerous dicot and monocot angiosperm species and gymnosperms (see, for example, Gelvin, 2003, *Microbiol. Mol. Biol. Rev.*, 67:16, and references therein, all of which are incorporated herein by reference). The molecular basis of genetic transformation of plant cells is transfer from bacterium and integration into plant nuclear genome of a region of a large tumor-inducing (Ti) or rhizogenic (Ri) plasmid that resides within various *Agrobacterial* species. This region is referred to as the T-region when present in the plasmid and as T-DNA when excised from plasmid. Generally, a single-stranded T-DNA molecule is transferred to a plant cell in naturally occurring *Agrobacterial* infection and is ultimately incorporated (in double-stranded form) into the genome. Systems based on Ti plasmids are widely used for introduction of foreign genetic material into plants and for production of transgenic plants.

Infection of plants with various *Agrobacterial* species and transfer of T-DNA has a number of effects. For example, *A. tumefaciens* causes crown gall disease while *A. rhizogenes* causes development of hairy roots at the site of infection, a condition known as "hairy root disease." Each root arises from a single genetically transformed cell. Thus root cells in roots are clonal, and each root represents a clonal population of cells. Roots produced by *A. rhizogenes* infection are characterized by a high growth rate and genetic stability (Giri et al., 2000, *Biotech. Adv.*, 18:1, and references therein, all of which are incorporated herein by reference). In addition, such roots are able to regenerate genetically stable plants (Giri 2000, supra).

In general, the present invention encompasses use of any strain of *Agrobacteria*, particularly *A. rhizogenes* strains, that is capable of inducing formation of roots from plant cells. As mentioned above, a portion of the Ri plasmid (Ri T-DNA) is responsible for causing hairy root disease. While transfer of this portion of the Ri plasmid to plant cells can conveniently be accomplished by infection with *Agrobacteria* harboring the Ri plasmid, the invention encompasses use of alternative methods of introducing the relevant region into a plant cell. Such methods include any available method of introducing genetic material into plant cells including, but not limited to, biolistics, electroporation, PEG-mediated DNA uptake, Ti-based vectors, etc. The relevant portions of Ri T-DNA can be introduced into plant cells by use of a viral vector. Ri genes can be included in the same vector that contains a polynucleotide encoding a *Y. pestis* antigen in accordance with the invention or in a different viral vector, which can be the same or a different type to that of the vector that contains a polynucleotide encoding a *Y. pestis* antigen in accordance with the invention. It is noted that the entire Ri T-DNA may not be required for production of hairy roots, and the invention encompasses use of portions of Ri T-DNA, provided that such portions contain sufficient genetic material to induce root formation, as known in the art. Additional genetic material, e.g., genes present within the Ri plasmid but not within T-DNA, may be transferred to a plant cell in accordance with the invention, particularly genes whose expression products facilitate integration of T-DNA into plant cell DNA.

In order to prepare a clonal root line in accordance with certain embodiments, harvested leaf portions are contacted with *A. rhizogenes* under conditions suitable for infection and transformation. Leaf portions are maintained in culture to allow development of hairy roots. Each root is clonal, i.e., cells in the root are derived from a single ancestral cell into which Ri T-DNA was transferred. In accordance with the invention, a portion of such ancestral cells will contain a viral vector. Thus cells in a root derived from such an ancestral cell may contain viral vector since it will be replicated and will be transmitted during cell division. Thus a high proportion (e.g. at least 50%, at least 75%, at least 80%, at least 90%, at least 95%), all (i.e., 100%), or substantially all (e.g., at least 98%) of cells will contain viral vector. It is noted that since viral vector is inherited by daughter cells within a clonal root, movement of viral vector within the root is not necessary to maintain viral vector throughout the root. Individual clonal hairy roots may be removed from the leaf portion and further cultured. Such roots are also referred to herein as root lines. Isolated clonal roots continue to grow following isolation.

A variety of different clonal root lines have been generated using methods in accordance with the invention. These root lines were generated using viral vectors containing polynucleotide(s) encoding a *Y. pestis* antigen in accordance with the invention (e.g., encoding including *Y. pestis* protein(s), portions, fragments, domains, variants, and/or fusions thereof). Root lines were tested by western blot. Root lines displayed a variety of different expression levels of various polypeptides. Root lines displaying high expression were selected and further cultured. These root lines were subsequently tested again and shown to maintain high levels of expression over extended periods of time, indicating stability. Expression levels were comparable to or greater than expression in intact plants infected with the same viral vector used to generate clonal root lines. In addition, stability of expression of root lines was superior to that obtained in plants infected with the same viral vector. Up to 80% of such virus-infected plants reverted to wild type after 2-3 passages. (Such passages involved inoculating plants with transcripts, allowing infection (local or systemic) to become established, taking a leaf sample, and inoculating fresh plants that are subsequently tested for expression).

Root lines may be cultured on a large scale for production of antigen in accordance with the invention polypeptides as discussed further below. It is noted that clonal root lines (and cell lines derived from clonal root lines) can generally be maintained in medium that does not include various compounds, e.g., plant growth hormones such as auxins, cytokinins, etc., that are typically employed in culture of root and plant cells. This feature greatly reduces expense associated with tissue culture, and the inventors expect that it will contribute significantly to economic feasibility of protein production using plants.

Any of a variety of methods may be used to select clonal roots that express a polynucleotide encoding *Y. pestis* antigen(s) in accordance with the invention. Western blots, ELISA assays, etc., can be used to detect an encoded polypeptide. In the case of detectable markers such as GFP, alternative methods such as visual screens can be performed. If a viral vector that contains a polynucleotide that encodes a selectable marker is used, an appropriate selection can be imposed (e.g., leaf material and/or roots derived therefrom can be cultured in the presence of an appropriate antibiotic or nutritional condition and surviving roots identified and isolated). Certain viral vectors contain two or more polynucleotide(s) encoding *Y. pestis* antigen(s) in accordance with the invention, e.g., two or more polynucleotides encoding different polypeptides. If one of these is a selectable or detectable marker, clonal roots that are selected or detected by selecting for or detecting expression of a marker will have a high probability of also expressing a second polynucleotide. Screening for root lines that contain particular polynucleotides can also be performed using PCR and other nucleic acid detection methods.

Alternatively or additionally, clonal root lines can be screened for presence of virus by inoculating host plants that will form local lesions as a result of virus infection (e.g., hypersensitive host plants). For example, 5 mg of root tissue can be homogenized in 50 µl of phosphate buffer and used to inoculate a single leaf of a tobacco plant. If virus is present in root cultures, within two to three days characteristic lesions will appear on infected leaves. This means that root line contains recombinant virus that carries a polynucleotide encoding a *Y. pestis* antigen in accordance with the invention (a target gene). If no local lesions are formed, there is no virus, and the root line is rejected as negative. This method is highly time- and cost-efficient. After initially screening for the presence of virus, roots that contain virus may be subjected to secondary screening, e.g., by western blot or ELISA to select high expressers. Additional screens, e.g., screens for rapid growth, growth in particular media or under particular environmental conditions, etc., can be applied. These screening methods may, in general, be applied in the development of any of clonal root lines, clonal root cell lines, clonal plant cell lines, and/or clonal plants described herein.

As will be evident to one of ordinary skill in the art, a variety of modifications may be made to the description of methods in accordance with the invention for generating clonal root lines that contain a viral vector. Such modifications are within the scope of the invention. For example, while it is generally desirable to introduce viral vector into an intact plant or portion thereof prior to introduction of Ri T-DNA genes, in certain embodiments, Ri-DNA is introduced prior to introducing viral vector. In addition, it is possible to contact intact plants with *A. rhizogenes* rather than harvesting leaf portions and then exposing them to bacterium.

Other methods of generating clonal root lines from single cells of a plant or portion thereof that harbor a viral vector can be used (i.e., methods not using *A. rhizogenes* or genetic material from the Ri plasmid). For example, treatment with certain plant hormones or combinations of plant hormones is known to result in generation of roots from plant tissue.

Clonal Cell Lines Derived from Clonal Root Lines

As described above, the invention provides methods for generating clonal root lines, wherein cells in root lines contain a viral vector. As is well known in the art, a variety of different cell lines can be generated from roots. For example, root cell lines can be generated from individual root cells obtained from a root using a variety of known methods. Such root cell lines may be obtained from various different root cell types within a root. In general, root material is harvested and dissociated (e.g., physically and/or enzymatically digested) to release individual root cells, which are then further cultured. Complete protoplast formation is generally not necessary. If desired, root cells can be plated at very dilute cell concentrations, so as to obtain root cell lines from single root cells. Root cell lines derived in this manner are clonal root cell lines containing viral vector. Such root cell lines therefore exhibit stable expression of a polynucleotide encoding a *Y. pestis* antigen in accordance with the invention. Clonal plant cell lines can be obtained in a similar manner from clonal roots, e.g., by culturing dissociated root cells in the presence of appropriate plant hormones. Screens and successive rounds of enrichment can be used to identify cell lines that express a polynucleotide encoding a *Y. pestis* antigen at high levels. However, if the clonal root line from which a cell line is derived already expresses at high levels, such additional screens may be unnecessary.

As in the case of clonal root lines, cells of a clonal root cell line are derived from a single ancestral cell that contains viral vector and will, therefore, also contain viral vector since it will be replicated and will be transmitted during cell division. Thus a high proportion (e.g. at least 50%, at least 75%, at least 80%, at least 90%, at least 95%), all (i.e., 100%), or substantially all (e.g., at least 98%) of cells will contain viral vector. It is noted that since viral vector is inherited by daughter cells within a clonal root cell line, movement of viral vector among cells is not necessary to maintain viral vector. Clonal root cell lines can be used for production of a polynucleotide encoding *Y. pestis* antigen as described below.

Clonal Plant Cell Lines

The present invention provides methods for generating a clonal plant cell line in which a plant viral vector is used to direct expression of a polynucleotide encoding a *Y. pestis* antigen in accordance with the invention. According to methods in accordance with the invention, one or more viral expression vector(s) including a polynucleotide encoding a *Y. pestis* antigen operably linked to a promoter is introduced into cells of a plant cell line that is maintained in cell culture. A number of plant cell lines from various plant types are known in the art, any of which can be used. Newly derived cell lines can be generated according to known methods for use in practicing the invention. A viral vector is introduced into cells of a plant cell line according to any of a number of methods. For example, protoplasts can be made and viral transcripts then electroporated into cells. Other methods of introducing a plant viral vector into cells of a plant cell line can be used.

A method for generating clonal plant cell lines in accordance with the invention and a viral vector suitable for introduction into plant cells (e.g., protoplasts) can be used as follows: Following introduction of viral vector, a plant cell line may be maintained in tissue culture. During this time viral vector may replicate, and polynucleotide(s) encoding a *Y. pestis* antigen(s) may be expressed. Clonal plant cell lines are derived from culture, e.g., by a process of successive enrichment. For example, samples may be removed from culture, optionally with dilution so that the concentration of cells is low, and plated in Petri dishes in individual droplets. Droplets are then maintained to allow cell division.

It will be appreciated that droplets may contain a variable number of cells, depending on initial density of the culture and amount of dilution. Cells can be diluted such that most droplets contain either 0 or 1 cell if it is desired to obtain clonal cell lines expressing a polynucleotide encoding a *Y. pestis* antigen after only a single round of enrichment. However, it can be more efficient to select a concentration such that multiple cells are present in each droplet and then screen droplets to identify those that contain expressing cells. In general, any appropriate screening procedure can be employed. For example, selection or detection of a detectable marker such as GFP can be used. Western blots or ELISA assays can be used. Individual droplets (100 µl) contain more than enough cells for performance of these assays. Multiple rounds of enrichment are performed to isolate successively higher expressing cell lines. Single clonal plant cell lines (i.e., populations derived from a single ancestral cell) can be generated by further limiting dilution using standard methods for single cell cloning. However, it is not necessary to isolate individual clonal lines. A population containing multiple clonal cell lines can be used for expression of a polynucleotide encoding one or more *Y. pestis* antigen(s).

In general, certain considerations described above for generation of clonal root lines apply to generation of clonal plant cell lines. For example, a diversity of viral vectors containing one or more polynucleotide(s) encoding a *Y. pestis* antigen(s) in accordance with the invention can be used as combinations of multiple different vectors. Similar screening methods can be used. As in the case of clonal root lines and clonal root cell lines, cells of a clonal plant cell line are derived from a single ancestral cell that contains viral vector and will, therefore, also contain viral vector since it will be replicated and will be transmitted during cell division. Thus a high proportion (e.g. at least 50%, at least 75%, at least 80%, at least 90%, at least 95%), all (i.e., 100%), or substantially all (e.g., at least 98%) of cells will contain viral vector. It is noted that since viral vector is inherited by daughter cells within a clonal plant cell line, movement of viral vector among cells is not necessary to maintain viral vector. A clonal plant cell line can be used for production of a polypeptide encoding a *Y. pestis* antigen as described below.

Clonal Plants

Clonal plants can be generated from clonal roots, clonal root cell lines, and/or clonal plant cell lines produced according to various methods described above. Methods for generation of plants from roots, root cell lines, and plant cell lines such as clonal root lines, clonal root cell lines, and clonal plant cell lines described herein are well known in the art (see, e.g., Peres et al., 2001, *Plant Cell, Tissue, Organ Culture*, 65:37; and standard reference works on plant molecular biology and biotechnology cited elsewhere herein). The invention therefore provides a method of generating a clonal plant comprising steps of (i) generating a clonal root line, clonal root cell line, or clonal plant cell line according to any of the methods described above; and (ii) generating a whole plant from a clonal root line, clonal root cell line, or clonal plant. Clonal plants may be propagated and grown according to standard methods.

As in the case of clonal root lines, clonal root cell lines, and clonal plant cell lines, cells of a clonal plant are derived from a single ancestral cell that contains viral vector and will, therefore, also contain viral vector since it will be replicated and will be transmitted during cell division. Thus a high proportion (e.g. at least 50%, at least 75%, at least 80%, at least 90%, at least 95%), all (i.e., 100%), or substantially all (e.g., at least 98%) of cells will contain viral vector. It is noted that since viral vector is inherited by daughter cells within a clonal plant, movement of viral vector is not necessary to maintain viral vector.

Sprouts and Sprouted Seedling Plant Expression Systems

Systems and reagents for generating a variety of sprouts and sprouted seedlings which are useful for production of *Y. pestis* antigen(s) according to the present invention have been described previously and are known in the art (see, for example, PCT Publication WO 04/43886; incorporated herein by reference). The present invention further provides sprouted seedlings, which may be edible, as a biomass containing a *Y. pestis* antigen. In certain aspects, biomass is provided directly for consumption of antigen containing compositions. In some aspects, biomass is processed prior to consumption, for example, by homogenizing, crushing, drying, or extracting. In certain aspects, *Y. pestis* antigen is purified from biomass and formulated into a pharmaceutical composition.

Additionally provided are methods for producing *Y. pestis* antigen(s) in sprouted seedlings that can be consumed or harvested live (e.g., sprouts, sprouted seedlings of the *Brassica* genus). In certain aspects, the present invention involves growing a seed to an edible sprouted seedling in a contained, regulatable environment (e.g., indoors, in a container, etc.). A seed can be a genetically engineered seed that contains an expression cassette encoding a *Y. pestis* antigen, which expression is driven by an exogenously inducible promoter. A variety of exogenously inducible promoters can be used that are inducible, for example, by light, heat, phytohormones, nutrients, etc.

In related embodiments, the present invention provides methods of producing *Y. pestis* antigen(s) in sprouted seedlings by first generating a seed stock for a sprouted seedling by transforming plants with an expression cassette that encodes *Y. pestis* antigen using an *Agrobacterium* transformation system, wherein expression of a *Y. pestis* antigen is driven by an inducible promoter. Transgenic seeds can be obtained from a transformed plant, grown in a contained, regulatable environment, and induced to express a *Y. pestis* antigen.

In some embodiments methods are provided that involves infecting sprouted seedlings with a viral expression cassette encoding a *Y. pestis* antigen, expression of which may be driven by any of a viral promoter or an inducible promoter. Sprouted seedlings are grown for two to fourteen days in a contained, regulatable environment or at least until sufficient levels of *Y. pestis* antigen have been obtained for consumption or harvesting.

The present invention further provides systems for producing *Y. pestis* antigen(s) in sprouted seedlings that include a housing unit with climate control and a sprouted seedling containing an expression cassette that encodes one or more *Y. pestis* antigens, wherein expression is driven by a constitutive or inducible promoter. Systems can provide unique advantages over an outdoor environment or greenhouse, which cannot be controlled. Thus, the present invention enables a grower to precisely time induction of expression of *Y. pestis* antigen. It can greatly reduce time and cost of producing *Y. pestis* antigen(s).

In certain aspects, transiently transfected sprouts contain viral vector sequences encoding a *Y. pestis* antigen in accordance with the invention. Seedlings are grown for a time period so as to allow for production of viral nucleic acid in sprouts, followed by a period of growth wherein multiple copies of virus are produced, thereby resulting in production of *Y. pestis* antigen(s).

In certain aspects, genetically engineered seeds or embryos that contain a nucleic acid encoding *Y. pestis* antigen(s) are grown to sprouted seedling stage in a contained, regulatable environment. A contained, regulatable environment may be a housing unit or room in which seeds can be grown indoors. All environmental factors of a contained, regulatable environment may be controlled. Since sprouts do not require light to grow, and lighting can be expensive, genetically engineered seeds or embryos may be grown to sprouted seedling stage indoors in absence of light.

Other environmental factors that can be regulated in a contained, regulatable environment in accordance with the invention include temperature, humidity, water, nutrients, gas (e.g., $O_2$ or $CO_2$ content or air circulation), chemicals (small molecules such as sugars and sugar derivatives or hormones such as such as phytohormones gibberellic or absisic acid, etc.) and the like.

According to certain methods, expression of a nucleic acid encoding a *Y. pestis* antigen may be controlled by an exogenously inducible promoter. Exogenously inducible promoters are caused to increase or decrease expression of a nucleic acid in response to an external, rather than an internal stimulus. A number of environmental factors can act as inducers for expression of nucleic acids carried by expression cassettes of genetically engineered sprouts. A promoter may be a heat-inducible promoter, such as a heat-shock promoter. For example, using as heat-shock promoter, temperature of a contained environment may simply be raised to induce expression of a nucleic acid. Other promoters include light inducible promoters. Light-inducible promoters can be maintained as constitutive promoters if light in a contained regulatable environment is always on. Alternatively or additionally, expression of a nucleic acid can be turned on at a particular time during development by simply turning on a light. A promoter may be a chemically inducible promoter is used to induce expression of a nucleic acid. According to these embodiments, a chemical could simply be misted or sprayed onto seed, embryo, or seedling to induce expression of nucleic acid. Spraying and misting can be precisely controlled and directed onto target seed, embryo, or seedling to which it is intended. A contained environment is devoid of wind or air currents, which could disperse chemical away from intended target, so that the chemical stays on the target for which it was intended.

According to the present invention, time of expression is induced can be selected to maximize expression of a *Y. pestis* antigen in sprouted seedling by the time of harvest. Inducing expression in an embryo at a particular stage of growth, for example, inducing expression in an embryo at a particular number of days after germination, may result in maximum synthesis of a *Y. pestis* antigen at the time of harvest. To give but one example, in some situations, inducing expression from a promoter 4 days after germination may result in more protein synthesis than inducing expression from the promoter after 3 days or after 5 days. Those skilled in the art will appreciate that maximizing expression can be achieved by routine experimentation. In certain methods, sprouted seedlings are harvested at about 1, about 2, about 3, about 4, about 5, about 6, about 7, about 8, about 9, about 10, about 11, about 12, about 13, or about 14 days after germination.

In cases where an expression vector has a constitutive promoter instead of an inducible promoter, sprouted seedling may be harvested at a certain time after transformation of sprouted seedling. For example, if a sprouted seedling were virally transformed at an early stage of development, for example, at embryo stage, sprouted seedlings may be harvested at a time when expression is at its maximum post-transformation, e.g., at about 1, about 2, about 3, about 4, about 5, about 6, about 7, about 8, about 9, about 10, about 11, about 12, about 13, or about 14 days post-transformation. It could be that sprouts develop one, two, three or more months post-transformation, depending on germination of seed.

Generally, once expression of *Y. pestis* antigen(s) begins, seeds, embryos, or sprouted seedlings are allowed to grow until sufficient levels of *Y. pestis* antigen(s) are expressed. In certain aspects, sufficient levels are levels that would provide a therapeutic benefit to a patient if harvested biomass were eaten raw. Alternatively or additionally, sufficient levels are levels from which *Y. pestis* antigen can be concentrated or purified from biomass and formulated into a pharmaceutical composition that provides a therapeutic benefit to a patient upon administration. Typically, *Y. pestis* antigen is not a protein expressed in sprouted seedling in nature. At any rate, *Y. pestis* antigen is typically expressed at concentrations above that which would be present in a sprouted seedling in nature.

Once expression of *Y. pestis* antigen is induced, growth is allowed to continue until sprouted seedling stage, at which time sprouted seedlings are harvested. Sprouted seedlings can be harvested live. Harvesting live sprouted seedlings has several advantages including minimal effort and breakage. Sprouted seedlings in accordance with the invention may be grown hydroponically, making harvesting a simple matter of lifting a sprouted seedling from its hydroponic solution. No soil is required for growth of sprouted seedlings, but may be provided if deemed necessary or desirable by the skilled artisan. Because sprouts can be grown without soil, no cleansing of sprouted seedling material is required at the time of harvest. Being able to harvest a sprouted seedling directly from its hydroponic environment without washing or scrubbing minimizes breakage of harvested material. Breakage and wilting of plants induces apoptosis. During apoptosis, certain proteolytic enzymes become active, which can degrade pharmaceutical protein expressed in a sprouted seedling, resulting in decreased therapeutic activity of a protein. Apoptosis-induced proteolysis can significantly decrease yield of protein from mature plants. Using methods in accordance with the invention, apoptosis may be avoided when no harvesting takes place until the moment proteins are extracted from a plant.

For example, live sprouts may be ground, crushed, or blended to produce a slurry of sprouted seedling biomass, in a buffer containing protease inhibitors. Buffer may be maintained at about 4° C. In some aspects, sprouted seedling biomass is air-dried, spray dried, frozen, or freeze-dried. As in mature plants, some of these methods, such as air-drying, may result in a loss of activity of pharmaceutical protein. However, because sprouted seedlings are very small and have a large surface area to volume ratio, this is much less likely to occur. Those skilled in the art will appreciate that many techniques for harvesting biomass that minimize proteolysis of expressed protein are available and could be applied to the present invention.

In some embodiments, sprouted seedlings are edible. In certain embodiments, sprouted seedlings expressing sufficient levels of *Y. pestis* antigens are consumed upon harvesting (e g., immediately after harvest, within minimal period following harvest) so that absolutely no processing occurs before sprouted seedlings are consumed. In this way, any harvest-induced proteolytic breakdown of *Y. pestis* antigen before administration of *Y. pestis* antigen to a patient in need of treatment is minimized. For example, sprouted seedlings that are ready to be consumed can be delivered directly to a patient. Alternatively or additionally, genetically engineered seeds or embryos are delivered to a patient in need of treatment and grown to sprouted seedling stage by a patient. In one aspect, a supply of genetically engineered sprouted seedlings is provided to a patient, or to a doctor who will be treating patients, so that a continual stock of sprouted seedlings expressing certain desirable *Y. pestis* antigens may be cultivated. This may be particularly valuable for populations in developing countries, where expensive pharmaceuticals are not affordable or deliverable. The ease with which sprouted seedlings in accordance with the invention can be grown makes sprouted seedlings in accordance with the invention particularly desirable for such developing populations.

The regulatable nature of a contained environment imparts advantages to the present invention over growing plants in an outdoor environment. In general, growing genetically engineered sprouted seedlings that express pharmaceutical proteins in plants provides a pharmaceutical product faster (e.g., because plants are harvested younger) and with less effort, risk, and regulatory considerations than growing genetically engineered plants. A contained, regulatable environment used in the present invention reduces or eliminates risk of cross-pollinating plants in nature.

For example, a heat inducible promoter likely would not be used outdoors because outdoor temperature cannot be controlled. A promoter would be turned on any time that outdoor temperature rose above a certain level. Similarly, a promoter would be turned off every time outdoor temperature dropped. Such temperature shifts could occur in a single day, for example, turning expression on in the daytime and off at night. A heat inducible promoter, such as those described herein, would not even be practical for use in a greenhouse, which is susceptible to climatic shifts to almost the same degree as outdoors. Growth of genetically engineered plants in a greenhouse is quite costly. In contrast, in the present system, every variable can be controlled so that a maximum amount of expression can be achieved with every harvest.

In certain embodiments, sprouted seedlings in accordance with the invention are grown in trays that can be watered, sprayed, or misted at any time during development of sprouted seedling. For example, a tray may be fitted with one or more watering, spraying, misting, and draining apparatus that can deliver and/or remove water, nutrients, chemicals etc. at specific time and at precise quantities during development of a sprouted seedling. For example, seeds require sufficient moisture to keep them damp. Excess moisture drains through holes in trays into drains in the floor of a room. Typically, drainage water is treated as appropriate for removal of harmful chemicals before discharge back into the environment.

Another advantage of trays is that they can be contained within a very small space. Since no light is required for sprouted seedlings to grow, trays containing seeds, embryos, or sprouted seedlings may be tightly stacked vertically on top of one another, providing a large quantity of biomass per unit floor space in a housing facility constructed specifically for these purposes. In addition, stacks of trays can be arranged in horizontal rows within a housing unit. Once seedlings have grown to a stage appropriate for harvest (about two to fourteen days) individual seedling trays are moved into a processing facility, either manually or by automatic means, such as a conveyor belt.

Systems in accordance with the invention are unique in that they provide a sprouted seedling biomass, which is a source of a *Y. pestis* antigen(s). Whether consumed directly or processed into a form of a pharmaceutical composition, because sprouted seedlings are grown in a contained, regulatable environment, sprouted seedling biomass and/or pharmaceutical composition derived from biomass can be provided to a consumer at low cost. In addition, the fact that conditions for growth of sprouted seedlings can be controlled makes quality and purity of product consistent. A contained, regulatable environment obviates many safety regulations of the EPA that can prevent scientists from growing genetically engineered agricultural products out of doors.

Transformed Sprouts

A variety of methods can be used to transform plant cells and produce genetically engineered sprouted seedlings. Two available methods for transformation of plants that require that transgenic plant cell lines be generated in vitro, followed by regeneration of cell lines into whole plants include *Agrobacterium tumefaciens* mediated gene transfer and microprojectile bombardment or electroporation. Viral transformation is a more rapid and less costly method of transforming embryos and sprouted seedlings that can be harvested without an experimental or generational lag prior to obtaining desired product. For any of these techniques, the skilled artisan would appreciate how to adjust and optimize transformation protocols that have traditionally been used for plants, seeds, embryos, or spouted seedlings.

*Agrobacterium* Transformation Expression Cassettes

*Agrobacterium* is a representative genus of the gram-negative family Rhizobiaceae. This species is responsible for plant tumors such as crown gall and hairy root disease. In dedifferentiated plant tissue, which is characteristic of tumors, amino acid derivatives known as opines are produced by the *Agrobacterium* and catabolized by the plant. Bacterial genes responsible for expression of opines are a convenient source of control elements for chimeric expression cassettes. According to the present invention, *Agrobacterium* transformation system may be used to generate edible sprouted seedlings, which are merely harvested earlier than mature plants. *Agrobacterium* transformation methods can easily be applied to regenerate sprouted seedlings expressing *Y. pestis* antigens.

In general, transforming plants involves transformation of plant cells grown in tissue culture by co-cultivation with an *Agrobacterium tumefaciens* carrying a plant/bacterial vector. The vector contains a gene encoding a *Y. pestis* antigen. An *Agrobacterium* transfers vector to plant host cell and is then eliminated using antibiotic treatment. Transformed plant cells expressing *Y. pestis* antigen are selected, differentiated, and finally regenerated into complete plantlets (Hellens et al., 2000, *Plant Mol. Biol.*, 42:819; Pilon-Smits et al., 1999, *Plant Physiolog.*, 119:123; Barfield et al., 1991, *Plant Cell Reports*, 10:308; and Riva et al., 1998, *J. Biotech.*, 1(3); each of which is incorporated by reference herein).

Expression vectors for use in the present invention include a gene (or expression cassette) encoding a *Y. pestis* antigen designed for operation in plants, with companion sequences upstream and downstream of an expression cassette. Companion sequences are generally of plasmid or viral origin and provide necessary characteristics to a vector to transfer DNA from bacteria to the desired plant host.

A basic bacterial/plant vector construct may desirably provide a broad host range prokaryote replication origin, a prokaryote selectable marker. Suitable prokaryotic selectable markers include resistance toward antibiotics such as ampicillin or tetracycline. Other DNA sequences encoding additional functions that are well known in the art may be present in a vector.

*Agrobacterium* T-DNA sequences are required for *Agrobacterium* mediated transfer of DNA to a plant chromosome. Tumor-inducing genes of T-DNA are typically removed and replaced with sequences encoding a *Y. pestis* antigen. T-DNA border sequences are retained because they initiate integration of T-DNA region into a plant genome. If expression of *Y. pestis* antigen is not readily amenable to detection, a bacterial/plant vector construct may include a selectable marker gene suitable for determining if a plant cell has been transformed, e.g., nptII kanamycin resistance gene. On the same or different bacterial/plant vector (Ti plasmid) are Ti sequences. Ti sequences include virulence genes, which encode a set of proteins responsible for excision, transfer and integration of T-DNA into a plant genome (Schell, 1987, *Science*, 237: 1176; incorporated herein by reference). Other sequences suitable for permitting integration of heterologous sequence into a plant genome may include transposon sequences, and the like, for homologous recombination.

Certain constructs will include an expression cassette encoding an antigen protein. One, two, or more expression cassettes may be used in a given transformation. A recombinant expression cassette contains, in addition to a *Y. pestis* antigen encoding sequence, at least the following elements: a promoter region, plant 5' untranslated sequences, initiation codon (depending upon whether or not an expressed gene has its own), and transcription and translation termination sequences. In addition, transcription and translation terminators may be included in expression cassettes or chimeric genes in accordance with the invention. Signal secretion sequences that allow processing and translocation of a protein, as appropriate, may be included in an expression cassette. A variety of promoters, signal sequences, and transcription and translation terminators are described, for example, in Lawton et al. (1987, *Plant Mol. Biol.*, 9:315; incorporated herein by reference) and in U.S. Pat. No. 5,888,789 (incorporated herein by reference). In addition, structural genes for antibiotic resistance are commonly utilized as a selection factor (Fraley et al. 1983, *Proc. Natl. Acad. Sci., USA*, 80:4803, incorporated herein by reference). Unique restriction enzyme sites at the 5' and 3' ends of a cassette allow for easy insertion into a pre-existing vector. Other binary vector systems for *Agrobacterium*-mediated transformation, carrying at least one T-DNA border sequence are described (PCT/EP99/07414, incorporated herein by reference).

Regeneration

Seeds of transformed plants may be harvested, dried, cleaned, and tested for viability and for presence and expression of a desired gene product. Once this has been determined, seed stock is typically stored under appropriate conditions of temperature, humidity, sanitation, and security to be used when necessary. Whole plants may then be regenerated from cultured protoplasts, e.g., as described in Evans et al. (*Handbook of Plant Cell Cultures*, Vol. 1, MacMillan Publishing Co., New York, N.Y., 1983, incorporated herein by reference); and in Vasil (ed., *Cell Culture and Somatic Cell Genetics of Plants*, Acad. Press, Orlando, Fla., Vol. I, 1984, and Vol. III, 1986, incorporated herein by reference). In certain aspects, plants are regenerated only to sprouted seedling stage. In some aspects, whole plants are regenerated to produce seed stocks and sprouted seedlings are generated from seeds of a seed stock.

All plants from which protoplasts can be isolated and cultured to give whole, regenerated plants can be transformed by the present invention so that whole plants are recovered that contain a transferred gene. It is known that practically all plants can be regenerated from cultured cells or tissues, including, but not limited to, all major species of plants that produce edible sprouts. Some suitable plants include alfalfa, mung bean, radish, wheat, mustard, spinach, carrot, beet, onion, garlic, celery, rhubarb, a leafy plant such as cabbage or lettuce, watercress or cress, herbs such as parsley, mint, or clovers, cauliflower, broccoli, soybean, lentils, edible flowers such as sunflower, etc.

Means for regeneration vary from one species of plants to the next. However, those skilled in the art will appreciate that generally a suspension of transformed protoplants containing copies of a heterologous gene is first provided. Callus tissue is formed and shoots may be induced from callus and subsequently rooted. Alternatively or additionally, embryo formation can be induced from a protoplast suspension. These embryos germinate as natural embryos to form plants. Steeping seed in water or spraying seed with water to increase the moisture content of a seed to between 35%-45% initiates germination. For germination to proceed, seeds are typically maintained in air saturated with water under controlled temperature and airflow conditions. Culture media generally contains various amino acids and hormones, such as auxin and cytokinins. In some embodiments, it is advantageous to add glutamic acid and proline to the medium, especially for such species as alfalfa. Shoots and roots normally develop simultaneously. Efficient regeneration typically depends on the medium, the genotype, and the history of the culture. If these three variables are controlled, then regeneration can be fully reproducible and repeatable.

Mature plants, grown from transformed plant cells, are selfed and non-segregating, homozygous transgenic plants are identified. An inbred plant produces seeds containing antigen-encoding sequences in accordance with the invention. Such seeds can be germinated and grown to sprouted seedling stage to produce $Y.$ $pestis$ antigen(s) according to the present invention.

In related embodiments, seeds may be formed into seed products and sold with instructions on how to grow seedlings to an appropriate sprouted seedling stage for administration or harvesting into a pharmaceutical composition. In some related embodiments, hybrids or novel varieties embodying desired traits may be developed from inbred plants in accordance with the invention.

Direct Integration

Direct integration of DNA fragments into the genome of plant cells by microprojectile bombardment or electroporation may be used in the present invention (see, e.g., Kikkert, et al., 1999, *Plant: J. Tiss. Cult. Assoc.*, 35:43; and Bates, 1994, *Mol. Biotech.*, 2:135; both of which are incorporated herein by reference). More particularly, vectors that express $Y.$ $pestis$ antigen(s) can be introduced into plant cells by a variety of techniques. As described above, vectors may include selectable markers for use in plant cells. Vectors may include sequences that allow their selection and propagation in a secondary host, such as sequences containing an origin of replication and selectable marker. Typically, secondary hosts include bacteria and yeast. In some embodiments, a secondary host is bacteria (e.g., *Escherichia coli*, the origin of replication is a colE1-type origin of replication) and a selectable marker is a gene encoding ampicillin resistance. Such sequences are well known in the art and are commercially available (e.g., Clontech, Palo Alto, Calif. or Stratagene, La Jolla, Calif.).

Vectors in accordance with the invention may be modified to intermediate plant transformation plasmids that contain a region of homology to an *Agrobacterium tumefaciens* vector, a T-DNA border region from *Agrobacterium tumefaciens*, and antigen encoding nucleic acids or expression cassettes described above. Further vectors may include a disarmed plant tumor inducing plasmid of *Agrobacterium tumefaciens*.

According to this embodiment, direct transformation of vectors invention may involve microinjecting vectors directly into plant cells by use of micropipettes to mechanically transfer recombinant DNA (see, e.g., Crossway, 1985, *Mol. Gen. Genet.*, 202:179, incorporated herein by reference). Genetic material may be transferred into a plant cell using polyethylene glycols (see, e.g., Krens et al., 1982, *Nature* 296:72; incorporated herein by reference). Another method of introducing nucleic acids into plants via high velocity ballistic penetration by small particles with a nucleic acid either within the matrix of small beads or particles, or on the surface (see, e.g., Klein et al., 1987, *Nature* 327:70; and Knudsen et al., *Planta,* 185:330; both of which are incorporated herein by reference). Yet another method of introduction is fusion of protoplasts with other entities, either minicells, cells, lysosomes, or other fusible lipid-surfaced bodies (see, e.g., Fraley et al., 1982, *Proc. Natl. Acad. Sci., USA,* 79:1859; incorporated herein by reference). Vectors in accordance with the invention may be introduced into plant cells by electroporation (see, e.g., Fromm et al. 1985, *Proc. Natl. Acad. Sci., USA,* 82:5824; incorporated herein by reference). According to this technique, plant protoplasts are electroporated in the presence of plasmids containing a gene construct. Electrical impulses of high field strength reversibly permeabilize biomembranes allowing introduction of plasmids. Electroporated plant protoplasts reform the cell wall divide and form plant callus, which can be regenerated to form sprouted seedlings in accordance with the invention. Those skilled in the art will appreciate how to utilize these methods to transform plants cells that can be used to generate edible sprouted seedlings.

Viral Transformation

Similar to conventional expression systems, plant viral vectors can be used to produce full-length proteins, including full length antigen. According to the present invention, plant virus vectors may be used to infect and produce antigen(s) in seeds, embryos, sprouted seedlings, etc. Viral system that can be used to express everything from short peptides to large complex proteins. Specifically, using tobamoviral vectors is described, for example, by McCormick et al. (1999, *Proc. Natl. Acad. Sci., USA,* 96:703; Kumagai et al. 2000, *Gene,* 245:169; and Verch et al., 1998, *J. Immunol. Methods,* 220: 69; all of which are incorporated herein by reference). Thus, plant viral vectors have a demonstrated ability to express short peptides as well as large complex proteins.

In certain embodiments, transgenic sprouts, which express $Y.$ $pestis$ antigen, are generated utilizing a host/virus system. Transgenic sprouts produced by viral infection provide a source of transgenic protein that has already been demonstrated to be safe. For example, sprouts are free of contamination with animal pathogens. Unlike, for example, tobacco, proteins from an edible sprout could at least in theory be used in oral applications without purification, thus significantly reducing costs. In addition, a virus/sprout system offers a much simpler, less expensive route for scale-up and manufacturing, since transgenes are introduced into virus, which can be grown up to a commercial scale within a few days. In contrast, transgenic plants can require up to 5-7 years before sufficient seed or plant material is available for large-scale trials or commercialization.

According to the present invention, plant RNA viruses have certain advantages, which make them attractive as vectors for foreign protein expression. Molecular biology and pathology of a number of plant RNA viruses are well characterized and there is considerable knowledge of virus biology, genetics, and regulatory sequences. Most plant RNA viruses have small genomes and infectious cDNA clones are available to facilitate genetic manipulation. Once infectious virus material enters a susceptible host cell, it replicates to high levels and spreads rapidly throughout an entire sprouted seedling (one to fourteen days post-inoculation, e.g., about 1, about 2, about 3, about 4, about 5, about 6, about 7, about 8, about 9, about 10, about 11, about 12, about 13, or about 14 days post-inoculation). Virus particles are easily and economically recovered from infected sprouted seedling tissue. Viruses have a wide host range, enabling use of a single construct for infection of several susceptible species. These characteristics are readily transferable to sprouts.

Foreign sequences can be expressed from plant RNA viruses, typically by replacing one of the viral genes with desired sequence, by inserting foreign sequences into a virus genome at an appropriate position, or by fusing foreign peptides to structural proteins of a virus. Moreover, any of these approaches can be combined to express foreign sequences by trans-complementation of vital functions of a virus. A number of different strategies exist as tools to express foreign sequences in virus-infected plants using tobacco mosaic virus (TMV), alfalfa mosaic virus (A1MV), and chimeras thereof.

The genome of A1MV is a representative of the Bromoviridae family of viruses and consists of three genomic RNAs (RNAs 1-3) and subgenomic RNA (RNA4). Genomic RNAs1 and 2 encode virus replicase proteins P1 and P2, respectively. Genomic RNA3 encodes cell-to-cell movement protein P3 and coat protein (CP). CP is translated from subgenomic RNA4, which is synthesized from genomic RNA3, and is required to start infection. Studies have demonstrated involvement of CP in multiple functions, including genome activation, replication, RNA stability, symptom formation, and RNA encapsidation (see e.g., Bol et al., 1971, *Virology*, 46:73; Van Der Vossen et al., 1994, *Virology* 202:891; Yusibov et al., *Virology*, 208:405; Yusibov et al., 1998, *Virology*, 242:1; Bol et al., (Review, 100 refs.), 1999, *J. Gen. Virol.*, 80:1089; De Graaff, 1995, *Virology*, 208:583; Jaspars et al., 1974, *Adv. Virus Res.*, 19:37; Loesch-Fries, 1985, *Virology*, 146:177; Neeleman et al., 1991, *Virology*, 181:687; Neeleman et al., 1993, *Virology*, 196: 883; Van Der Kuyl et al., 1991, *Virology*, 183:731; and Van Der Kuyl et al., 1991, *Virology*, 185:496; all of which are incorporated herein by reference).

Encapsidation of viral particles is typically required for long distance movement of virus from inoculated to un-inoculated parts of seed, embryo, or sprouted seedling and for systemic infection. According to the present invention, inoculation can occur at any stage of plant development. In embryos and sprouts, spread of inoculated virus should be very rapid. Virions of A1MV are encapsidated by a unique CP (24 kD), forming more than one type of particle. The size (30 to 60 nm in length and 18 nm in diameter) and shape (spherical, ellipsoidal, or bacilliform) of a particle depends on the size of an encapsidated RNA. Upon assembly, the N-terminus of A1MV CP is thought to be located on the surface of virus particles and does not appear to interfere with virus assembly (Bol et al., 1971, *Virology*, 6:73; incorporated herein by reference). Additionally, ALMV CP with an additional 38-amino acid peptide at its N-terminus forms particles in vitro and retains biological activity (Yusibov et al., 1995, *J. Gen. Virol.*, 77:567; incorporated herein by reference).

A1MV has a wide host range, which includes a number of agriculturally valuable crop plants, including plant seeds, embryos, and sprouts. Together, these characteristics make ALMV CP an excellent candidate as a carrier molecule and A1MV an attractive candidate vector for expression of foreign sequences in a plant at the sprout stage of development. Moreover, upon expression from a heterologous vector such as TMV, A1MV CP encapsidates TMV genome without interfering with virus infectivity (Yusibov et al., 1997, *Proc. Natl. Acad. Sci., USA,* 94:5784, incorporated herein by reference). This allows use of TMV as a carrier virus for A1MV CP fused to foreign sequences.

TMV, the prototype of tobamoviruses, has a genome consisting of a single plus-sense RNA encapsidated with a 17.0 kD CP, which results in rod-shaped particles (about 300 nm in length). CP is the only structural protein of TMV and is required for encapsidation and long distance movement of virus in an infected host (Saito et al., 1990, *Virology* 176:329; incorporated herein by reference). 183 kD and 126 kD proteins are translated from genomic RNA and are required for virus replication (Ishikawa et al., 1986, *Nucleic Acids Res.*, 14:8291; incorporated herein by reference). 30 kD protein is the cell-to-cell movement protein of virus (Meshi et al., 1987, *EMBO J.*, 6:2557; incorporated herein by reference). Movement and coat proteins are translated from subgenomic mRNAs (Hunter et al., 1976, *Nature,* 260:759; Bruening et al., 1976, *Virology,* 71:498; and Beachy et al., 1976, *Virology,* 73:498, each of which is incorporated herein by reference).

Other methods of transforming plant tissues include transforming a flower of a plant. Transformation of *Arabidopsis thaliana* can be achieved by dipping plant flowers into a solution of *Agrobacterium tumefaciens* (Curtis et al., 2001, *Transgenic Res.,* 10:363; and Qing et al., 2000, *Molecular Breeding: New Strategies in Plant Improvement* 1:67; both of which are incorporated herein by reference). Transformed plants are formed in a population of seeds generated by "dipped" plants. At a specific point during flower development, a pore exists in the ovary wall through which *Agrobacterium tumefaciens* gains access to the interior of an ovary. Once inside the ovary, *Agrobacterium tumefaciens* proliferates and transforms individual ovules (Desfeux et al., 2000, *Plant Physiology,* 123:895; incorporated herein by reference). Transformed ovules follow the typical pathway of seed formation within an ovary.

*Agrobacterium*-Mediated Transient Expression

As indicated herein, in many embodiments, systems for rapid (e.g., transient) expression of proteins or polypeptides in plants are desirable. Among other things, the present invention provides a powerful system for achieving such rapid expression in plants that utilizes an agrobacterial construct to deliver a viral expression system encoding a protein or polypeptide of interest. In some embodiments, any of the *Y. pestis* antigens described herein can be expressed utilizing launch vector technology, e.g., as described below. In some embodiments, launch vector constructs can also be utilized in the context of thermostable proteins, as described in more detail in the section entitled "*Y. pestis* Poplypeptide Fusions with Thermostable Proteins."

In some embodiments, according to the present invention, a "launch vector" is prepared that contains agrobacterial sequences including replication sequences and also contains plant viral sequences (including self-replication sequences) that carry a gene encoding a protein or polypeptide of interest. A launch vector is introduced into plant tissue, typically by agroinfiltration, which allows substantially systemic delivery. For transient transformation, non-integrated T-DNA copies of the launch vector remain transiently present in the nucleus and are transcribed leading to expression of the carrying genes (Kapila et al., 1997, *Plant Science,* 122:101-108; incorporated herein by reference). *Agrobacterium*-mediated transient expression, differently from viral vectors, cannot lead to systemic spreading of expression of a gene of interest. One advantage of this system is the possibility to clone genes larger than 2 kb to generate constructs that would be impossible to obtain with viral vectors (Voinnet et al., 2003, *Plant J.*, 33:949-56; incorporated herein by reference). Furthermore, using such technique, it is possible to transform a plant with more than one transgene, such that multimeric proteins (e.g., antibodies subunits of complexed proteins) can be expressed and assembled. Furthermore, the possibility of co-expression of multiple transgenes by means of co-infiltration with different *Agrobacterium* can be taken advantage of, either by separate infiltration or using mixed cultures.

In certain embodiments, a launch vector includes sequences that allow for selection (or at least detection) in *Agrobacteria* and for selection/detection in infiltrated tissues. Furthermore, a launch vector typically includes sequences that are transcribed in a plant to yield viral RNA production, followed by generation of viral proteins. Furthermore, production of viral proteins and viral RNA yields rapid production of multiple copies of RNA encoding a pharmaceutically active protein of interest. Such production results in rapid protein production of a target of interest in a relatively short period of time. Thus, a highly efficient system for protein production can be generated.

Agroinfiltration utilizing viral expression vectors can be used to produce limited quantity of protein of interest in order to verify expression levels before deciding if it is worth generating transgenic plants. Alternatively or additionally, agroinfiltration utilizing viral expression vectors is useful for rapid generation of plants capable of producing huge amounts of protein as a primary production platform. Thus, this transient expression system can be used on industrial scale.

Further provided are any of a variety of different *Agrobacterial* plasmids, binary plasmids, or derivatives thereof such as pBIV, pBI1221, pGreen, etc., which can be used in these and other aspects of the invention. Numerous suitable vectors are known in the art and can be directed and/or modified according to methods known in the art, or those described herein so as to utilize in methods described provided herein.

One particular exemplary launch vector is pBID4. This vector contains the 35S promoter of cauliflower mosaic virus (a DNA plant virus) that drives initial transcription of the recombinant viral genome following introduction into plants, and the nos terminator, the transcriptional terminator of *Agrobacterium* nopaline synthase. The vector further contains sequences of the tobacco mosaic virus genome including genes for virus replication (126/183K) and cell-t-cell movement (MP). The vector further contains a gene encoding a polypeptide of interest, inserted into a unique cloning site within the tobacco mosaic virus genome sequences and under the transcriptional control of the coat protein subgenomic mRNA promoter. Because this "target gene" (i.e., gene encoding a protein or polypeptide of interest) replaces coding sequences for the TMV coat protein, the resultant viral vector is naked self-replicating RNA that is less subject to recombination than CP-containing vectors, and that cannot effectively spread and survive in the environment. Left and right border sequences (LB and RB) delimit the region of the launch vector that is transferred into plant cells following infiltration of plants with recombinant *Agrobacterium* carrying the vector. Upon introduction of agrobacteria carrying this vector into plant tissue (typically by agroinfiltration but alternatively by injection or other means), multiple single-stranded DNA (ssDNA) copies of sequence between LB and RB are generated and released in a matter of minutes. These introduced sequences are then amplified by viral replication. Translation of the target gene results in accumulation of large amounts of target protein or polypeptide in a short period of time.

In some embodiments, *Agrobacterium*-mediated transient expression produces up to about 5 g or more of target protein per kg of plant tissue. For example, in some embodiments, up to about 4, about 3, about 2, about 1, or about 0.5 g of target protein is produced per kg of plant tissue. In some embodiments, at least about 20—about 500 mg, or about 50—about 500 of target protein, or about 50—about 200, or about 50, about 60, about 70, about 80, about 90, about 100, about 110, about 120, about 130, about 140, about 150, about 160, about 170, about 180, about 190, about 200, about 250, about 300, about 350, about 400, about 450, about 500, about 550, about 600, about 650, about 700, about 750, about 800, about 850, about 900, about 950, about 1000, about 1500, about 1750, about 2000, about 2500, about 3000 mg, or more of protein per kg of plant tissue is produced.

In some embodiments, these expression levels are achieved within about 6, about 5, about 4, about 3, or about 2 weeks from infiltration. In some embodiments, these expression levels are achieved within about 10, about 9, about 8, about 7, about 6, about 5, about 4, about 3, about 2 days, or even 1 day, from introduction of an expression construct. Thus, the time from introduction (e.g., infiltration) to harvest is typically less than about 2 weeks, less than about 10 days, less than about 1 week, or less than a few days. Furthermore, the invention allows production of protein within about 8 weeks or less from the selection of amino acid sequence (even including time for "preliminary" expression studies). Also, each batch of protein can typically be produced within about 8 weeks, about 6, weeks, about 5 weeks, or less. Those of ordinary skill in the art will appreciate that these numbers may vary somewhat depending on the type of plant used. Most sprouts, including peas, will fall within the numbers given. *Nicotiana benthamiana*, however, may be grown longer, particularly prior to infiltration, as they are slower growing (from a much smaller seed). Other expected adjustments will be clear to those of ordinary skill in the art based on biology of the particular plants utilized. In some embodiments, certain pea varieties including for example, marrowfat pea, bill jump pea, yellow trapper pea, speckled pea, and green pea are particularly useful.

The inventors have also found that various *Nicotiana* plants are particularly useful in the practice of some aspects of the invention, including in particular *Nicotiana benthamiana*. In general, *Nicotiana benthamiana* plants are grown for a time sufficient to allow development of an appropriate amount of biomass prior to infiltration (i.e., to delivery of agrobacteria containing launch vector). Typically, plants are grown for a period of more than about 3 weeks, more typically more than about 4 weeks, or between about 5—about 6 weeks to accumulate biomass prior to infiltration.

The present inventors have further surprisingly found that, although both TMV and A1MV sequences can prove effective in such launch vector constructs, in some embodiments, A1MV sequences are particularly efficient at ensuring high level production of delivered protein or polypeptides.

Thus, in certain particular embodiments, proteins or polypeptides of interest are produced in plants (e.g., *Nicotiana benthamiana*) from a launch vector that directs production of A1MV sequences carrying a gene of interest.

*Yersinia pestis* Poplypeptide Fusions with Thermostable Proteins

In certain aspects, provided are *Y. pestis* antigen(s) comprising fusion polypeptides which comprise a *Y. pestis* protein (or a fragment or variant thereof) operably linked to a thermostable protein (e.g., LicB, LicKM, etc., and described in further detail below). Fusion polypeptides can be produced in any available expression system known in the art (including, but not limited to, launch vector technology). In certain embodiments, fusion proteins are produced in a plant or portion thereof (e.g., plant, plant cell, root, sprout, etc.).

Enzymes or other proteins which are not found naturally in humans or animal cells are particularly appropriate for use in fusion polypeptides in accordance with the invention. Thermostable proteins that, when fused, confer thermostability to a fusion product are useful. Thermostability allows produced protein to maintain conformation, and maintain produced protein at room temperature. This feature facilitates easy, time efficient and cost effective recovery of a fusion polypeptide. A representative family of thermostable enzymes useful in accordance with the invention is the glucanohydrolase family. These enzymes specifically cleave 1,4-β glucosidic bonds that are adjacent to 1,3-β linkages in mixed linked polysaccharides (Hahn et al., 1994 *Proc. Natl. Acad. Sci., USA,* 91:10417; incorporated herein by reference). Such enzymes are found in cereals, such as oat and barley, and are also found in a number of fungal and bacterial species, including *C. thermocellum* (Goldenkova et al., 2002, *Mol. Biol.* 36:698; incorporated herein by reference). Thus, desirable thermostable proteins for use in fusion polypeptides in accordance with the invention include glycosidase enzymes. Exemplary thermostable glycosidase proteins include those represented by GenBank accession numbers selected from those set forth in Table 1, the contents of each of which are incorporated herein by reference by entire incorporation of the GenBank accession information for each referenced number. Exemplary thermostable enzymes of use in fusion proteins in accordance with the invention include *Clostridium thermocellum* P29716, *Brevibacillus brevis* P37073, and *Rhodthermus marinus* P45798, each of which are incorporated herein by reference to their GenBank accession numbers. Representative fusion proteins illustrated in the Examples utilize modified thermostable enzyme isolated from *Clostridium thermocellum,* however, any thermostable protein may be similarly utilized in accordance with the present invention.

TABLE 1

Thermostable Glycosidase Proteins

| | |
|---|---|
| P29716 | (Beta-glucanase *Clostridium thermocellum*) |
| P37073 | (Beta-glucanase *Brevibacillus brevis*) |
| 1MVE_A | (Beta-glucanase *Fibrobacter succinogenes*) |
| P07883 | (Extracellular agarase *Streptomyces coelicolor*) |
| P23903 | (Glucan endo-13-beta-glucosidase A1 *Bacillus circulans*) |
| P27051 | (Beta-glucanase *Bacillus licheniformis*) |
| P45797 | (Beta-glucanase *Paenibacillus polymyxa (Bacillus polymyxa)*) |
| P37073 | (Beta-glucanase *Brevibacillus brevis*) |
| P45798 | (Beta-glucanase *Rhodothermus marinus*) |
| P38645 | (Beta-glucosidase *Thermobispora bispora*) |
| P40942 | (Celloxylanase *Clostridium stercorarium*) |
| P14002 | (Beta-glucosidase *Clostridium thermocellum*) |
| O33830 | (Alpha-glucosidase *Thermotoga maritima*) |
| O43097 | (Xylanase *Thermomyces lanuginosus*) |
| P54583 | (Endo-glucanase E1 *Acidothermus cellulolyticus*) |
| P14288 | (Beta-galactosidase *Sulfolobus acidocaldarius*) |
| O52629 | (Beta-galactosidase *Pyrococcus woesei*) |
| P29094 | (Oligo-16-glucosidase *Geobacillus thermoglucosidasius*) |
| P49067 | (Alpha-amylase *Pyrococcus furiosus*) |
| JC7532 | (Cellulase *Bacillus species*) |
| Q60037 | (Xylanase A *Thermotoga maritima*) |
| P33558 | (Xylanase A *Clostridium stercorarium*) |
| P05117 | (Polygalacturonase-2 precursor *Solanum lycopersicum*) |
| P04954 | (Cellulase D *Clostridium thermocellum*) |
| Q4J929 | (N-glycosylase *Sulfolobus acidocaldarius*) |
| O33833 | (Beta-fructosidase *Thermotoga maritima*) |

TABLE 1-continued

Thermostable Glycosidase Proteins

| | |
|---|---|
| P49425 | (Endo-14-beta-mannosidase *Rhodothermus marinus*) |
| P06279 | (Alpha-amylase *Geobacillus stearothermophilus*) |
| P45702 P45703 P40943 | (Xylanase *Geobacillus stearothermophilus*) |
| P09961 | (Alpha-amylase 1 *Dictyoglomus thermophilum*) |
| Q60042 | (Xylanase A *Thermotoga neapolitana*) |
| AAN05438 AAN05439 | (Beta-glycosidase *Thermus thermophilus*) |
| AAN05437 | (Sugar permease *Thermus thermophilus*) |
| AAN05440 | (Beta-glycosidase *Thermus filiformis*) |
| AAD43138 | (Beta-glycosidase *Thermosphaera aggregans*) |

When designing fusion proteins and polypeptides in accordance with the invention, it is desirable, of course, to preserve immunogenicity of an antigen. Still further, it is desirable in certain aspects to provide constructs which provide thermostability of a fusion protein. This feature facilitates easy, time efficient and cost effective recovery of a target antigen. In certain aspects, antigen fusion partners may be selected which provide additional advantages, including enhancement of immunogenicity, potential to incorporate multiple vaccine determinants, yet lack prior immunogenic exposure to vaccination subjects. Further beneficial qualities of fusion peptides of interest include proteins which provide ease of manipulation for incorporation of one or more antigens, as well as proteins which have potential to confer ease of production, purification, and/or formulation for vaccine preparations. One of ordinary skill in the art will appreciate that three dimensional presentation can affect each of these beneficial characteristics. Preservation of immunity or preferential qualities therefore may affect, for example, choice of fusion partner and/or choice of fusion location (e.g., N-terminus, C-terminus, internal, combinations thereof). Alternatively or additionally, preferences may affects length of segment selected for fusion, whether it be length of antigen, or length of fusion partner selected.

The present inventors have demonstrated successful fusion of a variety of antigens with a thermostable protein. For example, the present inventors have used the thermostable carrier molecule LicB, also referred to as lichenase, for production of fusion proteins. LicB is 1,3-1,4-β glucanase (LicB) from *Clostridium thermocellum* (GenBank accession: X63355 [gi:40697]). LicB belongs to a family of globular proteins. Based on the three dimensional structure of LicB, its N- and C-termini are situated close to each other on the surface, in close proximity to the active domain. LicB also has a loop structure exposed on the surface that is located far from the active domain. We have generated constructs such that the loop structure and N- and C-termini of protein can be used as insertion sites for *Y. pestis* antigen polypeptides. *Y. pestis* antigen polypeptides can be expressed as N- or C-terminal fusions or as inserts into the surface loop. Importantly, LicB maintains its enzymatic activity at low pH and at high temperature (up to about 75° C.). Thus, use of LicB as a carrier molecule contributes advantages, including likely enhancement of target specific immunogenicity, potential to incorporate multiple vaccine determinants, and straightforward formulation of vaccines that may be delivered nasally, orally or parenterally. Furthermore, production of LicB fusions in plants should reduce the risk of contamination with animal or human pathogens. See examples provided herein.

Fusion proteins comprising *Y. pestis* antigen may be produced in any of a variety of expression systems, including both in vitro and in vivo systems. One skilled in the art will readily appreciate that optimization of nucleic acid sequences for a particular expression system is often desirable. For example, in the Exemplification provided herein, optimized sequence for expression of *Y. pestis* antigen-LicKM fusions in plants is provided (see Examples 1 and 2). Thus, any relevant nucleic acid encoding *Y. pestis* antigen(s) fusion protein(s) and fragments thereof in accordance with the invention is intended to be encompassed within nucleic acid constructs.

For production in plant systems, transgenic plants expressing *Y. pestis* antigen(s) (e.g., *Y. pestis* protein(s) or fragments or fusions thereof) may be utilized. Alternatively or additionally, transgenic plants may be produced using methods well known in the art to generate stable production crops. Additionally, plants utilizing transient expression systems may be utilized for production of *Y. pestis* antigen(s). When utilizing plant expression systems, whether transgenic or transient expression in plants is utilized, any of nuclear expression, chloroplast expression, mitochondrial expression, or viral expression may be taken advantage of according to the applicability of the system to antigen desired. Furthermore, additional expression systems for production of antigens and fusion proteins in accordance with the present invention may be utilized. For example, mammalian expression systems (e.g., mammalian cell lines (e.g., CHO, etc.)), bacterial expression systems (e.g., *E. coli*), insect expression systems (e.g., baculovirus), yeast expression systems, and in vitro expression systems (e.g., reticulate lysates) may be used for expression of antigens and fusion proteins in accordance with the invention.

Production and Isolation of Antigen

In general, standard methods known in the art may be used for culturing or growing plants, plant cells, and/or plant tissues in accordance with the invention (e.g., clonal plants, clonal plant cells, clonal roots, clonal root lines, sprouts, sprouted seedlings, plants, etc.) for production of antigen(s). A wide variety of culture media and bioreactors have been employed to culture hairy root cells, root cell lines, and plant cells (see, for example, Giri et al., 2000, *Biotechnol. Adv.*, 18:1; Rao et al., 2002, *Biotechnol. Adv.*, 20:101; and references in both of the foregoing, all of which are incorporated herein by reference). Clonal plants may be grown in any suitable manner.

In a certain embodiments, *Y. pestis* antigens in accordance with the invention may be produced by any known method. In some embodiments, a *Y. pestis* antigen is expressed in a plant or portion thereof. Proteins are isolated and purified in accordance with conventional conditions and techniques known in the art. These include methods such as extraction, precipitation, chromatography, affinity chromatography, electrophoresis, and the like. The present invention involves purification and affordable scaling up of production of *Y. pestis* antigen(s) using any of a variety of plant expression systems known in the art and provided herein, including viral plant expression systems described herein.

In many embodiments, it will be desirable to isolate *Y. pestis* antigen(s) for vaccine products. Where a protein in accordance with the invention is produced from plant tissue(s) or a portion thereof, e.g., roots, root cells, plants, plant cells, that express them, methods described in further detail herein, or any applicable methods known in the art may be used for any of partial or complete isolation from plant material. Where it is desirable to isolate an expression product from some or all of plant cells or tissues that express it, any available purification techniques may be employed. Those of ordinary skill in the art are familiar with a wide range of fractionation and separation procedures (see, for example, Scopes et al., *Protein Purification: Principles and Practice*, 3$^{rd}$ Ed., Janson et al., 1993; *Protein Purification: Principles, High Resolution Methods, and Applications*, Wiley-VCH, 1998; Springer-Verlag, NY, 1993; and Roc, *Protein Purification Techniques*, Oxford University Press, 2001; each of which is incorporated herein by reference). Often, it will be desirable to render a product more than about 50%, about 60%, about 70%, about 80%, about 85%, about 90%, about 91%, about 92%, about 93%, about 94%, about 95%, about 96%, about 97%, about 98%, or about 99% pure. See, e.g., U.S. Pat. Nos. 6,740,740 and 6,841,659 (each of which is incorporated herein by reference) for discussion of certain methods useful for purifying substances from plant tissues or fluids.

Those skilled in the art will appreciate that a method of obtaining desired *Y. pestis* antigen(s) product(s) is by extraction. Plant material (e.g., roots, leaves, etc.) may be extracted to remove desired products from residual biomass, thereby increasing concentration and purity of product. Plants may be extracted in a buffered solution. For example, plant material may be transferred into an amount of ice-cold water at a ratio of one to one by weight that has been buffered with, e.g., phosphate buffer. Protease inhibitors can be added as required. Plant material can be disrupted by vigorous blending or grinding while suspended in buffer solution and extracted biomass removed by filtration or centrifugation. Product carried in solution can be further purified by additional steps or converted to a dry powder by freeze-drying or precipitation. Extraction can be carried out by pressing. Plants or roots can be extracted by pressing in a press or by being crushed as they are passed through closely spaced rollers. Fluids expressed from crushed plants or roots are collected and processed according to methods well known in the art. Extraction by pressing allows release of products in a more concentrated form. However, overall yield of product may be lower than if product were extracted in solution.

Vaccines

The present invention provides pharmaceutical antigen proteins for therapeutic use, such as *Y. pestis* antigen(s) (e.g., *Y. pestis* protein(s) or an immunogenic portion(s) thereof, or fusion proteins comprising *Y. pestis* protein(s) or an immunogenic portion(s) thereof), active as agents for treatment and/or prophylaxis of *Y. pestis* infection. Further, the invention provides vaccines for veterinary use, as *Y. pestis* antigen is active in veterinary applications. In certain embodiments, *Y. pestis* antigen(s) may be produced by plant(s) or portion thereof (e.g., root, cell, sprout, cell line, plant, etc.). In certain embodiments, provided *Y. pestis* antigens are expressed in plants, plant cells, and/or plant tissues (e.g., sprouts, sprouted seedlings, roots, root culture, clonal cells, clonal cell lines, clonal plants, etc.), and can be used directly from plant or partially purified or purified in preparation for pharmaceutical administration to a subject.

The present invention provides plants, plant cells, and plant tissues expressing *Y. pestis* antigen(s) that maintains pharmaceutical activity when administered to a subject in need thereof. Exemplary subjects include vertebrates (e.g., mammals such as humans). According to the present invention, subjects include veterinary subjects such as bovines, ovines, canines, felines, etc. In certain aspects, an edible plant or portion thereof (e.g., sprout, root) is administered orally to a subject in a therapeutically effective amount. In some aspects one or more *Y. pestis* antigen(s) is provided in a pharmaceutical preparation, as described herein.

Vaccine compositions in accordance with the invention comprise one or more *Y. pestis* antigens. In certain embodiments, at least two *Y. pestis* antigens are included in an administered vaccine composition.

According to the present invention, treatment of a subject with a *Y. pestis* antigen vaccine is intended to elicit a physiological effect. A vaccine protein may have healing curative or palliative properties against a disorder or disease and can be administered to ameliorate relieve, alleviate, delay onset of, reverse, and/or lessen symptoms or severity of a disease or disorder. A vaccine comprising a *Y. pestis* antigen may have prophylactic properties and can be used to prevent or delay the onset of a disease or to lessen the severity of such disease, disorder, or pathological condition when it does emerge. A physiological effect elicited by treatment of a subject with antigen according to the present invention can include an effective immune response such that infection by an organism is thwarted.

Pharmaceutical compositions in accordance with the invention can be administered therapeutically or prophylactically. Compositions may be used to treat or prevent a disease. For example, any individual who suffers from a disease (e.g. *Yersinia pestis* infection) or who is at risk of developing a disease may be treated. It will be appreciated that an individual can be considered at risk for developing a disease without having been diagnosed with any symptoms of a disease (e.g. *Yersinia pestis* infection). For example, if an individual is known to have been, or to be intended to be, in situations with relatively high risk of exposure to *Y. pestis* infection, that individual will be considered at risk for developing the disease. Similarly, if members of an individual's family or friends have been diagnosed with *Y. pestis* infection, the individual may be considered to be at risk for developing the disease. In some embodiments, if an individual has come into contact with a non-human animal that has been diagnosed with *Y. pestis* infection (e.g., cat, dog, mouse, rat, horse, etc.), the individual may be considered to be at risk for developing the disease.

Administration

*Yersinia pestis* antigens in accordance with the invention and/or pharmaceutical compositions thereof (e.g., vaccines) may be administered using any amount and any route of administration effective for treatment.

The exact amount required will vary from subject to subject, depending on the species, age, and general condition of the subject, the severity of the infection, the particular composition, its mode of administration, its mode of activity, and the like. *Y. pestis* antigens are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and the severity of the disorder; the activity of the specific *Y. pestis* antigen employed; the specific pharmaceutical composition administered; the half-life of the composition after administration; the age, body weight, general health, sex, and diet of the subject; the time of administration, route of administration, and rate of excretion of the specific compound employed; the duration of the treatment; drugs used in combination or coincidental with the specific compound employed; and like factors, well known in the medical arts.

Pharmaceutical compositions of the present invention may be administered by any route. In some embodiments, pharmaceutical compositions of the present invention are administered by a variety of routes, including oral (PO), intravenous (IV), intramuscular (IM), intra-arterial, intramedullary, intrathecal, subcutaneous (SQ), intraventricular, transdermal, interdermal, intradermal, rectal (PR), vaginal, intraperitoneal (IP), intragastric (IG), topical (e.g., by powders, ointments, creams, gels, lotions, and/or drops), mucosal, intranasal, buccal, enteral, vitreal, sublingual; by intratracheal instillation, bronchial instillation, and/or inhalation; as an oral spray, nasal spray, and/or aerosol; and/or through a portal vein catheter. In general, the most appropriate route of administration will depend upon a variety of factors including the nature of the agent being administered (e.g., its stability in the environment of the gastrointestinal tract), the condition of the subject (e.g., whether the subject is able to tolerate a particular mode of administration), etc.

In some embodiments, vaccines in accordance with the invention are delivered by multiple routes of administration (e.g., by subcutaneous injection and by intranasal inhalation). For vaccines involving two or more doses, different doses may be administered via different routes.

In some embodiments, vaccines in accordance with the invention are delivered by subcutaneous injection. In some embodiments, vaccines in accordance with the invention are delivered by intranasal inhalation.

In some embodiments, vaccines in accordance with the invention are delivered by oral and/or mucosal routes. Oral and/or mucosal delivery can prime systemic immune response. There has been considerable progress in the development of heterologous expression systems for oral administration of antigens that stimulate the mucosal-immune system and can prime systemic immunity. Previous efforts at delivery of oral vaccine however, have demonstrated a requirement for considerable quantities of antigen in achieving efficacy. Thus, economical production of large quantities of target antigens is a prerequisite for creation of effective oral vaccines. Development of plants expressing antigens, including thermostable antigens, represents a more realistic approach to such difficulties.

In certain embodiments, a *Y. pestis* antigen expressed in a plant or portion thereof is administered to a subject orally by direct administration of a plant to a subject. In some aspects a vaccine protein expressed in a plant or portion thereof is extracted and/or purified, and used for preparation of a pharmaceutical composition. It may be desirable to formulate such isolated products for their intended use (e.g., as a pharmaceutical agent, vaccine composition, etc.). In some embodiments, it will be desirable to formulate products together with some or all of plant tissues that express them.

Where it is desirable to formulate product together with plant material, it will often be desirable to have utilized a plant that is not toxic to the relevant recipient (e.g., a human or other animal). Relevant plant tissue (e.g., cells, roots, leaves) may simply be harvested and processed according to techniques known in the art, with due consideration to maintaining activity of the expressed product. In certain embodiments, it is desirable to have expressed *Y. pestis* antigen in an edible plant (and, specifically in edible portions of the plant) so that the material can subsequently be eaten. For instance, where vaccine antigen is active after oral delivery (when properly formulated), it may be desirable to produce antigen protein in an edible plant portion, and to formulate expressed *Y. pestis* antigen for oral delivery together with some or all of the plant material with which a protein was expressed.

In some embodiments, vaccines in accordance with the invention are administered by subcutaneous, intramuscular, and/or intravenous injection.

In certain embodiments, *Y. pestis* antigens in accordance with the present invention and/or pharmaceutical compositions thereof (e.g., vaccines) in accordance with the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg of subject body weight per day to obtain the desired therapeutic effect. The desired dosage may be delivered more than three times per day, three times per day, two times per day, once per day, every other day, every third day, every week, every two weeks, every three weeks, every four weeks, every two months, every six months, or every twelve months. In certain embodiments, the desired dosage may be delivered using multiple administrations (e.g., two, three, four, five, six, seven, eight, nine, ten, eleven, twelve, thirteen, fourteen, or more administrations).

Compositions are administered in such amounts and for such time as is necessary to achieve the desired result. In certain embodiments, a "therapeutically effective amount" of a pharmaceutical composition is that amount effective for treating, attenuating, or preventing a disease in a subject. Thus, the "amount effective to treat, attenuate, or prevent disease," as used herein, refers to a nontoxic but sufficient amount of the pharmaceutical composition to treat, attenuate, or prevent disease in any subject. For example, the "therapeutically effective amount" can be an amount to treat, attenuate, or prevent infection (e.g., viral infection, $Y.$ pestis infection), etc.

It will be appreciated that $Y.$ pestis antigens in accordance with the present invention and/or pharmaceutical compositions thereof can be employed in combination therapies. The particular combination of therapies (e.g., therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, $Y.$ pestis antigens useful for treating, preventing, and/or delaying the onset of $Y.$ pestis infection may be administered concurrently with another agent useful for treating, preventing, and/or delaying the onset of $Y.$ pestis infection), or they may achieve different effects (e.g., control of any adverse effects). The invention encompasses the delivery of pharmaceutical compositions in combination with agents that may improve their bioavailability, reduce and/or modify their metabolism, inhibit their excretion, and/or modify their distribution within the body.

Pharmaceutical compositions in accordance with the present invention may be administered either alone or in combination with one or more other therapeutic agents. By "in combination with," it is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. In will be appreciated that therapeutically active agents utilized in combination may be administered together in a single composition or administered separately in different compositions. In general, each agent will be administered at a dose and/or on a time schedule determined for that agent.

In general, it is expected that agents utilized in combination with be utilized at levels that do not exceed the levels at which they are utilized individually. In some embodiments, the levels utilized in combination will be lower than those utilized individually.

In certain embodiments, vaccine compositions comprise at least two $Y.$ pestis antigens. For example, certain vaccine compositions can comprise at least two $Y.$ pestis antigens in accordance with the invention (e.g., F1 protein and/or LcrV protein). In some aspects such combination vaccines may include one thermostable fusion protein comprising $Y.$ pestis antigen; in some aspects, two or more thermostable fusion proteins comprising $Y.$ pestis antigen are provided.

Where combination vaccines are utilized, it will be understood that any combination of $Y.$ pestis antigens may be used for such combinations. Compositions may include multiple $Y.$ pestis antigens, including multiple antigens provided herein. Furthermore, compositions may include one or more antigens provided herein with one or more additional antigens. Combinations of $Y.$ pestis antigens include $Y.$ pestis antigens derived from one or more various subtypes or strains such that immunization confers immune response against more than one infection type. Combinations of $Y.$ pestis antigen may include at least one, at least two, at least three, at least four or more antigens derived from different subtypes or strains. In some combinations, at least two or at least three antigens from different subtypes are combined in one vaccine composition. Furthermore, combination vaccines may utilize $Y.$ pestis antigen and antigen from one or more unique infectious agents.

Pharmaceutical Compositions and/or Formulations

The present invention provides $Yersinia$ $pestis$ antigens and pharmaceutical compositions comprising at least one $Y.$ pestis antigen and at least one pharmaceutically acceptable excipient (e.g., vaccine compositions). Such pharmaceutical compositions may optionally comprise one or more additional therapeutically active substances. In accordance with some embodiments, methods of administering a pharmaceutical composition comprising administering $Y.$ pestis antigens to a subject in need thereof are provided. In some embodiments, pharmaceutical compositions are administered to humans. For the purposes of the present disclosure, the phrase "active ingredient" generally refers to a $Y.$ pestis antigen in accordance with the invention. In certain embodiments, a $Y.$ pestis antigen is or comprises F1 protein. In certain embodiments, a $Y.$ pestis antigen is or comprises LcrV protein.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Vaccines may include additionally any suitable adjuvant to enhance the immunogenicity of the vaccine when administered to a subject. For example, such adjuvant(s) may include, without limitation, extracts of Quillaja saponaria (QS), including purified subfractions of food grade QS such as Quil A and QS-21, alum, aluminum hydroxide, aluminum phosphate, MF59, Malp2, incomplete Freund's adjuvant; complete Freund's adjuvant, ALHYDROGEL®, 3 De-O-acylated monophosphoryl lipid A (3D-MPL). Further adjuvants include immunomodulatory oligonucleotides, for example unmethylated CpG sequences as disclosed in WO 96/02555. Combinations of different adjuvants, such as those mentioned hereinabove, are contemplated as providing an adjuvant which is a preferential stimulator of TH1 cell response. For example, QS21 can be formulated together with 3D-MPL. The ratio of QS21:3D-MPL will typically be in the order of 1:10 to 10:1; 1:5 to 5:1; and often substantially 1:1. The desired range for optimal synergy may be 2.5:1 to 1:1 3D-MPL: QS21. Doses of purified QS extracts suitable for use in a human vaccine formulation are from 0.01 mg to 10 mg per kilogram of bodyweight.

It should be noted that certain thermostable proteins (e.g., lichenase) may themselves demonstrate immunoresponse potentiating activity, such that use of such protein whether in a fusion with a *Y. pestis* antigen or separately may be considered use of an adjuvant. Thus, vaccine compositions may further comprise one or more adjuvants. Certain vaccine compositions may comprise two or more adjuvants. Furthermore, depending on formulation and routes of administration, certain adjuvants may be desired in particular formulations and/or combinations.

Pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy*, $21^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, at least 96%, at least 97%, at least 98%, at least 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate)(VEEGUM®), sodium lauryl sulfate, quaternary ammonium compounds, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite [aluminum silicate] and VEEGUM® [magnesium aluminum silicate]), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate [TWEEN®20], polyoxyethylene sorbitan [TWEEN®60], polyoxyethylene sorbitan monooleate [TWEEN®80], sorbitan monopalmitate [SPAN®40], sorbitan monostearate [SPAN®60], sorbitan tristearate [SPAN®65], glyceryl monooleate, sorbitan monooleate [SPAN®80]), polyoxyethylene esters (e.g., polyoxyethylene monostearate [MYRJ®45], polyoxyethylene hydrogenated castor oil, polyethoxylated castor oil, polyoxymethylene stearate, and SOLUTOL®), sucrose fatty acid esters, polyethylene glycol fatty acid esters (e.g., CREMOPHOR®), polyoxyethylene ethers, (e.g., polyoxyethylene lauryl ether [BRIJ®30]), poly (vinyl-pyrrolidone), diethylene glycol monolaurate, triethanolamine oleate, sodium oleate, potassium oleate, ethyl oleate, oleic acid, ethyl laurate, sodium lauryl sulfate, PLURONIC®F 68, POLOXAMER®188, cetrimonium bromide, cetylpyridinium chloride, benzalkonium chloride, docusate sodium, etc. and/or combinations thereof.

Exemplary binding agents include, but are not limited to, starch (e.g., cornstarch, starch paste, etc.); gelatin; sugars (e.g., sucrose, glucose, dextrose, dextrin, molasses, lactose, lactitol, mannitol, etc.); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate [VEEGUM®], larch arabogalactan, etc.); alginates; polyethylene oxide;

polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfate, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfate, sodium metabisulfite, potassium sulfite, potassium metabisulfite, GLYDANT PLUS®, PHENONIP®, methylparaben, GERMALL®115, GERMABEN®II, NEOLONE™; KATHON™, and/or EUXYL®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such a CREMOPHOR®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or fillers or extenders (e.g., starches, lactose, sucrose, glucose, mannitol, and silicic acid), binders (e.g., carboxymethylcellulose, alginates, gelatin, polyvinylpyrrolidinone, sucrose, and acacia), humectants (e.g., glycerol), disintegrating agents (e.g., agar, calcium carbonate, potato starch, tapioca starch, alginic acid, certain silicates, and sodium carbonate), solution retarding agents (e.g., paraffin), absorption accelerators (e.g., quaternary ammonium compounds), wetting agents (e.g., cetyl alcohol and glycerol monostearate), absorbents (e.g., kaolin and bentonite clay), and lubricants (e.g., talc, calcium stearate, magnesium stearate, solid polyethylene glycols, sodium lauryl sulfate), and mixtures thereof In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Vaccine products, optionally together with plant tissue, are particularly well suited for oral administration as pharmaceutical compositions. Oral liquid formulations can be used and may be of particular utility for pediatric populations. Harvested plant material may be processed in any of a variety of ways (e.g., air drying, freeze drying, extraction etc.), depending on the properties of the desired therapeutic product and its desired form. Such compositions as described above may be ingested orally alone or ingested together with food or feed or a beverage. Compositions for oral administration include plants; extractions of plants, and proteins purified from infected plants provided as dry powders, foodstuffs, aqueous or non-aqueous solvents, suspensions, or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medial parenteral vehicles including sodium chloride solution, Ringer's dextrose solution, dextrose plus sodium chloride solution, Ringer's solution containing lactose or fixed oils. Examples of dry powders include any plant biomass that has been dried, for example, freeze dried, air dried, or spray dried. For example, plants may be air dried by placing them in a commercial air dryer at about 120° F. until biomass contains less than 5% moisture by weight. Dried plants may be stored for further processing as bulk solids or further processed by grinding to a desired mesh sized powder. Alternatively or additionally, freeze-drying may be used for products that are sensitive to air-drying. Products may be freeze dried by placing them into a vacuum drier and dried frozen under a vacuum until the biomass contains less than about 5% moisture by weight. Dried material can be further processed as described herein.

Plant-derived material may be administered as or together with one or more herbal preparations. Useful herbal preparations include liquid and solid herbal preparations. Some examples of herbal preparations include tinctures, extracts (e.g., aqueous extracts, alcohol extracts), decoctions, dried preparations (e.g., air-dried, spray dried, frozen, or freeze-dried), powders (e.g., lyophilized powder), and liquid. Herbal preparations can be provided in any standard delivery vehicle, such as a capsule, tablet, suppository, liquid dosage, etc. Those skilled in the art will appreciate the various formulations and modalities of delivery of herbal preparations that may be applied to the present invention.

In some methods, a plant or portion thereof expressing a *Y. pestis* antigen according to the present invention, or biomass thereof, is administered orally as medicinal food. Such edible compositions are typically consumed by eating raw, if in a solid form, or by drinking, if in liquid form. The plant material can be directly ingested without a prior processing step or after minimal culinary preparation. For example, a vaccine antigen may be expressed in a sprout which can be eaten directly. For instance, vaccine antigens expressed in an alfalfa sprout, mung bean sprout, or spinach or lettuce leaf sprout, etc. In some embodiments, plant biomass may be processed and the material recovered after the processing step is ingested.

Processing methods useful in accordance with the present invention are methods commonly used in the food or feed industry. Final products of such methods typically include a substantial amount of an expressed antigen and can be conveniently eaten or drunk. The final product may be mixed with other food or feed forms, such as salts, carriers, favor enhancers, antibiotics, and the like, and consumed in solid, semi-solid, suspension, emulsion, or liquid form. Such methods can include a conservation step, such as, e.g., pasteurization, cooking, or addition of conservation and preservation agents. Any plant may be used and processed in the present invention to produce edible or drinkable plant matter. The amount of *Y. pestis* antigen in a plant-derived preparation may be tested by methods standard in the art, e.g., gel electrophoresis, ELISA, or western blot analysis, using a probe or antibody specific for product. This determination may be used to standardize the amount of vaccine antigen protein ingested. For example, the amount of vaccine antigen may be determined and regulated, for example, by mixing batches of product having different levels of product so that the quantity of material to be drunk or eaten to ingest a single dose can be standardized. A contained, regulatable environment in accordance with the invention, however, should minimize the need to carry out such standardization procedures.

A vaccine protein produced in a plant cell or tissue and eaten by a subject may be preferably absorbed by the digestive system. One advantage of the ingestion of plant tissue that has been only minimally processed is to provide encapsulation or sequestration of the protein in cells of the plant. Thus, product may receive at least some protection from digestion in the upper digestive tract before reaching the gut or intestine and a higher proportion of active product would be available for uptake.

Dosage forms for topical and/or transdermal administration of a compound in accordance with this invention may include ointments, pastes, creams, lotions, gels, powders, solutions, sprays, inhalants and/or patches. Generally, the active ingredient is admixed under sterile conditions with a pharmaceutically acceptable excipient and/or any needed preservatives and/or buffers as may be required. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, the rate may be controlled by either providing a rate controlling membrane and/or by dispersing the compound in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition in accordance with the invention may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and the active ingredient may constitute 0.1% to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions in accordance with the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface-active agent, and/or a preservative such as methylhydroxybenzoate. The droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e., by rapid inhalation through the nasal passage from a container of the powder held close to the nose.

Formulations suitable for nasal administration may, for example, comprise from about as little as 0.1% (w/w) and as much as 100% (w/w) of the active ingredient, and may comprise one or more of the additional ingredients described herein. A pharmaceutical composition in accordance with the invention may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 nm to about 200 nm, and may further comprise one or more of the additional ingredients described herein.

A pharmaceutical composition in accordance with the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

In certain situations, it may be desirable to prolong the effect of a vaccine by slowing the absorption of one or more components of the vaccine product (e.g., protein) that is subcutaneously or intramuscularly injected. This may be accomplished by use of a liquid suspension of crystalline or amorphous material with poor water solubility. The rate of absorption of product then depends upon its rate of dissolution, which in turn, may depend upon size and form. Alternatively or additionally, delayed absorption of a parenterally administered product is accomplished by dissolving or suspending the product in an oil vehicle. Injectable depot forms are made by forming microcapsule matrices of protein in biodegradable polymers such as polylactide-polyglycolide. Depending upon the ratio of product to polymer and the nature of the particular polymer employed, rate of release can be controlled. Examples of biodegradable polymers include poly(orthoesters) and poly(anhydrides). Depot injectable formulations may be prepared by entrapping product in liposomes or microemulsions, which are compatible with body tissues. Alternative polymeric delivery vehicles can be used for oral formulations. For example, biodegradable, biocompatible polymers such as ethylene vinyl acetate, polyanhydrides, polyglycolic acid, collagen, polyorthoesters, and polylactic acid, etc., can be used. Antigen(s) or an immunogenic portions thereof may be formulated as microparticles, e.g., in combination with a polymeric delivery vehicle.

General considerations in the formulation and/or manufacture of pharmaceutical agents may be found, for example, in *Remington: The Science and Practice of Pharmacy* 21$^{st}$ ed., Lippincott Williams & Wilkins, 2005.

Kits

In some embodiments, the present invention provides pharmaceutical packs or kits including *Yersinia pestis* antigens according to the present invention. In certain embodiments, pharmaceutical packs or kits include live sprouted seedlings, clonal entity or plant producing a *Y. pestis* antigen according to the present invention, or preparations, extracts, or pharmaceutical compositions containing vaccine in one or more containers filled with optionally one or more additional ingredients of pharmaceutical compositions in accordance with the invention. In some embodiments, pharmaceutical packs or kits include pharmaceutical compositions comprising purified *Y. pestis* antigen according to the present invention, in one or more containers optionally filled with one or more additional ingredients of pharmaceutical compositions in accordance with the invention. In certain embodiments, the pharmaceutical pack or kit includes an additional approved therapeutic agent (e.g., *Y. pestis* antigen, *Y. pestis* vaccine) for use as a combination therapy. Optionally associated with such container(s) can be a notice in the form prescribed by a governmental agency regulating the manufacture, use or sale of pharmaceutical products, which notice reflects approval by the agency of manufacture, use, or sale for human administration.

Kits are provided that include therapeutic reagents. As but one non-limiting example, *Y. pestis* vaccine can be provided as oral formulations and administered as therapy. Alternatively or additionally, *Y. pestis* vaccine can be provided in an injectable formulation for administration. In some embodiments, *Y. pestis* vaccine can be provided in an inhalable formulation for administration. Pharmaceutical doses or instructions therefor may be provided in the kit for administration to an individual suffering from or at risk for *Y. pestis* infection.

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain information, exemplification and guidance, which can be adapted to the practice of this invention in its various embodiments and the equivalents thereof.

EXEMPLIFICATION

Example 1

A Plant-Produced Plague Vaccine Candidate Confers Protection to Monkeys

*Y. pestis* proteins F1 and LcrV were independently fused to an engineered version of the thermostable enzyme lichenase (LicKM) from *Clostridium thermocellum* (Musiychuk et al., 2007, *Influenza Other Respir. Viruses*, 1:19-25; incorporated herein by reference). Fusions were produced in *Nicotiana benthamiana* and evaluated in Cynomolgus Macaques for immunogenicity and protective efficacy. When administered to monkeys, a mixture of the LicKM fusions to F1 and LcrV was highly immunogenic and protective.

Materials and Methods

Engineering, Expression and Purification of *Y. pestis* Antigens

The LicKM fusion system for producing antigens in plants is described (Musiychuk et al., 2007, *Influenza Other Respir. Viruses*, 1:19-25; incorporated herein by reference). Briefly, sequence encoding full-length mature *Y. pestis* F1 and LcrV were separately cloned into LicKM (GenBank accession number DQ776900) as in-frame fusions to obtain LicKM-F1 and LicKM-LcrV. LicKM-F1 and LicKM-LcrV were individually cloned in the plant expression vector pBID4 to give pBID4-LicKM-F1 and pBID4-LicKM-LcrV, respectively, which were then separately introduced into the *Agrobacterium rhizogenes* strain A4. To produce each target antigen, *A. rhizogenes* strains carrying pBID4-LicKM-F1 and pBID4-LicKM-LcrV were inoculated into *N. benthamiana*, and leaf tissue was harvested 5 days later. Target antigens were purified from homogenized leaves by affinity chromatography followed by ion exchange chromatography. Purified antigens were characterized by SDS-PAGE followed by immunoblotting. To provide control material, LicKM alone was similarly expressed in and purified from *N. benthamiana*.

Cynomolgus Macaques Challenge Study using Plant-Produced *Y. pestis* Antigens

The study was conducted using female Cynomolgus Macaques (Covance Research Products) of approximately 2 years of age and approximately 2 kg weight. For test groups, LicKM-F1 and LicKM-LcrV were mixed at a weight ratio of 1:1 to give the candidate vaccine (CV). Where antigens were to be delivered with adjuvant, they were mixed with 2% ALHYDROGEL® (Accurate Chemical & Scientific Corporation) at a ratio of 1:50 (w/w; antigen/adjuvant). The study comprised four groups: Group 1 (negative control) had two animals and groups 2-4 had three animals per group. Group 1 received 125 µg/dose of LicKM plus adjuvant. Group 2 received 25 µg/dose of CV plus adjuvant. Group 3 received 250 µg/dose of CV plus adjuvant, and group 4 received 250 µg/dose of CV alone. Antigens were administered by subcutaneous injection on study days 1, 14, and 28. Serum samples were collected on days of candidate vaccine administration and 7 days after the final administration. Animals were challenged via nose-only inhalation with *Y. pestis* strain CO 92; Biovar-Orientalis at 100×LD$_{50}$ on study day 40 and observed for a further 14 days.

Analysis of Serum Samples for Immune Responses to Administered Antigens

Sera collected from immunized monkeys were analyzed for the presence of LcrV- and F1-specific IgG and IgA by ELISA. MaxiSorp 96-well plates (Nunc) were coated with 1 µg/ml *Escherichia coli*-produced F1 fused to domain 1 of *Bacillus anthracis* lethal factor (LFD1) or *E. coli*-produced LcrV. Serum samples were added at an initial dilution of 1:100, titrated in five-fold dilutions, and target-specific antibodies were detected using goat anti-monkey IgG (KPL) or IgA (Fitzgerald Industries International Inc.) conjugated to HRP.

Analysis of Tissue Pathogen Load

Tissues from all challenged animals were evaluated for presence of *Y. pestis*. Tissues were placed in 1% peptone and individually homogenized. Tissue homogenates were serially diluted in 1% peptone, and 100 µl aliquots were spread plated on 90 mm tryptic soy agar (TSA) plates in triplicate. TSA plates were incubated at 28° C. for 36 h-48 h, after which *Y. pestis* colonies were counted. Pathogen load is expressed as colony forming units (CFU).

Results

Expression of *Y. pestis* F1 and LcrV Antigens as Fusions to LicKM in *N. benthamiana*

Figure 2:
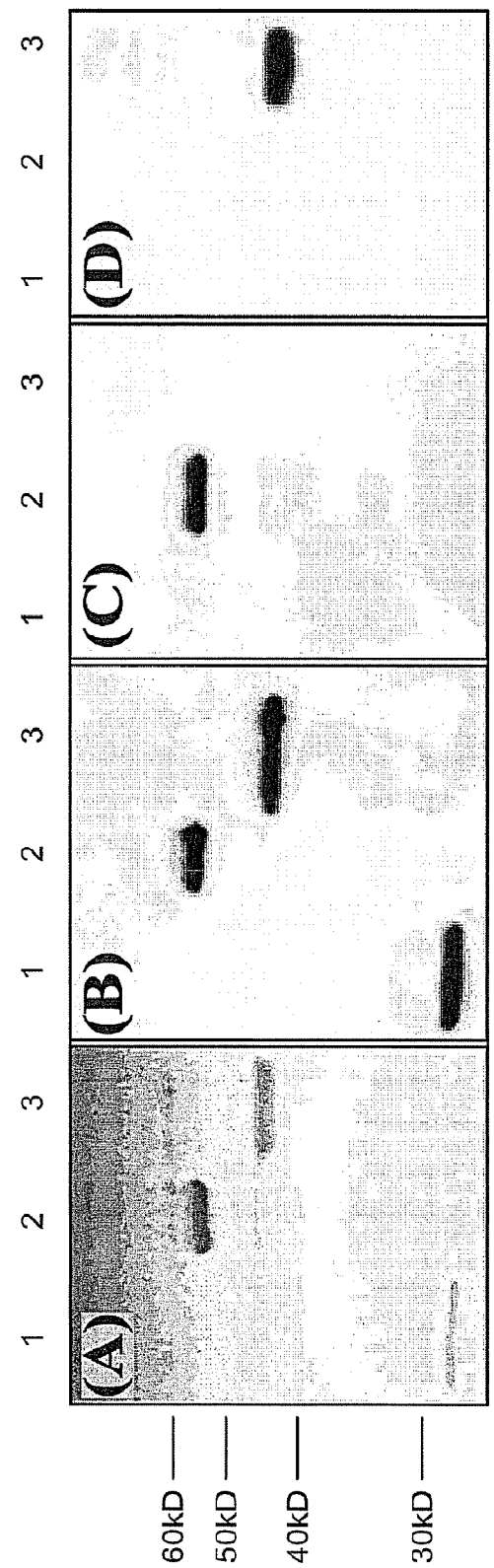
FIG. 2. In vitro characterization of plant-produced *Y. pestis* antigens. Plant-produced LicKM (Lane 1), LicKM-LcrV (Lane 2), and LicKM-F1 (Lane 3) were analyzed by SDS-PAGE followed by Coomassie staining (A) and immunoblotting using rabbit polyclonal anti-LicKM (B), mouse monoclonal anti-LcrV (C), and mouse monoclonal anti-F1 (D) antibodies.

LicKM, LicKM-F1, and LicKM-LcrV were purified from *N. benthamiana* leaf tissue and analyzed by SDS-PAGE and immunoblot (FIG. 2). Gels were stained with Coomassie Brilliant Blue to show purified LicKM, LicKM-F1, and LicKM-LcrV (FIG. 2A). On average, 380 µg LicKM-F1 and 120 µg of LicKM-LcrV was purified per gram of fresh leaf tissue. In immunoblot assays, antibodies specific for LicKM reacted with LicKM and both fusion proteins (FIG. 2B), whereas antibodies specific for either LcrV (FIG. 2C) or F1 (FIG. 2D) reacted only with their respective LicKM fusion proteins.

Immunogenicity and Protective Efficacy of Plant-Produced F1 and LcrV

To evaluate immunogenicity and protective efficacy of plant-produced antigens, animals were immunized with a mixture of LicKM-F1 and LicKM-LcrV or with LicKM alone. Serum samples were assessed for the presence of IgG and IgA specific to LcrV and F1. All animals in group 3 mounted a strong IgG response against both LcrV (FIG. 3A) and F1 (FIG. 3B). IgG antibody titers against LcrV approached peak values following the priming dose and did not substantially increase following booster doses. In group 4, which received the same dose of antigen but in the absence of adjuvant, IgG responses specific to LcrV were up to two logs lower than group 3 following the priming dose and remained significantly lower than group 3 even after booster doses (FIG. 3A). Also, the IgG response to F1 in group 4 was negligible, even after the two boosts (FIG. 3B). These results indicate that adjuvant can help stimulate high titer antibody responses Animals in group 2 that were immunized with 10-fold less antigen in the presence of adjuvant produced anti-LcrV antibodies with titers as high as group 3 (FIG. 3A). However, F1-specific IgG titers in this group were approximately two logs lower than group 3 (FIG. 3B). Production of serum LcrV-specific IgA was detected at similar levels in animals in groups 2 and 3 and peaked after the prime (FIG. 3C). Group 4 animals produced detectable amounts of serum IgA against LcrV (FIG. 3C), although at lower titers than observed in groups 2 and 3. In all test groups, F1-specific serum IgA responses were lower than LcrV-specific IgA responses and were not measurable in all animals (FIG. 3D). No LcrV- or F1-specific antibodies were detected in control animals.

Following immunization, vaccinated animals were challenged with aerosolized *Y. pestis*. All animals in group 1 developed clinical signs of disease and succumbed to death 5 days after challenge (FIG. 3E). By contrast, all animals in group 3 survived the challenge, indicating that the plant-produced LicKMF1/LicKM-LcrV antigen mixture is fully protective. Two of the three animals in group 2 survived the challenge but, none of the animals in group 4 survived (FIG. 3E). Post-mortem analysis of pathogen load in different organs of animals that survived the challenge revealed no *Y. pestis*, whereas organs collected from animals that died of challenge had high titers of bacteria (Table 2).

TABLE 2

Tissue Pathogen Load (CFU) in Monkeys Following *Y. pestis* Challenge

| Group | Spleen | Liver | Lymph Node | Lung |
|---|---|---|---|---|
| 1 | >2 × 10$^6$ | >2.5 × 10$^6$ | >6.8 × 10$^6$ | >7.4 × 10$^6$ |
|  | >2 × 10$^6$ | >2 × 10$^6$ | >1.1 × 10$^7$ | >2.3 × 10$^6$ |
| 2 | >2 × 10$^6$ | >2 × 10$^6$ | >2 × 10$^6$ | >2 × 10$^6$ |
|  | 0 | 0 | 0 | 0 |
|  | 0 | 0 | 0 | 0 |
| 3 | 0 | 0 | 0 | 0 |
|  | 0 | 0 | 0 | 0 |
|  | 0 | 0 | 0 | 0 |
| 4 | 3.3 × 10$^6$ | 5.8 × 10$^6$ | 3.6 × 10$^8$ | >4 × 10$^9$ |
|  | >2 × 10$^6$ | >3.1 × 10$^6$ | >9.9 × 10$^6$ | >2.9 × 10$^6$ |
|  | 2 × 10$^9$ | 4.4 × 10$^8$ | 1.3 × 10$^9$ | >8.3 × 10$^9$ |

In summary, plant-produced antigens stimulated strong antibody responses and provided full protection against challenge with aerosolized *Y. pestis* in primates. The present invention encompasses the recognition that plant-produced *Y. pestis* antigens may stimulate strong antibody responses and provide full or partial protection against *Y. pestis* infection in humans, non-human primates, and other mammals (e.g., cats, dogs, mice, rats, horses, cows, etc.).

Example 2

A Plant-Produced Plague Double Fusion Vaccine Candidate Stimulates High Titers of Antigen-Specific IgG and Confers Protection to Mammals

*Y. pestis* proteins F1 and LcrV were both fused to an engineered version of the thermostable enzyme lichenase (LicKM) from *Clostridium thermocellum* (Musiychuk et al., 2007, *Influenza Other Respir. Viruses*, 1:19-25; incorporated herein by reference). LcrV protein was fused into the loop region of LicKM, and F1 protein was fused to the C-terminus of LicKM. Fusions were produced in *Nicotiana benthamiana*, and serum LcrV- and F1-specific IgG titers were measured. Fusions were also evaluated in Cynomolgus Macaques for immunogenicity and protective efficacy. When administered to monkeys, the double fusion generated high LcrV- and F1-specific IgG titers, and the double fusion was found to be highly immunogenic and protective.

Engineering, Expression, and Purification of *Y. pestis* Double Fusion Antigen

The LicKM fusion system for producing antigens in plants is described (Musiychuk et al., 2007, *Influenza Other Respir. Viruses*, 1:19-25; incorporated herein by reference). Briefly, sequence encoding full-length mature *Y. pestis* F1 and LcrV were both cloned into LicKM (GenBank accession number DQ776900) as in-frame fusions to obtain LcrV-F1-LicKM. LcrV was cloned into the loop region of LicKM, and F1 was fused to the C-terminus of LicKM.

The nucleotide sequence of the double fusion construct, which encodes the double fusion protein antigen, is:

(SEQ ID NO: 11)
5'GGTACC*GGATCCTTAATTAA*ATGGGTTTCGTGCTTTTCTCTCA

GCTTCCTTCTTTCCTTCTTGTGTCTACCCTTCTTCTTTTCCTTGT

GATTTCTCACTCTTGCAGGGCTCAGAATGGTGGTTCTTACCCTTA

CAAGTCTGGTGAGTACAGGACCAAGTCTTTCTTCGGTTACGGTTA

CTACGAAGTGAGAATGAAGGCTGCTAAGAATGTGGGTATTGTGTC

ATCTTTCTTCACCTACACCGGTCCTTCAGATAATAACCCTTGGGA

TGAGATTGATATTGAGTTCCTTGGAAAGGATACCACCAAGGTTCA

GTTCAACTGGTACAAGAACGGTGTTGGTGGAAATGAGTACCTTCA

CAACCTTGGTTTCGATGCTTCTCAGGATTTCCACACCTACGGTTT

TGAGTGGAGGCCTGATTACATTGATTTCTACGTGGATGGAAAGAA

GGTTTACAGGGGAACCAGGAACATTCCTGTTACCCCTGGAAAGAT

TATGATGAACCTTTGGCCTGGTATTGGTGTTGATGAGTGGCTTGG

TAGATACGATGGAAGGACTCCTCTTCAGGCTGAGTACGAGTACGT

TAAGTACTACCCTAACGGT*AGATCT*ATGATTAGGGCTTACGAGCA

GAATCCTCAGCACTTCATTGAGGATCTTGAGAAAGTTAGGGTGGA

GCAGCTTACTGGTCATGGTTCTTCAGTGCTTGAAGAGCTTGTTCA

GCTTGTGAAGGATAAGAACATTGATATTTCTATTAAGTACGATCC

TAGGAAGGATTCTGAGGTGTTCGCTAACAGAGTGATTACCGATGA

TATTGAGCTTCTGAAGAAGATTCTTGCTTACTTCCTTCCTGAGGA

TGCTATTCTTAAGGGTGGTCACTACGATAATCAGCTTCAGAACGG

TATTAAGAGGGTGAAAGAGTTCCTTGAGTCATCTCCTAATACCCA

GTGGGAGCTTAGGGCTTTTATGGCTGTGATGCACTTCTCTCTTAC

CGCTGATAGGATTGATGATGATATTCTTAAAGTGATTGTGGATTC

TATGAACCACCATGGTGATGCTAGGTCTAAGTTGAGGGAAGAGCT

TGCTGAACTTACCGCTGAGTTGAAAATCTACTCTGTGATTCAGGC

TGAGATTAACAAGCACCTTTCTTCATCTGGAACCATTAACATTCA

CGATAAGTCTATTAACCTTATGGATAAGAACCTTTACGGTTACAC

CGATGAAGAGATTTTCAAGGCTTCTGCTGAGTACAAGATTCTTGA

GAAGATGCCTCAGACTACCATTCAAGTGGATGGTTCTGAGAAGAA

AATTGTGTCTATTAAGGATTTCCTTGGATCTGAGAACAAGAGGAC

TGGTGCTTTGGGTAACCTTAAGAACTCTTACTCTTACAACAAGGA

TAACAACGAGCTTTCTCACTTCGCTACTACCTGCTCTGATAAGTC

TAGGCCTCTTAACGATCTTGTGTCTCAAAAGACCACCCAGCTTTC

TGATATTACCTCTAGGTTCAACTCTGCTATTGAGGCTCTTAACAG

ATTCATTCAGAAATACGATTCTGTGATGCAAAGGCTTCTTGATGA

TACCTCTGGAAAG*AAGCTT*GTTGTTAACACCCCTTTCGTGGCTGT

TTTCTCTAACTTCGATTCTTCAGTGGGAAAAGGCTGATTGGGC

TAACGGTTCTGTGTTCAACTGTGTGTGGAAGCCTTCTCAGGTGAC

CTTCTCTAACGAAAGATGATTCTTACCCTTGATAGGGAATAC

*GTCGAC*GCTGATTTGACTGCTTCTACTACTGCTACTGCTACTC

TTGTTGAGCCTGCTAGGATTACCCTTACCTACAAAGAGGGTGCTC

CTATTACTATTATGGATAACGGTAACATTGATACCGAGTTGCTTG

TGGGTACTCTTACACTTGGTGGTTACAAGACCGGTACTACCTCTA

CTTCTGTGAACTTCACCGATGCTGCTGGTGATCCTATGTACCTTA

CCTTCACCTCTCAGGATGGAAATAACCACCAGTTCACCACCAAAG

TGATTGGAAAGGATTCTAGGGATTTCGATATTTCTCCTAAGGTGA

ACGGTGAAAATCTTGTGGGTGACGATGTTGTTCTTGCTACCGGTT

CACAGGATTTCTTTGTGAGATCAATTGGTTCTAAGGGTGGAAAGT

TGGCTGCTGGAAAGTACACTGATGCTGTGACTGTGACTGTGTCTA

ATCAG*GTCGAC*CATCATCATCATCACCACAAGGATGAGCTTTGAT

GA*CTCGAGCTC* 3'.

The plain text sequences correspond to LicKM sequences (e.g., CAG...GGT, SEQ ID NO: 12; and GGT...TAC, SEQ ID NO: 13), a 6x-His tag (i.e., 5' CATCATCATCATCAC-CAC 3' SEQ ID NO: 14), and an ER retention signal (i.e., 5' AAGGATGAGCTT 3' SEQ ID NO: 15). The bold, underlined sequence ATG...GCT (SEQ ID NO: 16) corresponds to the PR1a signal peptide. The bold, underlined sequence ATG...AAG (SEQ ID NO: 17) corresponds to LcrV protein coding sequence. The bold, underlined sequence GCT...CAG (SEQ ID NO: 18) corresponds to F1 protein coding sequence. The bold, italicized sequence GGATCCTTAATTAA (SEQ ID NO: 19) corresponds to a BamHI site (i.e., GGATCC, SEQ ID NO -continued <u>DNGNIDTELLVGTLTLGGYKTGTTSTSVNFTDAAGDPMYLTFTSQDG</u>

<u>NNHQFTTKVIGKDSRDFDISPKVNGENLVGDDVVLATGSQDFFVRSI</u>

<u>GSKGGKLAAGKYTDAVTVTVSNQ</u>*VD*HHHHHHKDEL 3'.

The plain text sequences correspond to LicKM sequences (e.g., QNG . . . PNG, SEQ ID NO: 28; and VVN . . . REY, SEQ ID NO: 29), a 6x-His tag (i.e., HHHHHH, SEQ ID NO: 30), and an ER retention signal (i.e., KDEL; SEQ ID NO: 31). The bold, underlined sequence MGF...CRA (SEQ ID NO: 32) corresponds to the PR1a signal peptide. The bold, underlined sequence MIR...SGK (SEQ ID NO: 33) corresponds to LcrV protein coding sequence. The bold, underlined sequence ADL...SNQ (SEQ ID NO: 34) corresponds to F1 protein coding sequence. The bold, italicized sequence RS (SEQ ID NO: 35) corresponds to a BgIII site. The bold, italicized sequence KL (SEQ ID NO: 36) corresponds to a HindIII site. The bold, italicized sequences VD (SEQ ID NO: 37) correspond to two SalI sites.

To provide control material, LicKM alone was similarly expressed in and purified from *N. benthamiana*.

LicKM-F1 and LicKM-LcrV were individually cloned in the plant expression vector pGREENII to give pGREEN-LcrV-F1-LicKM, which was introduced into *Agrobacterium rhizogenes*. *A. rhizogenes* were inoculated into *N. benthamiana*, and leaf tissue was harvested (e.g., about 5 days later). Target antigens were purified from homogenized leaves by chromatography steps (e.g., affinity chromatography followed by ion exchange chromatography). Purified antigens were characterized by Coomassie brilliant blue staining and by SDS-PAGE followed by immunoblotting. To provide control material, LicKM alone was similarly expressed in and purified from *N. benthamiana*.

Cynomolgus Macaques Challenge Study using Plant-Produced *Y. pestis* Antigens

Five groups of female monkeys (five in Groups 1 and 3, eight in Group 2 and 4, and four in Group 5) each received either a vaccination as outlined in Table 3. Monkeys received each dose on Study Days 1, 14, and 28 using modes of administration specified in Table 3.

were blood pressure measurements and radiographs. A physical examination of each monkey was conducted by a licensed veterinary technician under the supervision of a veterinarian prior to initiation of vaccination, before pathogen challenge, and prior to euthanasia. Subcutaneous body temperatures were obtained twice daily during the study beginning on Study Day 7. Serum samples were obtained periodically to assess antibody titers. Vaginal wash specimens were obtained periodically during the study to assess mucosal antibody titers. Clinical pathology (e.g., hematology and serum chemistry) was assessed periodically pre- and post-challenge. *Y. pestis* load was determined in whole blood at defined intervals. Selected tissues from dead or euthanized animals were also evaluated for *Y. pestis* load. Tissue specimens were obtained from all animals and preserved in 10% buffered formalin. Selected tissues were evaluated for histopathology.

Results and Discussion

Expression of *Y. pestis* F1 and LcrV Antigens as a Double Fusion to LicKM

Figure 4:
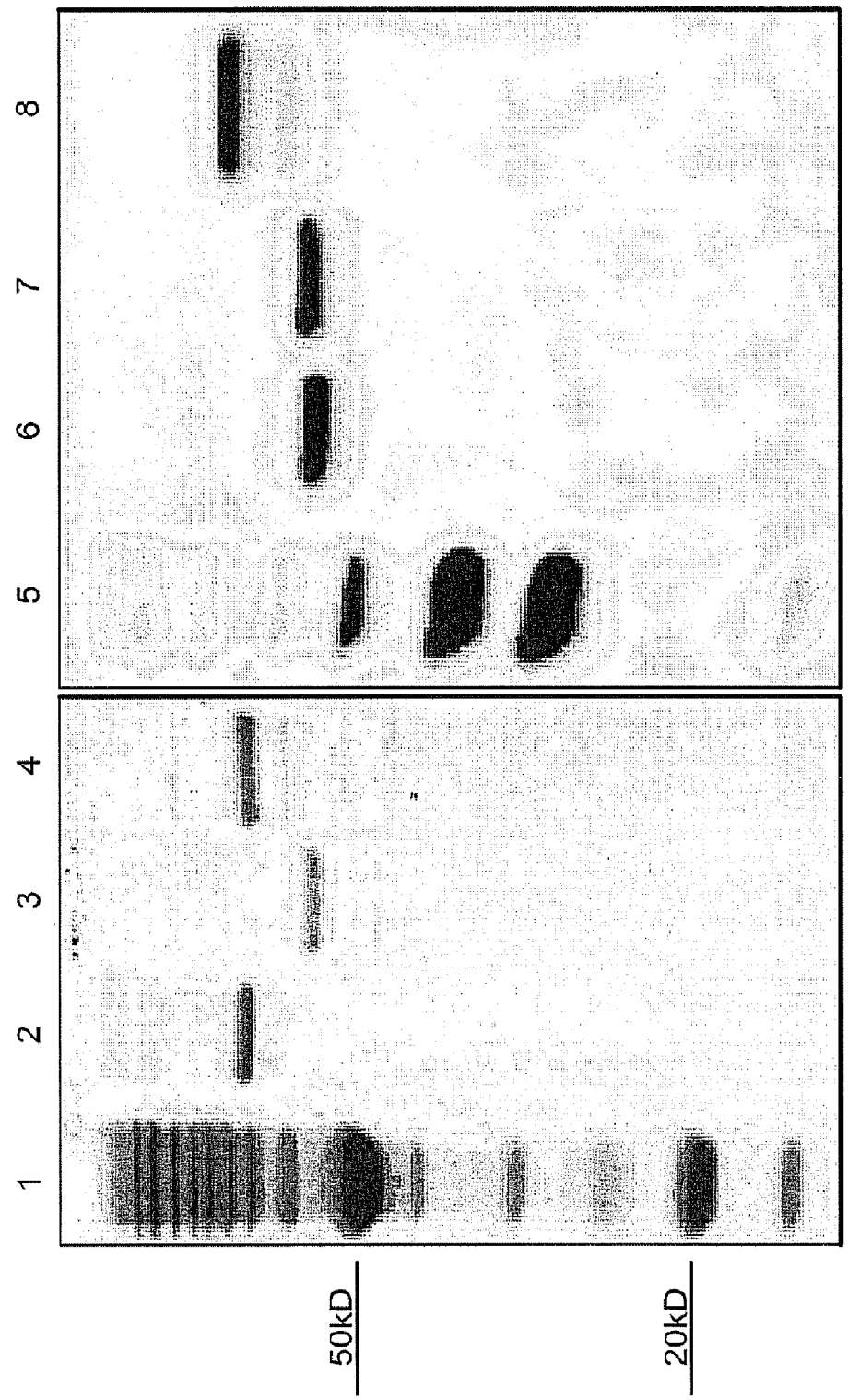
FIG. 4. Production of LcrV-F1-LicKM fusion protein. Lanes 1-4: Coomassie Brilliant Blue staining. Lanes 5-8: western blot using α-lichenase antibody. Lanes 1 and 5: molecular weight markers. Lane 2: bovine serum albumin. Lanes 3 and 7: LcrV-LicKM fusion. Lanes 4 and 8: LcrV-F1-LicKM fusion protein, wherein LcrV is inserted into the loop region of LicKM, and F1 is fused to LicKM as a C-terminal fusion. Lane 6: LicKM-LF fusion.

LcrV-F1-LicKM was purified from *N. benthamiana* leaf tissue and analyzed by SDS-PAGE and immunoblot (FIG. 4, lanes 5-8). Gels were stained with Coomassie Brilliant Blue to show purified LcrV-F1-LicKM (FIG. 4, lanes 1-4). In immunoblot assays, antibodies specific for LicKM reacted with LicKM, with the double fusion protein, and with a fusion of LicKM to an unrelated protein (i.e., anthrax lethal factor (LF) protein) (FIG. 4).

Immunogenicity and Protective Efficacy of Plant-Produced F1-LcrV-LicKM

To evaluate immunogenicity and protective efficacy of plant-produced F1-LcrV-LicKM double fusion antigens, animals were immunized with the double fusion, with a mixture of LicKM-F1 and LicKM-LcrV, or with LicKM alone (see Table 3). Serum samples were assessed at Study Days −9 (i.e., 9 days prior to the first immunization dose), 14, 28, and 35 for the presence of IgG specific to LcrV and F1. All animals in Group 2 (i.e., mixture of LicKM-F1 and LicKM-LcrV plus two adjuvants administered thrice by subcutaneous injection) and Group 5 (i.e., F1-LcrV-LicKM double fusion plus two adjuvants) mounted strong IgG responses against both LcrV

TABLE 3

Double Fusion Vaccine Administration

| | Vaccine Composition | Dose | Route and Frequency |
|---|---|---|---|
| Group 1 | LicKM alone | 125 µg + ALHYDROGEL ® + QuilA | subcutaneous injection, thrice |
| Group 2 | LicKM-F1 + LicKM-LcrV | 250 µg + ALHYDROGEL ® + QuilA | subcutaneous injection, thrice |
| Group 3 | Lic KM alone | (a) 125 µg + ALHYDROGEL ® + QuilA<br>(b) 125 µg (no adjuvant) | (a) subcutaneous, once<br>(b) intranasal, second and third |
| Group 4 | LicKM-F1 + LicKM-LcrV | (a) 250 µg + ALHYDROGEL ® + QuilA<br>(b) 250 µg (no adjuvant) | (a) subcutaneous, once<br>(b) intranasal, second and third |
| Group 5 | LcrV-F1-LicKM double fusion | 250 µg + ALHYDROGEL ® + QuilA | subcutaneous injection, thrice |

All monkeys were challenged via inhalation with a multiple $LD_{50}$ inhalation dose of *Y. pestis* on Study Day 40. Monkeys were evaluated for 14 days post pathogen challenge for disease development and mortality. Evaluations during the study included twice daily clinical observations and qualitative assessment of food consumption. Body weights were obtained at predetermined times during the experiment as (FIGS. 5A and 5C) and F1 (FIGS. 5B and 5D). Immune responses mounted by animals in Group 1 (i.e., LicKM alone plus two adjuvants) were 1-2 logs lower than those mounted by animals in Group 2 or Group 5 after the first immunization dose.

Figure 6:
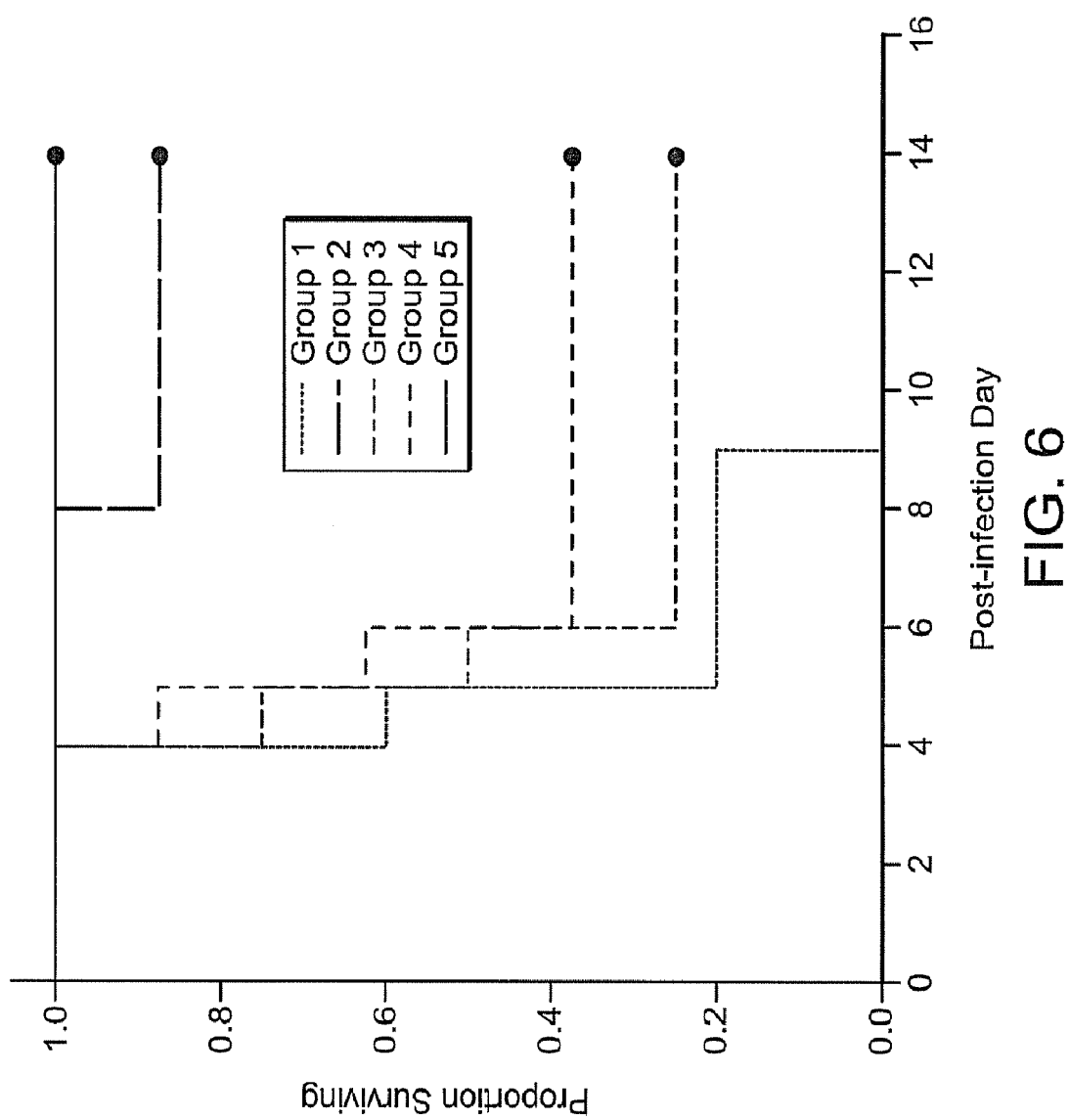
FIG. 6. Survival of groups of female cynomolgus monkeys vaccinated three times subcutaneously or subcutaneously as a priming vaccination followed by twice intranasal vaccinations. The two plant-produced antigens (i.e., F1 and LcrV) were presented to monkeys as a mixture of independently-derived fusion products with LicKM or as a double fusion product (LicKM-F1-LcrV). Group 1 (●●●●●●) a control group with LicKM, received 125 µg LicKM plus two adjuvants. Group 2 (- - -) monkeys received 250 µg LicKM-F1 and LicKM-LcrV mixture plus two adjuvants. Both groups were vaccinated subcutaneously, thrice. Group 3 (-●●-●●-●●), a control group, received 125 µg LicKM plus two adjuvants as a subcutaneous priming dose followed by two intranasal doses without adjuvant at two week intervals. Group 4 (- - - -) received 250 µg LicKM-F1 and LicKM-LcrV mixture plus two adjuvants as a subcutaneous priming dose followed by two intranasal doses without adjuvant at two week intervals. Group 5 (———) received 250 µg LicKM-F1-LcrV double fusion product plus two antigens three times subcutaneously at two week intervals. On post-infection day 0 (Study Day 40), all monkeys were exposed to multiple LD$_{50}$ inhalation dose of *Y. pestis* CO92. Monkeys were followed up to post-infection day 14 (Study Day 54).

Following immunization, vaccinated animals were challenged with aerosolized *Y. pestis*. All five animals in Group 1 developed clinical signs of disease and succumbed to death or were considered moribund (and were, therefore, euthanized) within 9 days after challenge (i.e., about 0% survival). By contrast, seven of eight animals in Group 2 survived the challenge (i.e., about 88% survival). Three of four monkeys in Group 3 died (i.e., about 75% survival). Five of eight monkeys in Group 4 were found dead or were considered moribund (and were, therefore, euthanized) within 6 days after challenge (i.e., about 38% survival). All five monkeys in Group 5 survived to the end of the study (i.e., about 100% survival). Survival data are summarized in FIG. 6.

At study initiation, all monkeys were below the level of detection for *Y. pestis*. Post-pathogen exposure, all monkeys that did not survive to study termination were bacteremic. Group 1: By post-immunization day 2 bacteria was detected in one of five monkeys and by post-immunization day 3 two of five were bacteremic. Bacteria were not detected in the blood of the remaining three monkeys although as discussed below, pathogen was cultured from their tissues. Group 2: Only one monkey in this group did not to survive to study termination. Bacteria were not found in its blood, but there was substantial tissue tropism. The remaining monkeys in this group had pathogen levels below the detectable level (except one monkey displayed small but transient presence on post-immunization day 4). Group 3: Three of the four monkeys exposed to the pathogen had detectable blood levels of *Y. pestis*. One monkey had no detectable levels of *Y. pestis*. Pathogen was not detected in any of the tissues taken at study termination. Group 4: The five monkeys that did not survive to the end of the study had bacteria in their blood, and the three monkeys that survived to study termination were below the level of pathogen detection. Group 5: All four monkeys in this group survived to study termination with no detectable blood levels of pathogen.

All monkeys that did not survive to the end of the study (i.e., monkeys that did not survive to post-immunization day 14) exhibited tissue pathogen loads in all of the tissues evaluated. Pathogen tropism was most evident for lymph nodes and lung. For monkeys that survived to post-immunization day 14, there was no detectable pathogen in the evaluated tissues.

In summary, plant-produced F1-LcrV-LicKM double fusion protein antigens stimulated strong antibody responses and provided 100% protection against challenge with aerosolized *Y. pestis* in primates. The present invention encompasses the recognition that results obtained in mammals (e.g., primates) can be predictive of therapeutic and/or prophylactic efficacy in humans. The present invention encompasses the recognition that plant-produced *Y. pestis* antigens may stimulate strong antibody responses and provide full or partial protection against *Y. pestis* infection in humans, non-human primates, and other mammals (e.g., cats, dogs, mice, rats, horses, cows, etc.).

EQUIVALENTS AND SCOPE

Those skilled in the art will recognize, or be able to ascertain using no more than routine experimentation, many equivalents to the specific embodiments of the invention, described herein. The scope of the present invention is not intended to be limited to the above Description, but rather is as set forth in the appended claims.

Those skilled in the art will recognize, or be able to ascertain using no more than routine experimentation, many equivalents to the specific embodiments of the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any *Y. pestis* strain; any *Y. pestis* protein; any fusion protein; any expression system; any plant production system; any method of administration; etc.) can be excluded from any one or more claims, for any reason, whether or not related to the existence of prior art.

What is claimed is:

1. An isolated antigen comprising a *Yersinia pestis* protein fused to a modified thermostable protein; wherein the *Yersinia pestis* protein comprises a full-length F1 protein that is at least 95% identical to the sequence set forth as SEQ ID NO: 1, 3, 5, or 7, and wherein the modified thermostable protein is a LicKM protein.

2. The isolated antigen of claim 1, wherein the *Yersinia pestis* protein comprises an amino acid sequence that is at least 98% identical to the sequence set forth as SEQ ID NO: 1, 3, 5, or 7.

3. The isolated antigen of claim 1, wherein the *Yersinia pestis* protein comprises the amino acid sequence set forth as SEQ ID NO.: 1, 3, 5, or 7.

4. The isolated antigen of claim 1, wherein the *Yersinia pestis* protein fused to the modified thermostable protein is one or more of an N-terminal fusion, a C-terminal fusion, or a surface loop insertion fusion protein.

5. A vaccine composition comprising a pharmaceutically acceptable carrier and an antigen comprising a *Yersinia pestis* protein fused to a modified thermostable protein, wherein the *Yersinia pestis* protein comprises a full-length F1 protein that is at least 95% identical to the sequence set forth as SEQ ID NO: 1, 3, 5, or 7;
wherein the modified thermostable protein is a LicKM protein; and wherein the composition is capable of eliciting an immune response upon administration to a subject.

6. The vaccine composition of claim 5, wherein the *Yersinia pestis* protein comprises an amino acid sequence that is at least 98% identical to the sequence set forth as SEQ ID NO: 1, 3, 5, or 7.

7. The vaccine composition of claim 5, wherein the *Yersinia pestis* protein comprises the amino acid sequence set forth as SEQ ID NO.: 1, 3, 5, or 7.

8. The vaccine composition of claim 5, wherein the *Yersinia pestis* protein fused to the modified thermostable protein is one or more of an N-terminal fusion, a C-terminal fusion, or a surface loop insertion fusion protein.

9. The vaccine composition of claim 5, wherein the antigen is produced in a plant selected from a transgenic plant and a plant transiently expressing the antigen.

10. The vaccine composition of claim 5, wherein the composition comprises antigen which is purified, partially purified, or unpurified from plant cells, a plant, seeds, fruit, or an extract thereof.

11. The vaccine composition of claim 5, further comprising at least one vaccine adjuvant.

12. The vaccine composition of claim 11, wherein the adjuvant is selected from the group consisting of complete Freund's adjuvant, incomplete Freund's adjuvant, alum, MF59, saponin, aluminum hydroxide, QuilA, and macrophage-activating lipopeptide (Malp-2).

13. A method for inducing a protective immune response against *Yersinia pestis* infection in a subject comprising administering to a subject an effective amount of an anti-*Yersinia pestis* vaccine composition, wherein the administration is sufficient to stimulate production of antigen specific antibodies or stimulate a cellular immune response by the subject; thereby inducing a protective immune response; wherein the vaccine composition comprises an antigen comprising a *Yersinia pestis* protein fused to a modified thermostable protein; and wherein the *Yersinia pestis* protein comprises a full-length F1 protein that is at least 95% identical to the sequence set forth as SEQ ID NO: 1, 3, 5, or 7; and wherein the modified thermostable protein is a LicKM protein.

14. The method of claim 13, wherein the composition is administered orally, intranasally, subcutaneously, intravenously, intraperitoneally, or intramuscularly.

15. The method of claim 14, wherein the composition is administered orally via feeding plant cells to the subject.

16. The method of claim 13, wherein the subject is human.

17. The method of claim 13, wherein the *Yersinia pestis* protein comprises an amino acid sequence that is at least 98% identical to the sequence set forth as SEQ ID NO: 1, 3, 5, or 7.

18. The method of claim 13, wherein the *Yersinia pestis* protein comprises the amino acid sequence set forth as SEQ ID NO: 1, 3, 5, or 7.

* * * * *